US012644126B2

(12) United States Patent
Too et al.

(10) Patent No.: US 12,644,126 B2
(45) Date of Patent: Jun. 2, 2026

(54) UNIVARIANT EXTRINSIC INITIATOR CONTROL SYSTEM FOR MICROBES AND AN IN VITRO ASSEMBLY OF LARGE RECOMBINANT DNA MOLECULES FROM MULTIPLE COMPONENTS

(71) Applicants: National University of Singapore, Singapore (SG); Massachusetts Institute of Technology, Cambridge, MA (US)

(72) Inventors: Heng Phon Too, Singapore (SG); Ruiyang Zou, Singapore (SG); Gregory N. Stephanopoulos, Winchester, MA (US)

(73) Assignees: National University of Singapore, Singapore (SG); Massachusetts Institute of Technology, Massachusetts (MA)

( * ) Notice: Subject to any disclaimer, the term of this patent is extended or adjusted under 35 U.S.C. 154(b) by 1248 days.

(21) Appl. No.: 17/453,238

(22) Filed: Nov. 2, 2021

(65) Prior Publication Data

US 2022/0119823 A1 Apr. 21, 2022

Related U.S. Application Data

(62) Division of application No. 16/447,418, filed on Jun. 20, 2019, now Pat. No. 11,180,764, which is a division of application No. 14/441,447, filed as application No. PCT/SG2013/000486 on Nov. 15, 2013, now abandoned.

(60) Provisional application No. 61/726,795, filed on Nov. 15, 2012.

(51) Int. Cl.

| | |
|---|---|
| *C12N 15/67* | (2006.01) |
| *C07H 21/00* | (2006.01) |
| *C12N 15/52* | (2006.01) |
| *C12N 15/63* | (2006.01) |
| *C12N 15/68* | (2006.01) |
| *C12N 15/69* | (2006.01) |

(52) U.S. Cl.
CPC ............ *C12N 15/67* (2013.01); *C07H 21/00* (2013.01); *C12N 15/52* (2013.01); *C12N 15/63* (2013.01); *C12N 15/68* (2013.01); *C12N 15/69* (2013.01); *C12N 2800/40* (2013.01); *C12N 2840/002* (2013.01)

(58) Field of Classification Search
None
See application file for complete search history.

(56) References Cited

U.S. PATENT DOCUMENTS 6,086,890 A 7/2000 Mittal et al.
11,180,764 B2 * 11/2021 Too ......................... C12N 15/52

2004/0029229 A1 2/2004 Reeves et al.
2015/0284729 A1 10/2015 Too et al.
2019/0330642 A1 10/2019 Too et al.

FOREIGN PATENT DOCUMENTS

WO WO 2009/104964 A1 8/2009
WO WO 2011/060057 A1 5/2011

OTHER PUBLICATIONS

Ajikumar, P.K. et al., Isoprenoid pathway optimization for Taxol precursor overproduction in *Escherichia coli, Science*, 330(6000): 70-74 (Oct. 1, 2010).
Blanusa, M. et al., "Phosphorothioate-based ligase-independent gene cloning (PLICing): An enzyme-free and sequence-independent cloning method", *Analytical Biochemistry*, 406(2): 141-146 (Nov. 15, 2010).
Blatny, J.M. et al. "Improved broad-host-range RK2 vectors useful for high and low regulated gene expression levels in gram-negative bacteria", *Plasmid*, 38(1): 35-51 (Jul. 1997).
Brieba et al., "The T7 Polymerase Intercalating Hairpin is Important for Promoter Opening during Initiation but Not for RNA Displacement of Transcription Bubble Stability during Elongation" 40 Biochemistry 3882-3890 (Year: 2001).
Carlsen, S. et al., "Heterologous expression and characterization of bacterial 2-C-methyl-D-erythirtol-4-phosphate pathway in *Saccharomyces cerevisiae*", *Applied Microbiology Biotechnology* 97:(13): 5753-5769 (Jul. 13, 2013).
Dayhoff, M.O. et al., Atlas of protein sequence and structure, *Nat. Biomed. Res. Found.*, 5(3): 345-358 (1978).
Gish, G. and Eckstein, F., "DNA and RNA sequence determination based on phosphorothioate chemistry", *Science*, 240(4858): 1520-1522 (Jun. 10, 1988).
Guo, et al., "Weakening of the T7 Promoter-Polymerase Interaction Facilitates Promoter Release", the Journal of Biological Chemistry, 280(15), 14956-14961 (Apr. 15, 2005).
Heinkoff, S. and Heinkoff, J.G., "Amino acid substitution matrices from protein blocks", *PNAS*, 89(22): 10915-10919 (Nov. 15, 1992).
International Search Report completed on Feb. 6, 2014 for International Application No. PCT/SG2013/000486, entitled "Univariant Extrinsic Initiator Control System for Microbes and an In Vitro Assembly of Large Recombinant DNA Molecules From Multiple Components".
Lang, B.E. and Schwarz, F.P., "Thermodynamic dependence of DNA/DNA and DNA/RNA hybridization reactions on temperature and ionic strength", *Biophys. Chem.*, 131(1-3): 96-104 (Dec. 2007).

(Continued)

*Primary Examiner* — Nancy J Leith
(74) *Attorney, Agent, or Firm* — Hamilton, Brook, Smith & Reynolds, P.C.

(57) ABSTRACT

The invention provides, inter alia, a nucleic acid (e.g. expression vector) that comprises at least a first coding sequence and a second coding sequence. Each coding sequence is under the control of an inducible promoter of defined strength. Different promoters can have different strengths. Each promoter is responsive to the same inducer. The invention also provides: methods of expressing coding regions, methods of making a product of a multi-enzyme pathway, and methods of optimizing the yield of a product of a multi-enzyme metabolic pathway using the nucleic acids provided by the invention. Also disclosed is a method of non-enzymatic gene cloning useful for practicing the invention.

20 Claims, 31 Drawing Sheets

Specification includes a Sequence Listing.

(56)　　　　　　References Cited

OTHER PUBLICATIONS

Liu, C. et al., "Artemisinin: current state and perspectives for biotechnological production of an antimalarial drug", *Appl. Microbiol. Biotechnol.*, 72(1): 11-20 (Sep. 2006).

Marienhagen, J. et al., Phosphorothiate-based DNA recombination: an enzyme-free method for the combinatorial assembly of multiple DNA fragments, Biotechniques, 0: 1-6 (2012).

Nakamaye, K.L. et al., "Direct sequencing of polymerase chain reaction amplified DNA fragments through the incorporation of deoxynucleoside α-thiotriphsophates", *Nucleic Acids Res.*, 16 (21): 9947-9959 (1988).

Newman, J.D. et al. "High-level production of amorpha-4, 11-diene in a two-phase partitioning bioreactor of metabolically engineered *Escherichia coli*", *Biotechnol. Bioeng.*, 95(4): 684-691 (2006).

Notification Concerning Transmittal of International Preliminary Report on Patentability for International Application No. PCT/SG2013/000486, entitled "Univariant Extrinsic Initiator Control System for Microbes and an In Vitro Assembly of Large Recombinant DNA Molecules From Multiple Components" dated May 19, 2015.

Py, B. and Barras, F., "Building Fe—S proteins: bacterial strategies", *Nature Reviews Microbiology*, 8: 436-446 (Jun. 2010).

Py, B. et al., "Fe—S clusters, fragile sentinels of the cell", *Curr. Opin. Microbiol.*, 14(2): 218-223 (Apr. 2011).

Rabinowitz, J.D. and Kimball, E., "Acidic acetonitrile for cellular metabolome extraction from *Escherichia coli*", *Analytical Chemistry*, 79(16): 6167-6173 (2007).

Sayers et al., "5'—3' Exonucleases in Phosphorothioate-Basedoligonucleotide-directed mutagenesis" 16(3) Nucleic Acids Research 791-802 (Year: 1988).

Scheich et al., "Vectors for co-expression of an unrestricted number of proteins", Nucleic Acids Research 2007, 35(6), pp. 1-7.

Schlief, R., "Regulation of the L-arabinose operon of *Escherichia coli*", *Trends in Genetics*, 16(12): 559-565 (2000).

Shao, Z. et al., "DNA assembler, an in vivo genetic method for rapid construction of biochemical pathways", *Nucleic Acids Research*, 37(2): e16 (Feb. 2009).

Styczynski, M.P. et al."BLOSUM62 miscalculations improve search performance" *Nat. Biotech*, 26(3): 274-275 (2008).

Tsuruta, H. et al., High-level Production of Amorpha-4, 11-diene, a Precursor of the Antimalarial Agent Artemisinin, in *Escherichia coli, PLoS One*, 4: e4489 (Feb. 16, 2009).

Tyo, K.E. et al., "Stabilized gene duplication enables long-term selection-free heterologous pathway express", *Nat. Biotechnol.*, 27(8): 760-765 (Aug. 2009).

Xiao, Y. et al. "Retrograde Signaling by the Plastidial Metabolite MEcPP Regulates Expression of Nuclear Stress-Response Genes, " *Cell*, 149(7): 1525-1535 (Jun. 22, 2012).

Zhou, K. et al., "Metabolite Profiling Identified Methylerythritol Cyclodiphosphate Efflux as a Limiting Step in Microbial Isopronoid Production", *PLoS One*, 7: c47513 (Nov. 2, 2012).

Zhou, K et al., "Optimization of Amorphadiene Synthesis in Bacillus Subtilis Via Transcriptional, Translational, and Media Modulation", *Biotechnology and Bioengineering*, 110(9): 2556-2561 (Sep. 2013).

Final Office Action for U.S. Appl. No. 14/441,447 "Univariant Extrinsic Initiator Control System for Microbes and an In Vitro Assembly of Large Recombinant DNA Molecules From Multiple Components", dated Mar. 20, 2019.

Non-Final Office Action for U.S. Appl. No. 14/441,447 "Univariant Extrinsic Initiator Control System for Microbes and an In Vitro Assembly of Large Recombinant DNA Molecules From Multiple Components", dated Oct. 18, 2018.

Final Office Action for U.S. Appl. No. 14/441,447 "Univariant Extrinsic Initiator Control System for Microbes and an In Vitro Assembly of Large Recombinant DNA Molecules From Multiple Components", dated May 7, 2018.

Non-Final Office Action for U.S. Appl. No. 14/441,447 "Univariant Extrinsic Initiator Control System for Microbes and an In Vitro Assembly of Large Recombinant DNA Molecules From Multiple Components", dated Oct. 30, 2017.

Non-Final Office Action for U.S. Appl. No. 16/447,418, "Univariant Extrinsic Initiator Control System for Microbes and an In Vitro Assembly of Large Recombinant DNA Molecules From Multiple Components", dated Mar. 25, 2021.

Notice of Allowance for U.S. Appl. No. 16/447,418, "Univariant Extrinsic Initiator Control System for Microbes and an In Vitro Assembly of Large Recombinant DNA Molecules From Multiple Components", dated Aug. 4, 2021.

Bandwar et al. (Kinetic and Thermodynamic Basis of Promoter Strength: Multiple Steps of Transcription Initiation by T7 RNA Polymerase Are Modulated by the Promoter Sequence, Biochemistry 2002, 41, 3586-3595).

* cited by examiner

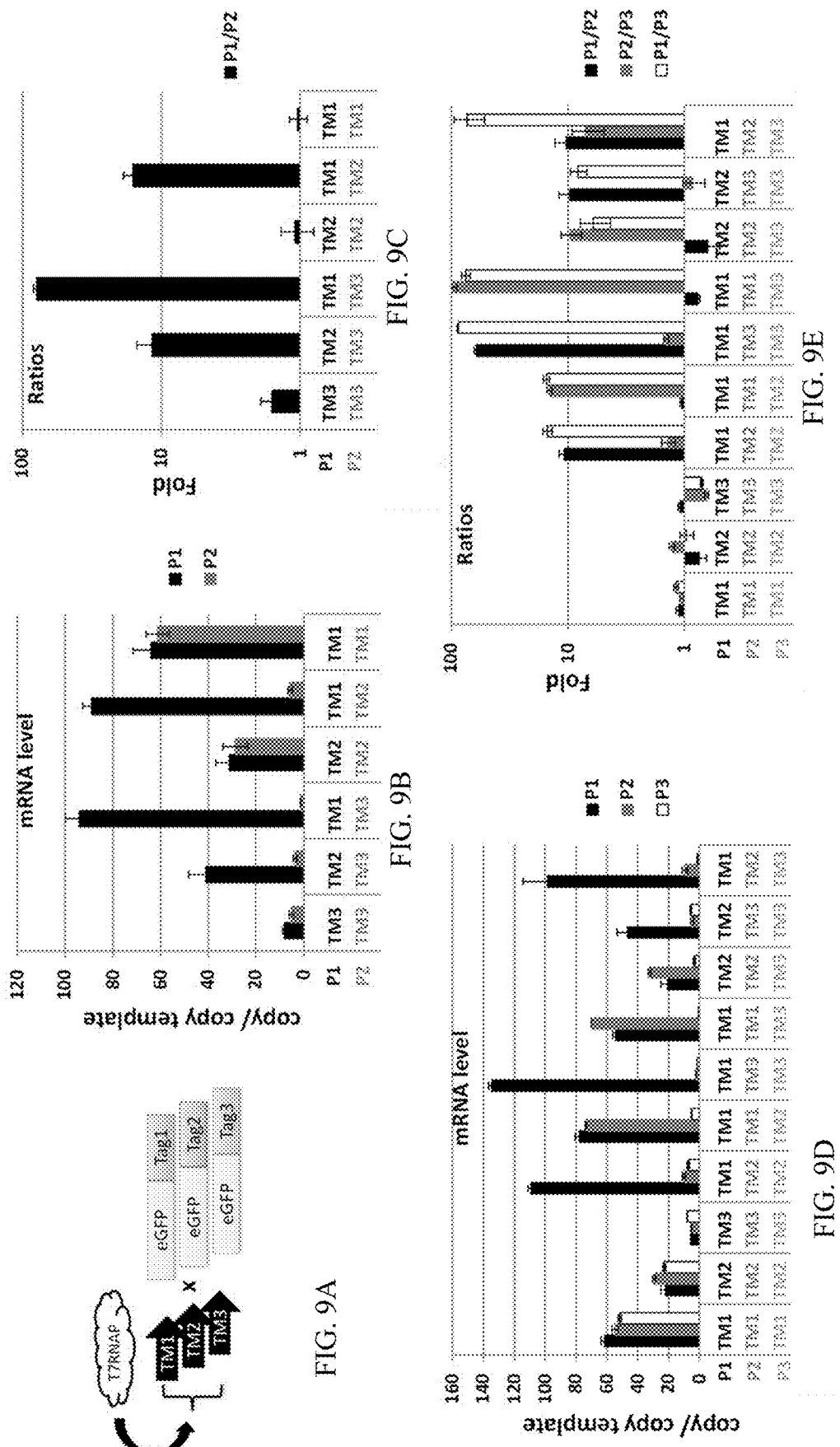

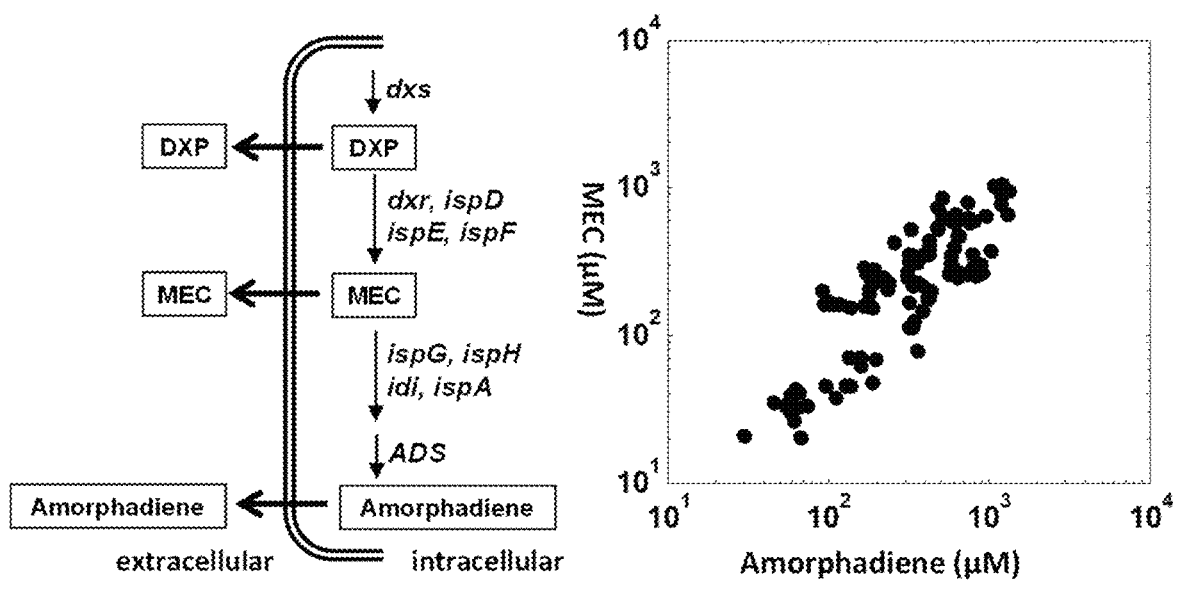
FIG. 18A                 FIG. 18B
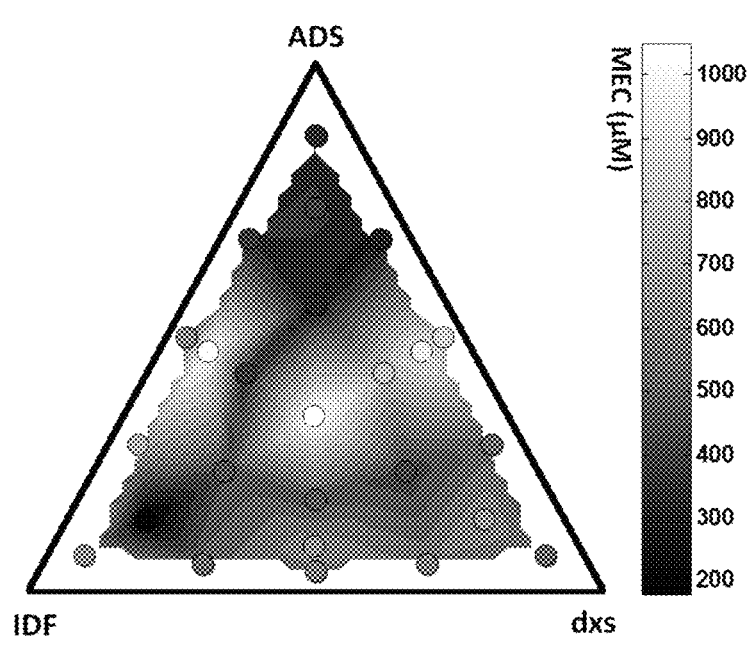
FIG. 18C

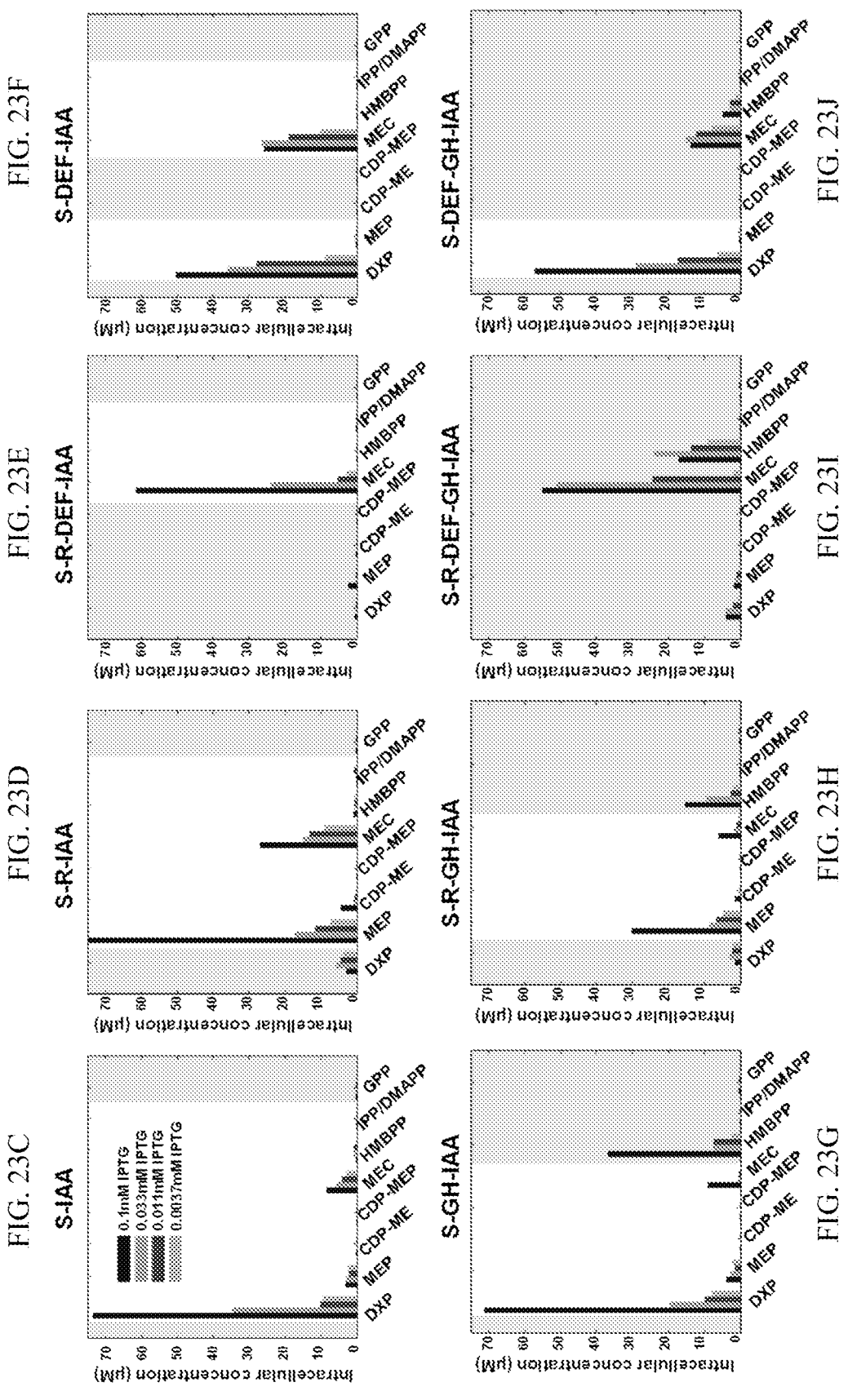

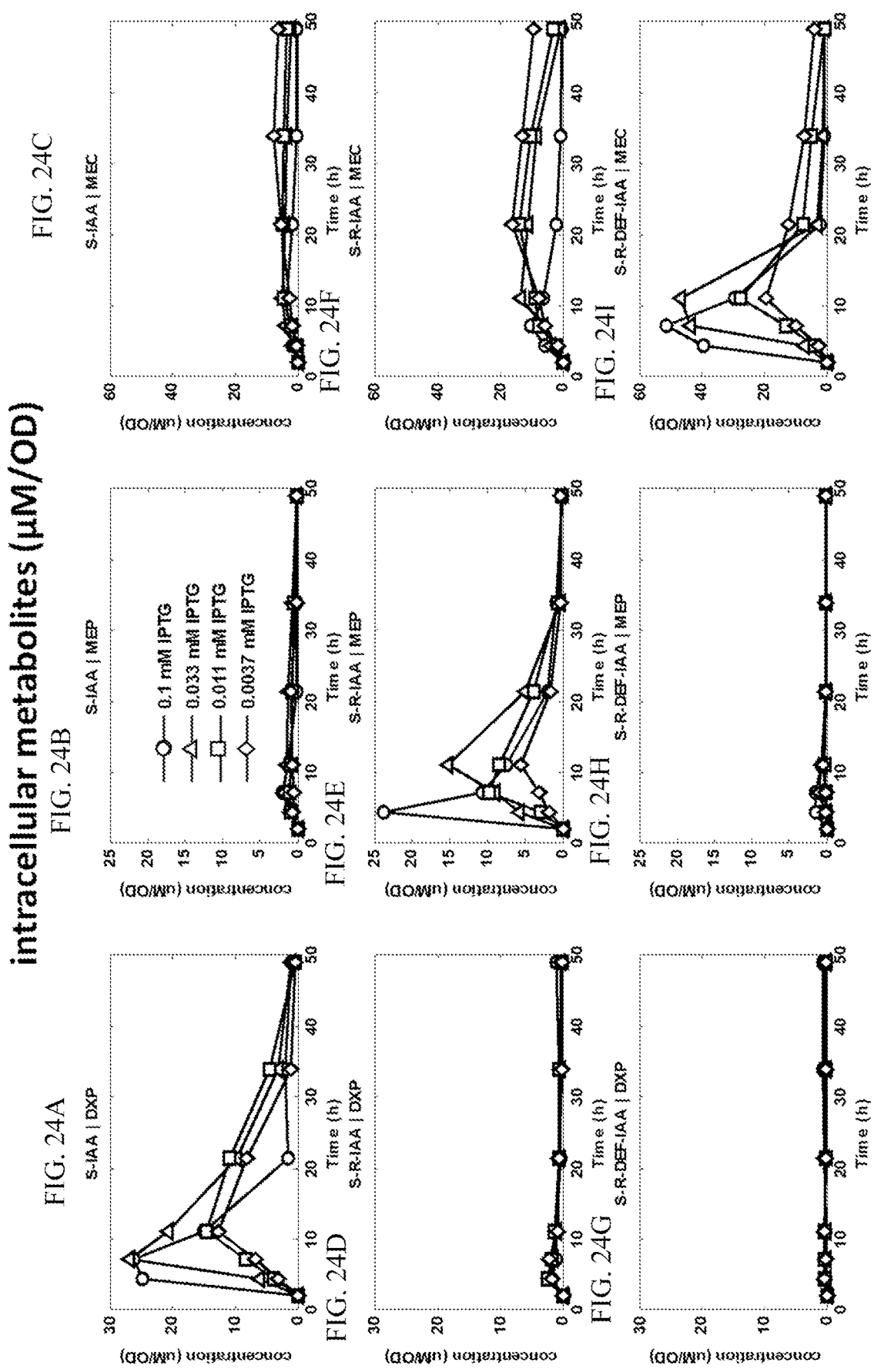

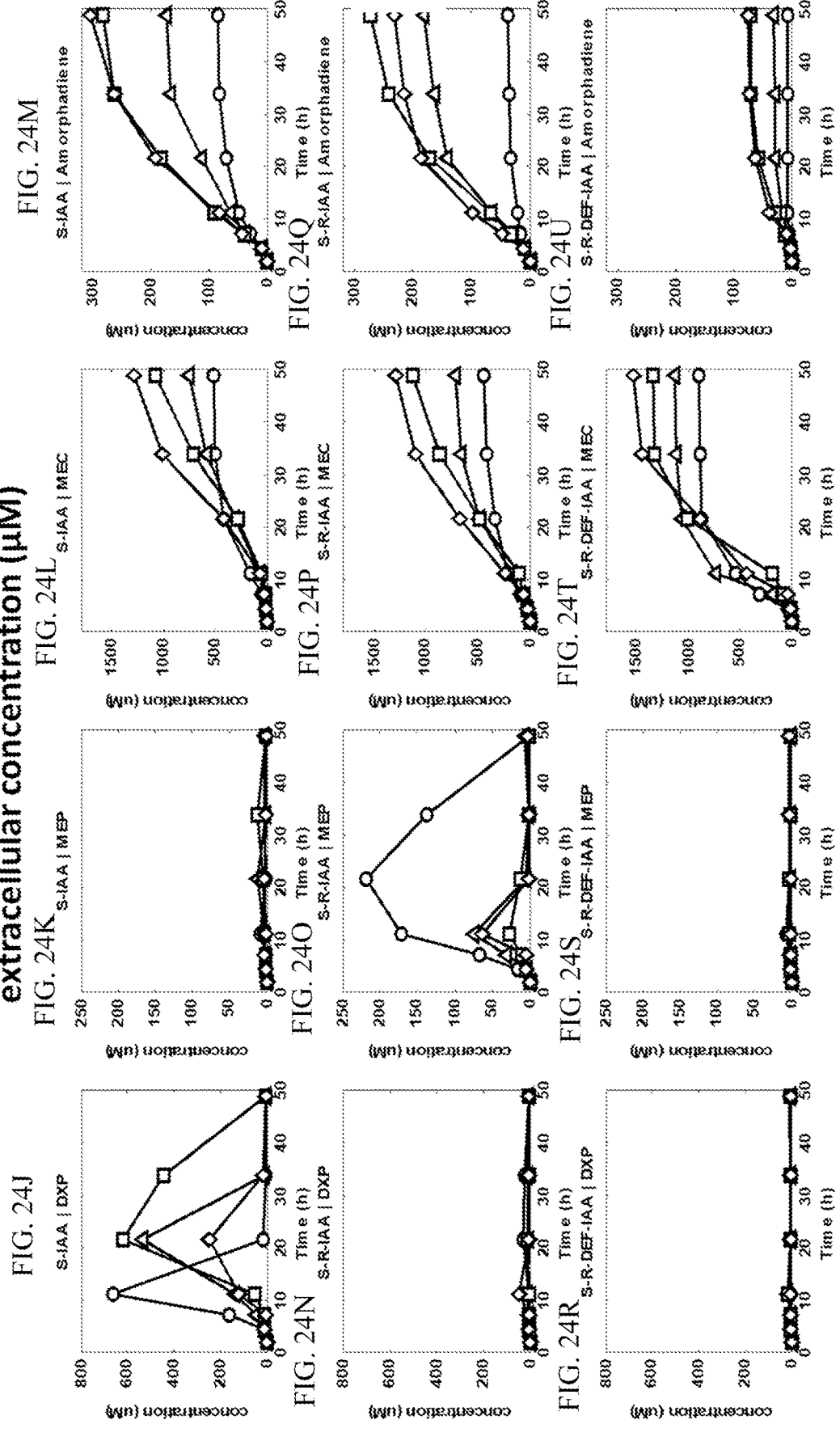

Cell density (OD600)

```
atgtctctgactgaggaaaaaccaatccgtccgatcgcaaactttcc
gccgagcatctggggtgatcagttcctgatctaccagaagcaggtcg
agcaaggcgtagaacagatcgtgaacgacctgaaaaaggaggtacgt
cagctgctgaaagaggctctggacatcccgatgaaacatgcgaacct
gctgaagctgattgatgagattcagcgcctgggtatcccataccact
tcgaacgtgaaattgatcacgcgctgcagtgtatttatgaaacgtat
ggtgataactggaacggtgaccgtagctccctgtggttccgtctgat
gcgtaagcagggttattacgtgacctgcgacgtcttcaacaactaca
aagacaagaacggcgcgtttaaacagagcctggcgaatgacgttgaa
ggcctgctggagctgtatgaagcaacctctatgcgtgttccgggcga
aatcatcctggaagatgctctgggtttcacccgttctcgcctgtcta
tcatgaccaaggacgcattttccactaacccggccctgttcaccgaa
atccagcgtgcgctgaaacagcctctgtggaagcgtctgccgcgtat
cgaggcggcacagtacatcccgttctatcagcaacaggattcccaca
acaaaaccctgctgaaactggcgaaactggaatttaacctgctgcaa
tccctgcacaaagaagaactgtctcatgtttgcaaatggtggaaagc
cttcgacatcaagaaaaacgcgccgtgcctgcgcgaccgtatcgtag
aatgctatttctggggcctgggctccggttatgagcctcaatactct
cgtgctcgcgtattcttcaccaaagcggtagctgtgatcaccctgat
cgacgatacctacgatgcttacggtacgtacgaagaactgaagattt
ttaccgaggctgttgaacgctggtctatcacttgcctggataccctg
ccggaatacatgaaaccgatctataaactgttcatggatacttatac
cgaaatggaagagttcctggcaaaagaaggtcgcactgatctgttca
actgtggcaaggagtttgtgaaagaattcgtccgcaacctgatggtg
gaggcgaagtgggcaaacgagggtcacatcccgaccaccgaagaaca
cgacccggtagttatcatcaccggtggcgcaaacctgctgactacca
cttgctacctgggtatgtccgacatttttacgaaagaaagcgttgaa
tgggcagtgtctgcgcctccgctgttccgttactctggtatcctggg
ccgtcgcctgaacgatctgatgacccataaagccgagcaggaacgta
aacactccagcagctctctggaatcttacatgaaagaatacaacgtt
aacgaagagtatgcgcagaccctgatctacaaagaggttgaggatgt
atggaaagacatcaaccgtgagtacctgactactaaaaacatcccac
gcccgctgctgatggcagtgatttatctgtgccagtttctggaagtg
cagtatgcgggcaaagataacttcacccgtatgggtgacgaatacaa
acacctgatcaagtccctgctggtttacccaatgtccatc
```

UNIVARIANT EXTRINSIC INITIATOR CONTROL SYSTEM FOR MICROBES AND AN IN VITRO ASSEMBLY OF LARGE RECOMBINANT DNA MOLECULES FROM MULTIPLE COMPONENTS

RELATED APPLICATIONS

This application is a divisional of U.S. application Ser. No. 16/447,418, filed Jun. 20, 2019, which is a divisional of U.S. application Ser. No. 14/441,447, now abandoned, filed Nov. 15, 2013, which is the U.S. National Stage of International Application No. PCT/SG2013/000486, filed Nov. 15, 2013, which designates the U.S., published in English, and claims the benefit of U.S. Provisional Application No. 61/726,795, filed on Nov. 15, 2012. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 44591056004_SEQUENCE_LISTING.txt; created Oct. 7, 2021, 25,165 Bytes in size.

BACKGROUND OF THE INVENTION

Most metabolic pathways are not restricted by a single rate-limiting step. To exploit a pathway for the production of metabolites will require the optimal expression of several enzymes in tightly coordinated manner. Failure to do so will invariably result in undue metabolic burden where metabolic imbalance can lead to the accumulation of intermediate metabolites or gene products with potential cytotoxicity or, in some cases, may affect normal cell growth. Thus, a significant challenge to produce compounds, such as pharmaceutical products or their precursors, using microbial cells as biofactories is to optimize expression of multiple enzymes participating in a certain pathway.

A number of tools are currently available to allow the fine modulation of gene expression in a pathway. This include methods for generating randomized genetic knockouts and overexpression libraries, synthetic promoter libraries, tunable intergenic regions, and global techniques (e.g., artificial transcription factor engineering, ribosome engineering, global transcription machinery engineering, and genome shuffling).

Despite the availability of these tools, simultaneous optimization of the expression of a number of genes in a pathway is still highly empirical, unpredictable and time consuming. Currently, there is no way of knowing if an optimal is achieved by tuning with the existing tools and methods, making these highly unsatisfactory. Hence, a tacit demand, yet to be met, is a reliable method to enable the tuning of the expression of multiple genes in a single cassette with predictable optima.

SUMMARY OF THE INVENTION

In one embodiment, the present invention provide expression vectors. The expression vector comprises at least a first coding region and a second coding region. The first coding region encodes at least a first gene product, the first coding region being operably linked to a first inducible promoter, the first inducible promoter being of a first strength and being responsive to an inducer. The second coding region encodes at least a second gene product, the second coding region being operably linked to a second inducible promoter, the second inducible promoter being of a second strength, different from the first strength, and being responsive to the inducer.

In another embodiment, the present invention provides kits that comprise at least two expression vectors. The first expression vector comprises a coding region encoding at least a first gene product, the coding region being operably linked to a first inducible promoter, the first inducible promoter being of a first strength and being responsive to an inducer. The second expression vector comprises a coding region encoding at least a second gene product, the coding region being operably linked to a second inducible promoter, the second inducible promoter being of a second strength, different from the first strength, and being responsive to the inducer.

In another embodiment, the present invention provides methods of expressing at least a first coding region and a second coding region in a cell. The method comprises providing an expression vector comprising at least the first coding region and the second coding region. The first coding region is operably linked to a first inducible promoter, the first inducible promoter being of a first strength and being responsive to an inducer. The second coding region is operably linked to a second inducible promoter, the second inducible promoter being of a second strength, different from the first strength, and being responsive to the inducer.

In another embodiment, the present invention provides methods of expressing at least a first coding region and a second coding region in a cell. The method comprises providing at least a first expression vector comprising at least the first coding region encoding a first gene product, and at least a second expression vector comprising at least the second coding region coding region encoding a second gene product. The first coding region is operably linked to a first inducible promoter, the first inducible promoter being of a first strength and being responsive to an inducer. The second coding region is operably linked to a second inducible promoter, the second inducible promoter being of a second strength, different from the first strength, and being responsive to the inducer.

In another embodiment, the present invention provides methods of optimizing yield of a product of a multi-step enzymatic pathway in a host cell. The multi-step enzymatic pathway including at least a first reaction catalyzed by a first enzyme, and a second reaction catalyzed by the second enzyme. The method comprises determining optimal levels of expression of the first and the second enzymes, determining the ratio of a strength of a first inducible promoter to a strength of a second inducible promoter, the ratio of the strengths corresponding to the optimal levels of expression of the first and the second enzymes, the first and the second promoters being responsive to the same inducer; and constructing an expression vector. The expression vector comprises a first coding region encoding the first enzyme, the first coding region being operably linked to the first inducible promoter, and a second coding region encoding the second enzyme, the second coding region being operably linked to the second inducible promoter.

In another embodiment, the present invention provides methods of gene cloning. The method comprises contacting each of a vector and a set of inserts, the set of inserts including at least a first coding region and a second coding region, with a pair of first terminal primers, a pair of second terminal primers, and at least one pair of linking primers.

Each of the first terminal primers includes a first region complementary to the vector and a second region complementary to a first insert in the set of inserts, each of the second terminal primers includes a first region complementary to the vector and a second region complementary to an insert different from the first insert, each of the linking primers includes a first region complementary to an insert in the set of inserts and a second region complementary to a different insert in the set of inserts. Each primer includes at least one phosphorothioate internucleotide linkage. The method further includes amplifying the vector and at least two inserts to produce a vector amplification product and at least two insert amplification products, each including at least one phosphorothioate internucleotide linkage; non-enzymatically cleaving the vector amplification product and the at least two insert amplification products at the at least one phosphorothioate internucleotide linkage to produce complementary single-stranded overhangs; annealing the vector amplification product and the at least two insert amplification products and thereby non-enzymatically assembling a transforming product; and, in some embodiments, further comprising introducing the transforming product into a host cell.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2A illustrates the decomposition method. Each module of the pathway was individually controlled by an independent tunable promoter where transcription levels were regulated by the cognate inducers. FIG. 2B illustrates the univariant controlling method. The system was regulated at two dimensions: the ratios of the pathway modules were modulated by applying different engineered promoters with various strengths and the overall expression were controlled by the master regulator that simultaneously and equally tunes the level of all promoters.

FIG. 3A illustrates cell harboring pAC-LYC (continuously expression of crtE, crtB and crtI genes) and PETK-T7-SIDF plasmids. FIG. 3B illustrates cell harboring pAC-LYC plasmid together with pETK-T7-eGFP (●) or pETK-T7-t-dxs (■) or pETK-T7-t-idi (▲) plasmid. pETK-T7-t-dxs (■) or pETK- T7-t-idi (▲) were engineered to be untranslatable into proteins. Presented data was average of triplicates with standard deviation.

FIGS. 4A-4C illustrate lycopene production response to simultaneously tuning of pBAD promoter for crtEBI module and T7, TM2 or TM3 promoter for SIDF module in BL21-Gold (DE3) strain harboring pAC-BAD-crtEBI plasmid together with pETK-T7-SIDF (FIG. 4A) or pETK-TM2-SIDF (FIG. 4B) or pETK-TM3-SIDF (FIG. 4C) plasmid. The dots indicate the lycopene yields and the surfaces were interpolated based on triangle-based cubic interpolation. The numbers in the figures indicate the highest yields achieved experimentally. FIGS. 4D-4F illustrate transcription levels of SIDF module (represented by dxs mRNA level) and crtEBI module (represented crtE mRNA level) at various induction conditions in FIGS. 4A-4C. All the transcription levels were normalized to level of cysG. The circled points indicate the highest lycopene production conditions in the surface and the squares indicate the covered expression range. FIG. 4G illustrates the combination of the highest production points and expression ranges in FIGS. 4D, 4E, and 4F.

In FIG. 6A, the fluorescence of all the conditions (IPTG, mutant promoters) were normalized to the strongest expression condition (pAC-TM1-eGFP with 0.3 mM IPTG). In FIG. 6B, the fluorescence of each plasmid with various IPTG inductions were separately normalized to the level of strongest induction (0.3 mM IPTG). For each data point, the plasmids, from left to right, are TM1, TM2, and TM3. In FIG. 6C, the fluorescence each IPTG induction for different mutant promoters were separately normalized to the level of strongest promoter (TM1 promoter). The error bars represented the standard deviation of three biological replicates. For each data set on the X-axis (in FIGS. 6B & 6C), the IPTG concentrations are from highest (0.3 mm) to lowest (0.011 mm), from left to right.

In FIG. 8A, the amorphadiene synthesis was carried out through DXP pathway: pAC-TM2-dxs-TM/3-IDF-TM2-ADS plasmid. In FIG. 8B, the amorphadiene synthesis was carried out through MVA pathway: pAC-TM3-SBR-TM2-KKDI-TM3-AA plasmid. The error bars represented the standard deviation of three biological replicates. For each data set on the X-axis, the IPTG concentrations are from highest (0.3 mm) to lowest (0.011 mm), from left to right.

FIGS. 9A-9E illustrate in vitro expression of mutant promoters with competition. FIG. 9A is an illustration of in vitro transcription experiment. The systems of two or three modules controlled by different promoters were combinatorially mixed together in equal amount for the reaction. The modules were standardized using eGFP genes with various short tags that were differentially measured by qPCR. To ensure the competition, the template concentration was adjusted to a high amount, as much as half of the concentration of T7 polymerase used. In FIGS. 9B & 9D, the transcription result of two (FIG. 9B) or three (FIG. 9C) module systems were presented as the copy of mRNA transcribed from per copy of template DNA. P1, P2 and P3 represented different modules where promoters were indicated at X axis. In FIGS. 9C & 9E, the ratio of the transcription levels between modules where promoters were indicated at the X axis. The error bars represented the standard deviation of four replicates.

FIG. 11A illustrates lycopene production at all conditions. The combination of pathway modules (SIDF: top; crtEBI: bottom) were presented at X axis and the IPTG concentrations were presented as different bars. For each data set on the X-axis, the IPTG concentrations are from highest (0.3 mm) to lowest (0.011 mm), from left to right. FIG. 11B illustrates lycopene production response to the expression levels of two modules. FIG. 11C illustrates lycopene production response to the combination of mutant promoters for two modules. Only the optimum lycopene yields at various IPTG concentrations were presented. The color of the dots indicates the lycopene yields.

FIGS. 12A & 12B illustrate the initial screening experiment. FIGS. 12C & 12D illustrate the focused experiment. The color dots indicated the experimental conditions and the crosses indicate the conditions that were unnecessary to test further after initial screening study. The color of the dots indicated the lycopene yields. FIGS. 12A & 12C illustrate lycopene production response and the expression levels of the two modules. FIGS. 12B & 12D illustrate lycopene production response to the combination of two modules using mutant promoters. The color of the dots indicated the lycopene yields.

FIG. 13B: MG1655 DE3 strain, DXP pathway, and FIG. 13C: MG1655 DE3 strain, MVA pathway. The combination of pathway modules were presented at X axis and the IPTG concentrations were presented as different bars. For each data set on the X-axis, the IPTG concentrations are from highest (0.3 mm) to lowest (0.011 mm), from left to right.

FIGS. 15A & 15C illustrate amorphadiene production in BL21 Gold-DE3 (FIG. 15A) or MG1655 DE3 (FIG. 15C) strains response to the relative expression level (a.u.) of three modules calculated by "Equation 1". The color of the dots indicated the lycopene yields. The high production conditions (more than 50% of the maximum yield) are presented in (FIG. 15B) for Bl21-Gold DE3 strain and (FIG. 15D) for MG1655 DE3 strain.

FIG. 16A: BL21-Gold DE3 strain, DXP pathway; FIG. 16B: MG1655 DE3 strain, DXP pathway; and FIG. 16C: MG1655 DE3 strain, MVA pathway. The percentage of each module was calculated based on "Equation 1". Only the optimum amorphadiene yields at various IPTG concentrations were presented at each point and the color of the dots indicate the response yield.

FIG. 17A is an illustration of a ternary plot. Each species (FIG. 17A, 17B, or 17C) is 100% at the corner of the equilateral triangle and every point represents a different composition of the three components. By drawing parallel lines along the borders, the percentage of each species is equal to the length of the line aiming at the opposite border. FIG. 17B is an illustration of the rational optimization process. The red cycled points indicated the initial screening experimental conditions which separated the space into six regions (I, II, III, IV, V, and VI). Based on the yields at various points, the follow-up focused experiments were then carried out at selected region or regions defined by dashed lines in FIGS. 17C & 17D. FIGS. 17C & 17D are ternary plots of three modules in BL21-Gold DE3 (FIG. 17C) or MG1655 DE3 (FIG. 17D) strain. The percentage of each module was calculated based on "Equation 1". Only the optimum amorphadiene yields at various IPTG concentrations were presented at each point and the color of the dots indicate the yield. The regions defined by gray area indicate the focused conditions resulting from the initial screening study.

FIGS. 18A-18C illustrate extracellular metabolites accumulation. Extracellularly accumulated metabolites of DXP pathway were measured for BL21-Gold DE3 strain in conditions same as amorphadiene production optimization through DXP pathway. In FIG. 18A, efflux of DXP pathway intermediates into the growth medium. DXP (1-Deoxy-D-xylulose 5-phosphate) and MEC ((E)-4-Hydroxy-3-methyl-but-2-enyl pyrophosphate) were found highly accumulated in the medium. FIG. 18B illustrates the correlation between amorphadiene and extracellular MEC. All the conditions were presented. FIG. 18C is a ternary plot representation of the extracellular MEC concentrations responded to the ratios of pathway modules'. Only the optimum amorphadiene yields at various IPTG concentrations were presented at each point and the color of the dots indicate the response yield.

FIG. 20A is an illustration of the design at one junction between two modules (black and gray). The cross-lapping primer consists of gene specific sequence (GSS) and tag sequence complementary to adjacent primer's GSS. The phosphorothioate modifications were indicated as cycles. An "Ox/y" designation was used to define the primers, where O denoted overlap; x was the length of overlap which had one modification at each y base pairs of the sequence. FIG. 20B is an illustration of assembling of multiple DNA modules into one plasmid.

FIG. 21A illustrates optimization of cations using the assembly of PAC-SIDF plasmid with O12-13/4-5 design (12-13 bases overlap with modification at every 4-5 bases). FIG. 21B illustrates the transformation efficiency of PAC-SIDF plasmid in the presence of MgCl2. FIG. 21C illustrates the effect of the phosphorothioate modification frequency on the assembly efficiency. O12-13/4-5, O12-13/6-7, O12-13/12-13 designs: 12-13 bases overlap with modification at every 4-5 bases, 6-7 bases or 12-13 bases. FIG. 21D illustrates the effect of overlap length on the assembly efficiency. O12-13/4-5, O24-25/4-5, O36-38/4-5 designs: 12-13 bases, 24-25 bases, 36-38 bases overlap with modification at every 4-5 bases. All the experiments were done at triplicates and the standard errors were shown in the figure.

FIG. 22A illustrates the dxp pathway and Fe—S cluster assembling pathway. GA3P: glyceraldehyde 3-phosphate, DXP: 1-deoxy-D-xylulose 5-phosphate, MEP: 2C-methyl-D-erythritol 4-phosphate, CDP-ME: 4-diphosphocytidyl-2C-methyl D-erythritol, CDP-MEP: 4-diphosphocytidyl-2C-methyl D-erythritol 2-phosphate, MEC: 2C-methyl-D-erythritol 2,4-diphosphate, HMBPP: hydroxylmethylbutenyl diphosphate, IPP: Isopentenyl pyrophosphate, DMAPP: Dimethylallyl pyrophosphate, GPP: Geranyl diphosphate, FPP: Farnesyl diphosphate, GGPP: Geranylgeranyl diphosphate. FIG. 22B is an illustration of various modules assembled in the project (correlated to Table 7). CAM: chloramphenicol resistance gene, p15A-ori: p15A original of replication.

FIGS. 23A-23J illustrate the performance of different combinations of DXP pathway genes in *E. coli*. FIG. 23A illustrates 48 h amorphadiene yield. Different concentrations of IPTG were represented by bars with different colors. The experiment was repeated four times and the standard errors were shown. FIG. 23B illustrates the correlation of pathway modules with amorphadiene yield at optimal IPTG inductions. FIGS. 23C-23J illustrate early response of intracellular metabolites at 3 h after induction. The gray areas indicated the overexpressed section of DXP pathway. The experiment was repeated twice and the averages were shown.

FIGS. 24A-24X illustrate the kinetics of S-IAA-PAC, S-R-IAA-PAC and S-R-DEF-IAA-PAC strains. FIGS. 24A-24I illustrate the specific concentration ($\mu$M/OD) of intracellular metabolites: DXP, MEP and MEC. The rest of the metabolites were accumulated at concentrations lesser than 2 $\mu$M/OD and were neglected. FIGS. 24J-24U illustrate the concentration of extracellular metabolites: DXP, MEP, MEC and amorphadiene. The rest of the metabolites were accumulated at concentrations lesser than 50 $\mu$M and were neglected. FIGS. 24V-24X illustrate the cell density.

FIG. 28 is the sequence of codon optimized ADS gene, SEQ ID NO: 29.

DETAILED DESCRIPTION OF THE INVENTION

Figure 1:
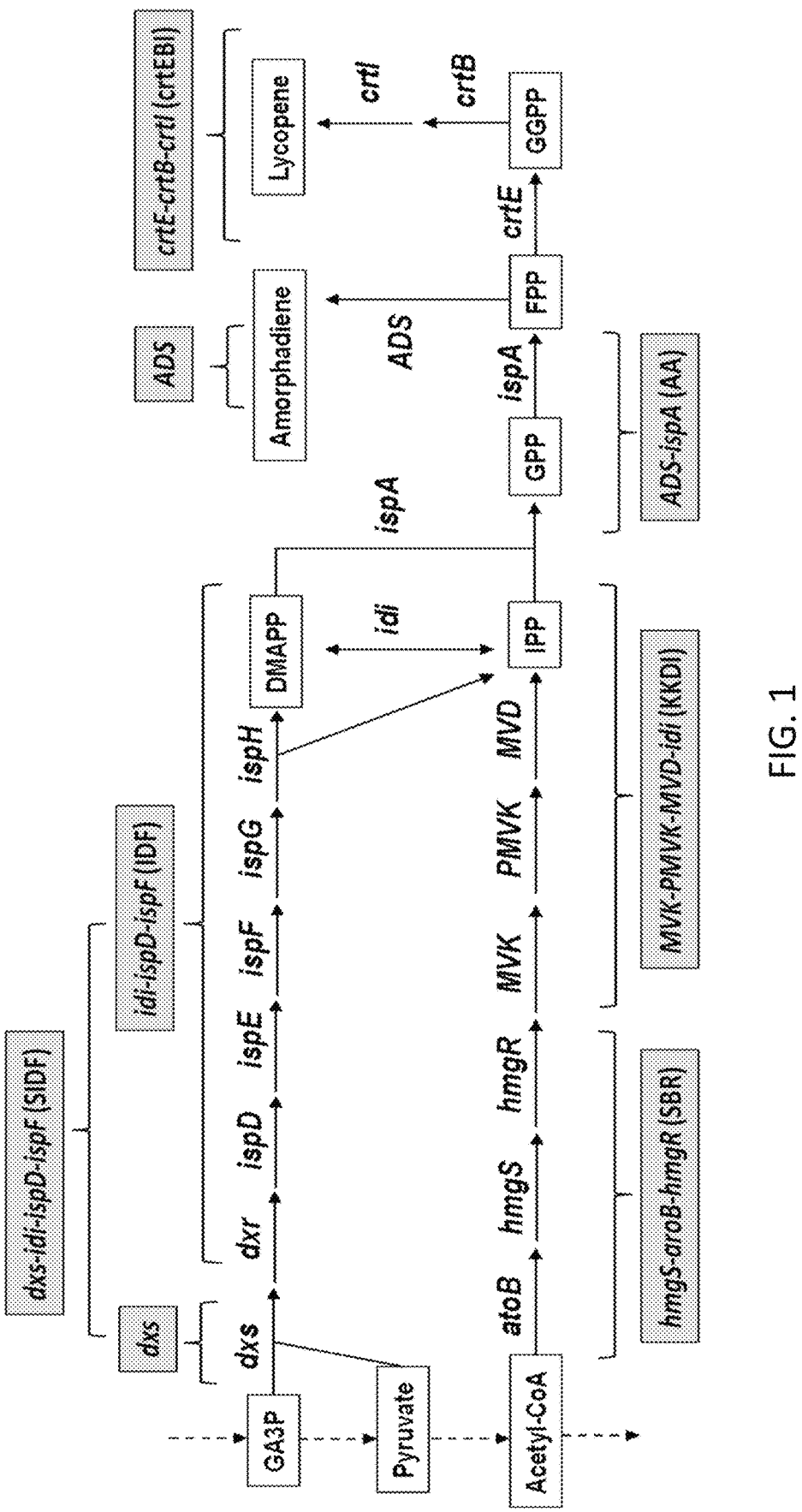
FIG. 1 illustrates isoprenoid production pathways. Pathways for the production of isoprenoid (Amorphadiene or Lycopene): the DXP pathway (top row; dxs to idi), MVA pathway (bottom row, from hmgS to MVD), terpenoid synthesis pathway (ADS, crtE, crtI, crtB) and other *E. coli* native genes (remaining genes). A solid arrow represents a single enzymatic step, while a dashed arrow represents multiple enzymatic steps. The overexpressed pathway modules are listed in boxes (SIDF, ADS, crtEBI, SBR, KKDJ, AA). Key metabolites are with white boxes. Abbreviations for metabolites: GA3P: glyceraldehyde 3-phosphate, IPP: Isopentenyl pyrophosphate, DMAPP: Dimethylallyl pyrophosphate, GPP: Geranyl diphosphate, FPP: Farnesyl diphosphate, GGPP: Geranylgeranyl diphosphate.

In order to simultaneously control a number of promoters with different strengths, there is a need for the use of a single resource (inducer and transcribers/polymerases) that can modulate these promoters for the expression of multiple down-stream genes. These promoters are herein referred to as 'dependent promoters', as they all are dependent on the same externally controlled resource for functions. If there is any perturbation in the availability of the resource, the expressions from each of this dependent promoter should change accordingly and expression of down-stream coding regions (e.g., genes) should change in fixed proportions based on the strength of the promoters. In addition, by tuning the availability of the resource, all these promoters with the same control mechanism should behave similarly, providing another layer of systematic control—the overall expression level.

μ-UNeICS

This application described the development of a novel tool (μ-UNeICS) using a plethora of currently available methods for the co-expression of multiple enzymes (coding regions, in general) in pathways controlled by a single heterologous/extrinsic transcriber. The result of which is the retention of a constant ratio of expressions when a single type (univariant) of extrinsic transcriber is distributed over multiple promoters of different strengths and all the promoters response accordingly to induction no matter if and when competition for resources exist. The performance of the expression system is well controlled and can be predicted with a simple model. This systematic method allows unprecedented control of a wide dynamic range and the rapid identification of the optimal combinations of fixed ratio of promoter-driven expressions. Furthermore, by gaining insightful understanding of the pathways, a rational optimization process can be applied to efficiently identify the global optimum. The utility of this method is in industries such as energy, health (pharmaceuticals) and environment by manipulating genetic and metabolic pathways (synthetic biology, metabolic engineering). Advantageously, identification of the optimal combinations of the fixed ratio of promoter-driven expressions, saves labor, time and experimental resources. Through this effort, previously unpredicted combinations of some isoprenoid genes were rapidly determined to result in the generation of high producing strains.

In a first aspect, the invention provides isolated nucleic acids (e.g. vectors) containing a first coding region and a second coding region. The first coding region encodes at least a first gene product, where the first coding region is operably linked to a first inducible promoter, the first inducible promoter being of a first strength and being responsive to an inducer. Similarly, the second coding region encodes at least a second gene product, where the second coding region is operably linked to a second inducible promoter, the second inducible promoter being of a second strength, different from the first strength, and being responsive to the inducer. In other embodiments, the invention provides collections of isolated nucleic acids, e.g., kits of two or more vectors, analogous to the single nucleic acid embodiment described above except where the two coding regions and their respective promoters are on different vectors in the kit.

A "coding region" is a nucleic acid comprising a sequence encoding a protein. A coding region may include one or more coding regions, including, for example, a multi-gene polycistron, such as an operon, from any source-either synthetic or naturally occurring. The coding region can comprise any protein, such as a cytokine, a growth factor, an enzyme, an antibody (or antibody mimetic), a receptor, or a structural protein. In certain embodiments, the coding region comprises an enzyme.

A coding region and a promoter, such as an inducible promoter, are "operably linked" when the promoter can modulate the transcription of the coding region, under appropriate conditions. In some embodiments, two sequences can be in operative association, and additional sequence elements such as enhancers or promoters may be present in the construct. For example, in certain embodiments, the polycistron includes ribosome binding sites in between open reading frames.

An "inducible promoter" is a promoter region whose activity can be modulated in trans by an inducer and includes promoters subject to either direct or indirect modulation by the inducer. Modulation can include, for example, direct activation (adding an inducer permits an element needed for transcription to function) or direct derepression (adding an inducer removes an element that is inhibiting normal transcription). Indirect activation (or depression) can include modulating the transcription of another agent that modulates transcription of a coding region. The present invention illustrates this later example by employing variant IPTG-inducible T7 polymerase promoters on the coding regions of interest, while expressing the T7 polymerase from another IPTG-inducible promoter, thereby directly and indirectly inducing the coding region of interest. Other promoters and agents can be used analogously, consonant with the present invention. Exemplary promoters for use in the invention include BAD (arabinose inducible; see e.g. Schlief, R. *Trends in Genetics* 16(12): 559-565 (2000)), lac, Tet, RNA polymerase promoters (T7, T3, or SP6), any kind of engineered promoter in operative association with operon(s) that makes it inducible, and combinations of any of the foregoing. In particular embodiments, the promoters include T7 family members, such as any one of SEQ ID NOs: 1-12. In more particular embodiments, the promoters include SEQ ID NO: 3 (also called TM1, herein), SEQ ID NO: 7 (TM2, herein), and SEQ ID NO: 9 (TM3, herein). The polymerase binding and the melting/initiation regions of an RNA polymerase are exemplified by nucleotides 8 to 19 and 20 to 28 of SEQ ID NO: 1, respectively. Promoters of different strength, based on the T7 promoter are exemplified by SEQ ID NOs: 1-12. Promoters of varying strength can be produced from other promoters analogously to the above examples for T7.

In certain embodiments, inducible promoters for use in the present invention are coupled to heterologous coding sequences—i.e., the combination of promoter and coding sequence is a product of man that is not naturally occurring.

Plasmids provided by the invention can be for exogenous maintenance as a nucleic acid(s) separate from a host genome or, in other embodiments, for integration into the host's genome. Plasmids can be single copy, low copy (e.g. less than 10 copies per cell, such as about: 2, 3, 4, 5, 6, 7, 8, or 9 copies per cell) or high copy (e.g. more than 10 copies per cell, such as about: 10, 15, 20, 25, 30, 35, 40, 50, 60, 70, 80, 90, or 100 copies per cell, or more).

In some embodiments, the multi-step enzymatic pathway is an isoprenoid production pathway. In more particular embodiments, the isoprenoid is a lycopene or amorphadiene. The multistep pathway can be either the DXP or MVA pathway. See FIGS. 1, 22B In particular embodiments, the coding region includes one or more genes selected from dxs (see, e.g., *E. coli* GeneID No. 945060), idi (see, e.g., *E. coli* GeneID No. 949020), ispA (see, e.g., *E. coli* GeneID No. 945064), ispD (see, e.g., *E. coli* GeneID No. 948269), ispF (see, e.g., *E. coli* GeneID No. 945057), crtE (see, e.g., *Pantoea agglomerans* phytoene synthase ACCESSION No. M38424.1), crtB (see, e.g., *Pantoea agglomerans* prephytoene pyrophosphate synthase ACCESSION No. M38423.1), crtI (see, e.g., *Pantoea agglomerans* phytoene dehydrogenase ACCESSION No. M38423.1), ADS (see, e.g., SEQ ID NO: 29, see also protein sequence AAF98444.1), hmgS (see, e.g., *Saccharomyces cerevisiae* GeneID No. 854913), atoB (see, e.g., *E. coli* GeneID No. 946727), hmgR (see, e.g., *Saccharomyces cerevisiae* GeneID No. 854900), MVK (see, e.g., *Saccharomyces cerevisiae* GeneID No. 855248), PMVK (see, e.g., *E. coli* GeneID No. *Saccharomyces cerevisiae* GeneID No. 855260), MVD (see, e.g., *Saccharomyces cerevisiae* GeneID No. 855779), Isc operon (iron-sulfur cluster, or a portion thereof), Suf operon (sulfur mobilization operon, or a portion thereof) or a combination of the forgoing. In a related aspect, the invention provides an isolated nucleic acid comprising, consisting essentially of, or consisting of SEQ ID NO: 29, or a biologically active fragment thereof.

Homologs or substantially similar peptide sequences to any of the foregoing proteins can be used in the invention. "Similar peptide sequences" can be naturally occurring (e.g., allelic variants or homologous sequences from other species) or engineered variants to the above reference sequences and will exhibit substantially the same biological function and/or will be at least about 60, 65, 70, 75, 80, 85, 90, 95, 96, 97, 98, 99% or more homologous (i.e., conservative substitutions (see, e.g., Heinkoff and Heinkoff *PNAS* 89 (22): 10915-10919 (1992) and Styczynski et al., *Nat. Biotech.* 26 (3): 274-275 (BLOSUM, e.g., BLOSUM 45, 62 or 80) or Dayhoff et al., *Atlas of protein sequence and structure* (volume 5, supplement 3 ed.). Nat. Biomed. Res. Found. pp. 345-358 (PAM, e.g., PAM 30 or 70)) or identical at the amino acid level, e.g., over a length of at least about 10, 20, 40, 60, 80, 100, 150, 200 or more amino acids or over the entire length of the mature reference peptide sequence.

In particular embodiments, the coding region of a plasmid provided by the invention includes: dxs, idi, ispD, and ispF (siDF); crtE, crtB, and crtI (crtEBI); dxs; idi, ispD, and ispF (iDF); ADS; hmgS, aroB, and hmgR (SBR); MVK, PMVK, MVD, and idi (KKDI); ADS and ispA (AA); or a combination thereof. In more particular embodiments, the plasmids provided by the invention include any of those described in Tables 2 or 7.

Any suitable cell can be a host cell transfected with a nucleic acid (e.g., vector) provided by the invention. In particular embodiments, the cell is a bacterium, a yeast cell, an insect cell, or a mammalian cell. In more particular embodiments, the cell is a bacterium, such as *E. coli*, and in more particular embodiments, the *E. coli* is selected from Exl-10-gold, DH10B, or K12 (including MG1655, such as MG1655 DE3). In certain embodiments, the cell comprises a functional lacI gene and in more particular embodiments, the cell expresses a polymerase (such as a T7 polymerase) from a lac promoter, more particularly a lacI-repressible lac promoter. In particular embodiments, the cell (e.g., a bacterium, such as *E. coli*) comprises one or more nucleic acids comprising: TM3-SBR-TM2-KKDI-TM3-AA (e.g. in plasmid pAC); TM3-siDF (e.g. in pETK); TM2-crtEBI (e.g. in pAC); or a combination thereof, such as TM3-siDF (e.g. in pETK) and TM2-crtEBI; TM2-SBR-TM1-KKDI-TM3-AA (e.g. in plasmid pAC); TM1-dxs-TM2-IDF-TM1-AA (e.g. in plasmid pAC); TM2-dxs-TM3-IDF-TM2-AA (e.g. in plasmid pAC); TM3-siDF (e.g. in pETK); and TM1-crtEBI.

In related aspects, the invention provides methods of: expressing one or more coding regions (e.g., by providing a host cell comprising one or more vectors provided by the invention, contacting the cell with the inducer under conditions to express the one or more coding regions), making a product of a multi-step enzymatic pathway (e.g. by providing a host cell comprising one or more vectors provided by the invention, contacting the cell with the inducer under conditions to express the one or more coding regions, and detecting and/or isolating the product of the multi-step enzymatic pathway—such as lycopene or amorphadiene), as well as methods of optimizing the yield of a product of a multi-step enzymatic pathway (for example, by determining optimal levels of at least first and second coding regions—e.g., enzymes—in the pathway, determining the ratio of strengths of inducible promoters for the coding regions and then providing one or more expression vectors provided by the invention with the coding regions operably linked to inducible promotes of suitable strengths).

Optimal levels of expression for a given system can be determined by any means. In certain embodiments, the levels are determined according to Equation 1, below, or an analogous equation (for example, replacing IPTG induction strength, with simply induction strength, and mutant promoter strength with simply promoter strength, et cetera) depending on the particular system employed. In some embodiments, various permutations of coding regions and promoters are screened and an output, such as a pathway product, is measured to identify an optimum under given conditions (e.g., culture conditions). In other embodiments, the system can be modeled computationally, e.g., using analytical, numerical, and/or computer-learning modalities. In still other embodiments, a system can be both modeled and screened. The starting point for any screening or modeling can, in some embodiments, be rationally designed and iteratively modified based on the results of modeling and/or screening (e.g. modeling after screening, or vice versa, as well as iteratively screened or modeled with finer resolution at each iteration). Optima for a given pathway can vary between organisms or strains of an organism based on, inter alia, cell genotypes, culture conditions, et cetera.

As a proof-of-concept, this examples below demonstrate how "UNivariant extrinsic Initiator Control System for microbes (μ-UNeICS)" was applied in the production of isoprenoids (terpenoids), which are a large family of natural compounds that can be used as fragrances, insecticides, nutraceuticals and pharmaceuticals. This systematic approach is extendable to system with, e.g., four or even more modules and applicable to all processes involving the modulation of multiple recombinant DNAs in microbes for any purpose.

CLIVA

Figures 20A, 20B:
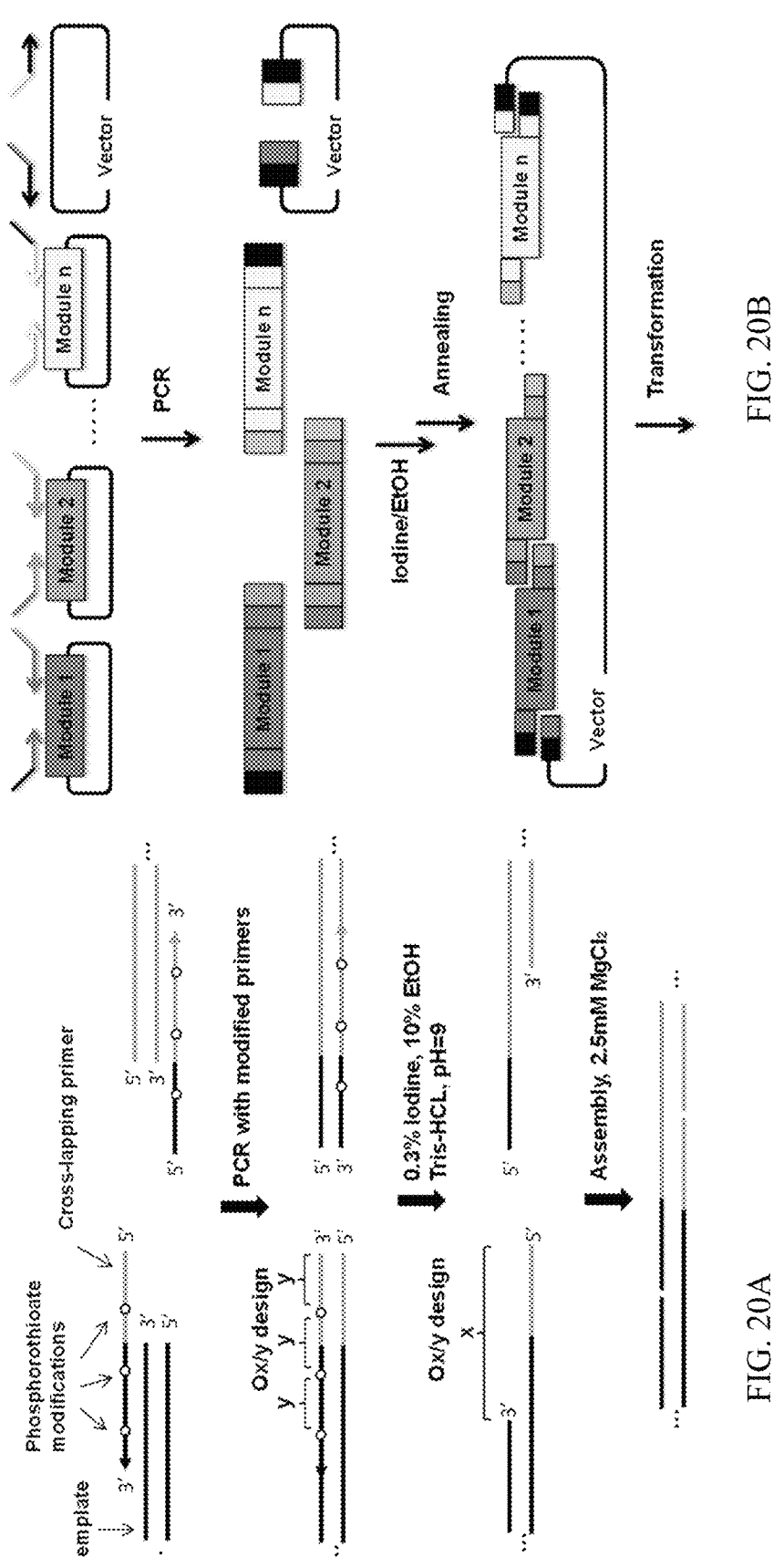
FIGS. 20A-20B illustrate the cross-lapping in vitro assembly (CLIVA) method.

In another aspect, the invention provides methods of nucleic acid assembly, such as gene cloning, which is termed CLIVA (Cross-lapping In Vitro Assembly), herein. In these methods provided by the invention, a first nucleic acid, such as a coding region is joined to at least a second nucleic acid, such as a vector, by virtue of complementary sticky ends between the first and second nucleic acids. In particular embodiments, the sticky ends are created and, optionally, hybridized, non-enzymatically, e.g., without a nuclease or a ligase. Instead, the nucleic acids are cleaved (using iodine in an ethanolic solution) at phosphorothioate modifications in the nucleic acid backbone of each nucleic acid to be joined. This process is illustrated in FIGS. 20A-20B. These methods can further include a step of transforming a cell with the joined first and second nucleic acids.

Briefly, these methods, in certain embodiments, employ an amplification step with a pair of primers for each nucleic acid to be joined. Each primer in a pair has at least two regions: a "primer region", generally at the 3' end of the primer and a "homologous sequence", generally at the 5' end of the primer. A "primer region" comprises a conventional polymerase chain reaction (PCR) primer for amplifying the nucleic acid to which it hybridizes (e.g. a first sequence). A "homologous region", in turn, comprises a sequence that can hybridize to another sequence—the sequence to which the first sequence is to be joined. For example, in some embodiments, a homologous region can hybridize to a sequence within (or comprising) the primer region of another primer. Following amplification with this primer pair, the amplified nucleic acid includes the first sequence and two homologous regions—where at least one strand of each homologous region comprises at least one phosphorothioate linkage. Following cleavage of the phosphorothioate linkage, complementary single-stranded sticky ends (overhangs) are generated—two sicky ends per amplified nucleic acid. Following this basic design scheme, numerous fragments can be joined together, such as at least 2 (e.g. a nucleic acid of interest and a vector), or 3, 4, 5, 6, 7, 8, 9, 10, 12, 13, 14, 15 nucleic acids, or more.

Primer regions will be designed according to standard practices for PCR primer design, taking into account the complexity of the nucleic acid mixture, desired melting temperature, secondary structure, dimerization, et cetera. Homologous sequences can be designed according to the particular construct to be generated. Typically, homologous sequences will have a length after cleavage of the phosphotioate modification such that the single-stranded overhangs are at least about: 12, 13, 14, 15, 16, 17, 18, 19, 20, 25, 30, or 35 nucleotides in length, or more. In particular embodiments, the single-stranded overhangs are about 32-42 nucleotides, more particularly about 36-38 nucleotides.

Sequences that will hybridize (e.g., overhangs) can comprise both primer region sequences and homologous sequences.

Primers can have varying densities of phosphorothioate modifications. Typically, the first phosphorothioate modification is at about: the $2^{nd}$, $3^{rd}$, $4^{th}$, $5^{th}$, or $6^{th}$ nucleotide, from the 3' end of the primer. In more particular embodiments, the first phosphorothioate modification is at the $3^{rd}$, $4^{th}$, or $5^{th}$ nucleotide, from the 3' end of the primer. The phosphorothioate modifications can be repeated each about: 3, 4, 5, 6, 7, 8, 9, 10, 11, 12, 13, 14, or 15 bases. In certain embodiments, the phosphorothioate modifications are repeated every about: 12-13 bases, 6-7 bases, or 4-5 bases. In more particular embodiments, the phosphorothioate modifications are repeated every 4-5 bases. Phosphorothioate modifications can be in the primer region or in the homologous sequence or both in the primer region and in the homologous sequence. From 5' to 3', the last phosphorothioate modification typically needs to be at the last bases of the homologous sequence.

Following the methods provided by the invention, numerous fragments can be assembled in an "annealing reaction" where amplified nucleic acids with complementary sticky ends are allowed to hybridize via the sticky ends. In certain embodiments, the annealed nucleic acids can be used as-is, e.g., to transform a cell without further purification, for examples, without a ligation reaction—although, in certain embodiments, the assembled nucleic acids can be purified and, optionally, ligated.

In some embodiments, at least 2, 3, 4, 5, 6, 7, 8, 9, 10, 15, 20, 25, or 30 nucleic acids, or more (e.g. 40, 50, 60, 70, 80, 90, or more) can be assembled in a single reaction. The final assembled product (e.g. a collection of inserts for a plasmid) can be at least about: 8, 10, 12, 14, 15, 16, 18, 20, 25, 30, 35, 40, 45, or 50 kb, or more, e.g., in particular embodiments, about 8 kb to about 22 kb. Advantageously, the methods provided by the invention allow the nucleic acids to be assembled quickly, for example in about: 12, 18, 24, 30, 36, 42, 48, 54, or 60 hours—e.g., in some embodiments, about 1-2 days, as compared to one to two weeks, or more, using conventional methods.

The annealing of nucleic acid fragments to be joined by the methods provided by the invention typically takes place in the presence of one or more cations. In more particular embodiments, the one or more cations are divalent cations (e.g. $Mg^{2+}$, $Ca^{2+}$, $Co^{2+}$, or $Cu^{2+}$). In still more particular embodiments, the divalent cation is $Mg^{2+}$, $Ca^{2+}$, or a combination thereof. In particular embodiments, the divalent cation is present in the annealing reaction at a concentration of about 0.5 to about: 10.0, 20.0, 30.0, 40.0, 50.0, or 60.0 mM; in more particular embodiments about: 1.0, 2.0, 2.5, 3.0, 3.5, 4.0, 4.5, 5.0, 7.5, 10.0, 12.5, 15.0, 17.5 mM. In more particular embodiments, the divalent cation is present at a concentration of about 2.5 to about 12.5 mM.

EXEMPLIFICATION

Example I: UNivariant Extrinsic Initiator Control System for Microbes (μ-UNeICS)

Background and Motivation

It is now known that most metabolic pathways are not restricted by a single rate-limiting step. The exploitation of the pathway for the production of metabolites will require the optimal expression of several native and/or heterologous enzymes in tightly coordinated manner. Failure to do so will invariably result in undue metabolic burden where metabolic imbalance can lead to the accumulation of intermediate metabolites or gene products with potential cytotoxicity or, in some cases, may affect normal cell growth. Besides, the stress caused by the overexpression of enzymes (proteins) which can be insoluble will induce the selection of low producers during fermentations. Thus, a significant challenge of using microbial cells as biofactories is to optimally balance the expressions of number of enzymes in a pathway where multivariate optimization is necessary.

A number of tools are currently available to allow the fine modulation of gene expression in a pathway. This include methods for generating randomized genetic knockouts and overexpression libraries, synthetic promoter libraries, tunable intergenic regions, and global techniques (e.g., artificial transcription factor engineering, ribosome engineering, global transcription machinery engineering, and genome shuffling).

Promoters, both constitutive and inducible, have long been used to control gene expressions. The genetic engineering of promoters of various strengths has produced large libraries which have been used predominately to precisely control the expression of a single or small number of genes.

To differentially control a large number of genes, it is common to use multiple promoters with different strengths combined with various genetic carriers such as plasmids of different copy numbers. A distinct disadvantage of this approach is that there are a restricted number of such regulatory elements where the ability to tune the expression of the GOI is limited. Furthermore, when differential expressions of multiple genes are required, the search for an optimal condition is often extensively time and resource consuming due to the permutation of the regulatory elements to be used. In addition, the multiple control elements use divergent mechanisms which are subjected to different global cellular controls. Because of these constraints, it will be difficult to predict the response of the system when engineered, thus reducing the chance of finding the optimal condition rapidly. Hence, simultaneously optimization of the expression of a number of genes in a pathway is still highly empirical, unpredictable and time consuming. Currently, there is no way of knowing if an optimal is achieved by tuning with the existing tools and methods, making these highly unsatisfactory. Hence, a tacit demand, yet to be met, is a systematic method to enable the optimization of the expression of multiple gene cassettes with predictable and well-controlled manner to enable the identification of an optimal set of parameters in a multidimensional space.

All isoprenoids are synthesized from two building blocks (IPP and DMAPP) by various synthase of the DXP or the MVA pathway and these can be heterologously expressed in *E. coli* (FIG. 1). To produce these two precursors through MVA pathway in *E. coli*, the whole heterologous pathway (hmgS, hmgR, MVK, PMVK, MVD)) including a native upstream enzyme atoB is required to be overexpressed (FIG. 1, MVA pathway) while several rate limiting steps have been identified for the native DXP pathway including the committed step, dxs, and three intermediate enzymes (ispD, ispF, idi (FIG. 1, DXP pathway). These rate limiting steps for isoprenoids production through either pathway have been divided into two or three pathway modules where expression levels were altered and optimized by varying their promoter types or recombinant plasmid copy numbers.

Figure 2B:
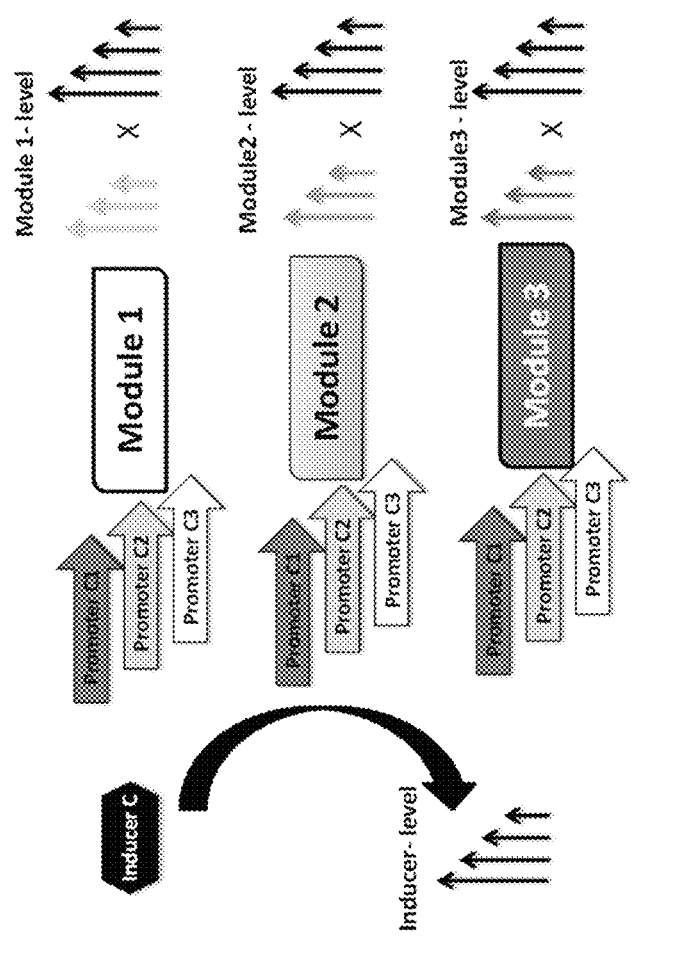
FIGS. 2A and 2B illustrate methods used for control of multiple pathway modules.
Figure 2A:
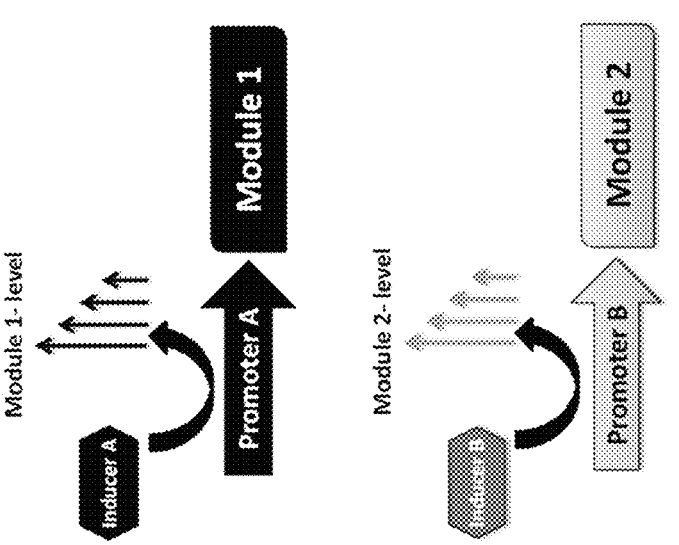

In this paper, the overexpression of some genes in the DXP pathway (dxs, ispD), ispl, idi) and heterologous MVA pathway were used as the focused modules for the development of tools. A series of novel methods and tools for simultaneously tuning of multiple pathway modules were systematically developed to optimize the production of isoprenoids (FIGS. 2A-2B). A decomposition method was first explored to individually regulate the pathway modules with various available tunable promoters (FIG. 2A). These independent promoters (uses different cellular resources to control each promoter) allowed each component in the module to be simultaneously altered by varying the concentrations of their inducers. The ease of continuously altering the expression of GOI by modulating the promoter using exogenously added inducers makes it a convenient method. This decomposition approach was successfully utilized to optimize lycopene—a C40 isoprenoid production with DXP pathway by tuning the upstream pathway module (SIDF) together with the downstream module (crtEBI) (FIG. 1). A global optimum could consistently be observed while excessive overexpression of the components in the modules resulted in inhibitory effects revealing the importance of pathway balancing. As this method is purely trial-and-error, the utility is severely limited by the enormous possible number of conditions to be tested with increasing permutation of modules.

Instead of decomposition, another systematic method was developed by treating the expression of multiple modules as an integrated process. The optimal condition for productivity is modulating at two orthogonal dimensions—the ratio between pathway modules and the overall expression levels of each component (FIG. 2B). Based on the strong original T7 promoter, mutant promoters with different strengths were generated and combinatorially controlling various modules to produce different ratios of genes expressed. On another dimension, the extrinsic transcriber, acting as a master regulator, alters the overall expression level by uniformly tuning all the promoters independent of their strength as a whole system. This univariant controlling method was initially demonstrated by optimization the production of lycopene and then extended to engineer a three module (S, ISF and ADS) synthetic pathway for amorphadiene—a C15 isoprenoid production (FIG. 1). According to the results, the system was mainly restricted by a single global boundary making it possible to carry out a rational optimization with the univariant controlling method, minimizing the number of strains to construct. The method was further successfully applied to identify the optimum condition for amorphadiene synthesis through MVA pathway by simultaneously tuning three pathway modules (SBR, KKDI and AA, FIG. 1). In addition, the properties and robustness of the invented tools were characterized at transcription and translation levels. The robustness of the system was also characterized by proving that two dimensions of control had no interaction and the engineered promoters would keep their relative strength at various conditions.

Results

Gene Overexpression Reduces Lycopene Production

Figures 3A, 3B:
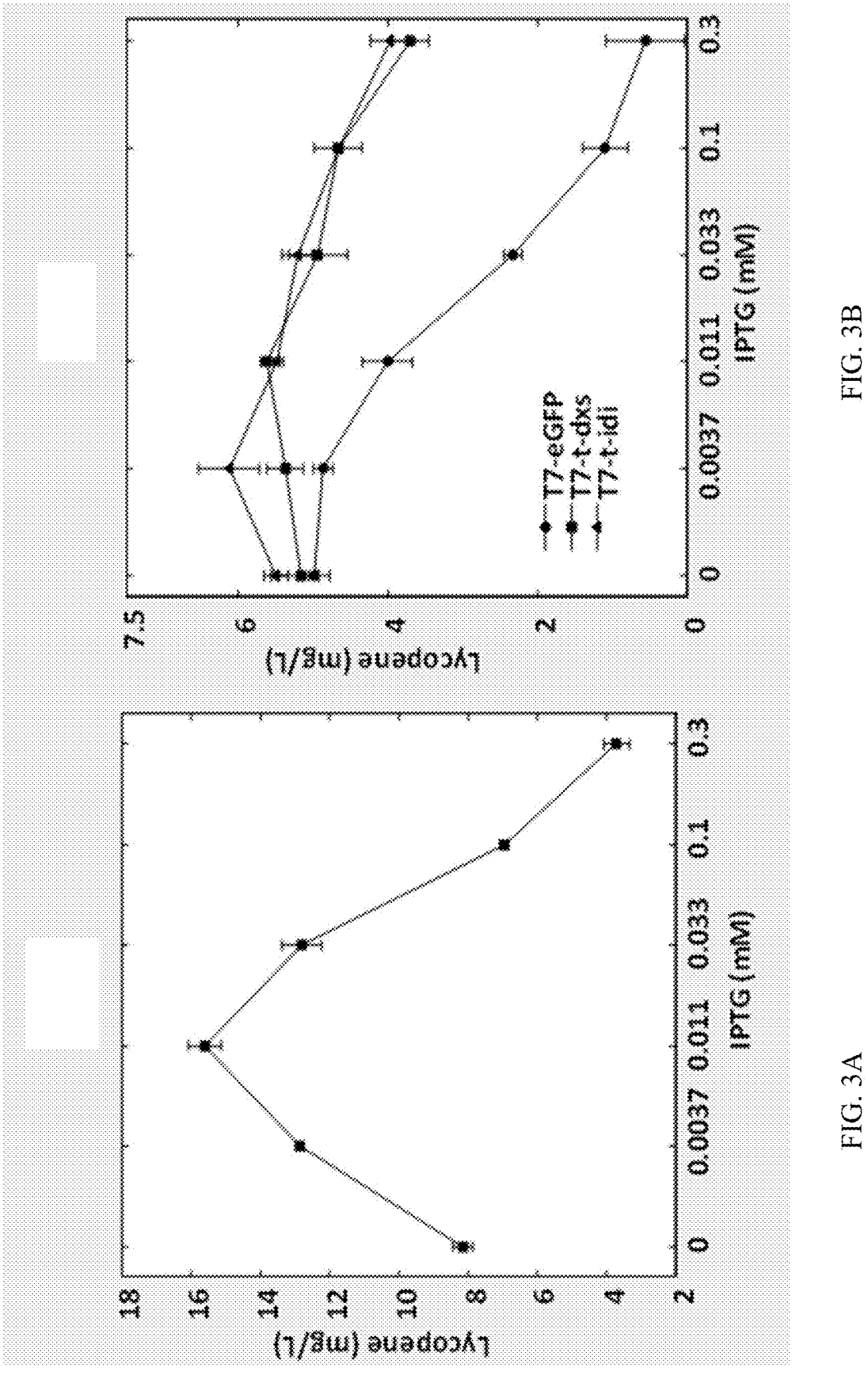
FIGS. 3A and 3B illustrate production inhibition caused by high gene expression. Lycopene yields responding to gene expression controlled by IPTG inductive T7 promoter in BL21-Gold (DE3) strain were measured.

Lycopene (C40 isoprenoid), an effective antioxidant, was initially synthesized in *E. coli* with the overexpression of four bottleneck enzymes dxs, idi, ispl), ispl in DXP pathway as well as three plant genes crtE, crtB, crtI separating into upstream (SIDF) and downstream (crtEBI) modules (FIG. 1). The excessive overexpression of enzymes can inhibit isoprenoid production. In order to investigate this issue, the SIDF module was expressed under control of inducible T7 promoter (pET-T7-SIDF plasmid) together with a constitutively expressed crtEBI module (pAC-LYC plasmid) in *E. coli* BL21-Gold DE3 strain. As predicted, the yield of lycopene increased initially but decreased at higher inductions (FIG. 3A). Initially, the hypothesis was that strong overexpression of upstream enzymes might interfere with the expression of downstream isoprenoid synthetic genes but it was later found to be incorrect. Further studies were carried out to test if the inhibition was caused by the function of expressed enzymes or the expression process itself. An enhanced green fluorescence protein (eGFP) without enzymatic activity and noncoding version of the dxs and idi genes (1-dxs and 1-idi), respectively, serving as translation and transcription controls were overexpressed at various levels together with a constitutive expression of crtEBI for lycopene production (FIG. 3B). The t-dxs and t-idi genes encoded dxs and idi, respectively, and were modified by deleting the ribosome binding sites as well as the start codons (ATG), thus disabling translation into proteins in *E. coli*. Based on the results, it was likely that the overexpression process, mainly due to synthesis of proteins, posed a global biochemical limitation that burdened the cells and inhibited the isoprenoid production.

Optimization of Lycopene Production with Two Independent Tunable Promoters

Figures 4A, 4B, 4C, 4D, 4E, 4F, 4G:
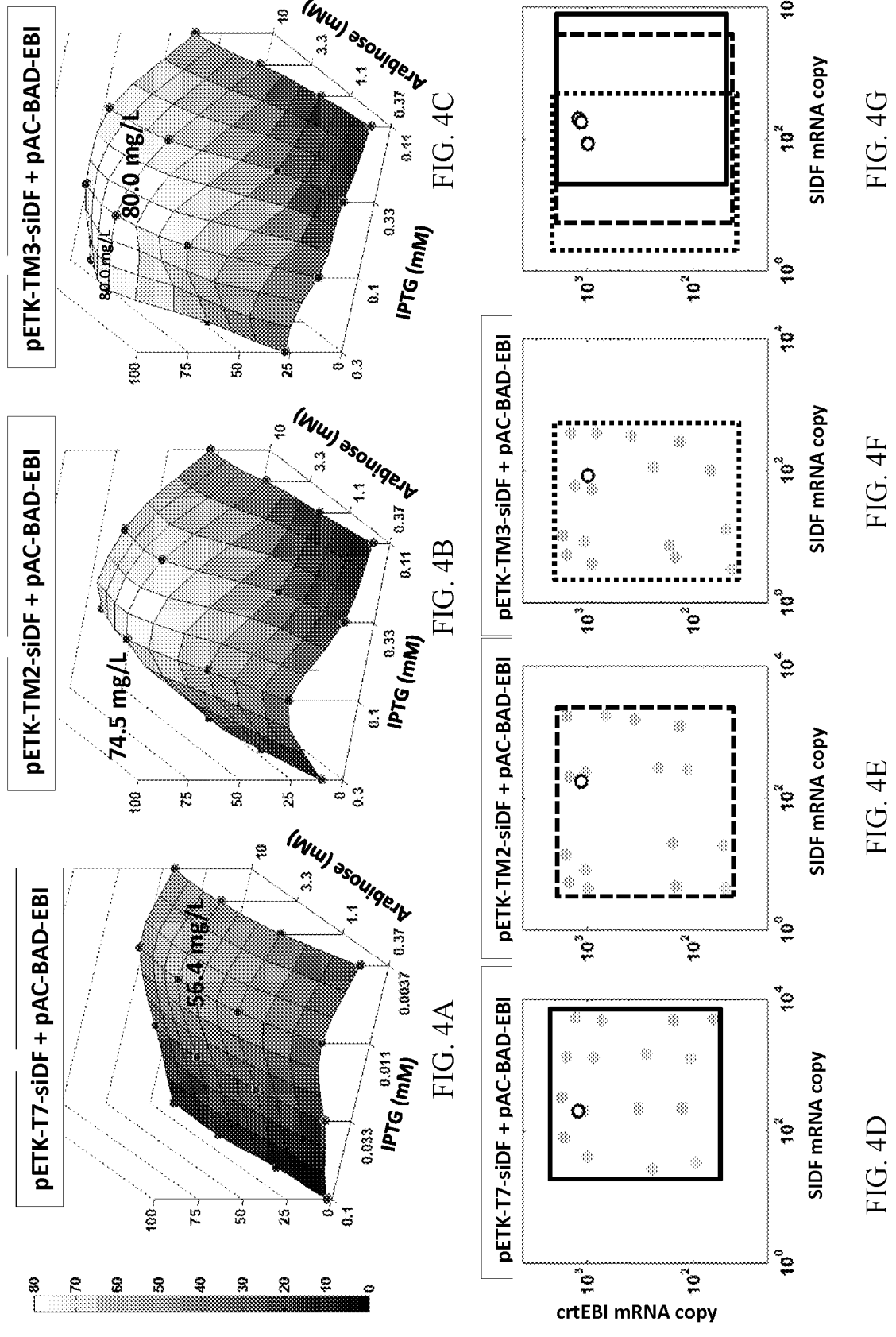
FIGS. 4A-G illustrate optimization of two modules for lycopene production with two independent tunable promoters.

In order to minimize the burden caused by overexpression, limited amounts of the bottleneck enzymes should be expressed. Hence, it was necessary to distribute the quota of resources to distinct pathway modules in a balanced manner to maximize the overall flux towards the product. Tunable promoters, where expression levels are conveniently and continuously modulated by the cognate transcribers, are highly desirable for rapid identification of the optimal condition (FIG. 4A). To demonstrate, the SIDF and the crtEBI modules were driven by two distinct independent tunable promoters: IPTG inducible T7 promoter and arabinose inducible pBAD promoter. A two-dimensional search was carried out by varying both inducers simultaneously (FIG. 4A). The expression of either module, where genes were expressed as a polycistron, was monitored by the transcription level of the first enzyme in each of the module (dxs for SIDF module and crtE for crtEBI module). Shown in the transcription result (FIG. 4D), both promoters can be independently and consecutively regulated. In the search space, a smooth lycopene response surface with only one optimum at high arabinose (3.3 mM) and low IPTG (0.011 mM) inductions was observed. A minimum induction was required for SIDF module indicating that the strong T7 promoter creating superfluous stress may not be suitable for usage here.

Design and Construct Mutant T7 Promoters

To alter the expression range, the T7 promoter was modified by site directed mutagenesis to create a mutant library with varying promoter strengths. The rate-determining steps of transcription with T7 RNA polymerase are the binding of polymerase to specific T7 promoter sequence followed by the melting of the double strand DNA and initiation of transcription with small transcripts. These actions can be mapped to the different regions of the conserved promoter sequence in FIG. 5. With the system in this study, IPTG functions by inducing T7 RNA polymerase synthesis and relieving the inhibition of the T7 based promoters by binding to the repressor from the lac operator. To maintain the tunability, the native T7 promoter was selectively disabled at the melting/initiation region as it is an inherent property of the promoter unlike the binding process that can be affected by parameters such as polymerase and DNA concentrations. Based on the strengths measured by in vitro transcription, selected mutant promoters covering various expression levels were constructed (Table 1) and their strengths were determined by quantifying eGFP protein expression. Strikingly, the strengths characterized in vivo were different from the published in vitro measurement (Table 1). According to the in vivo strengths, three low leaky T7 mutant promoters, herein named as TM1, TM2 and TM3, were chosen for further studies.

TABLE 1

| The strength of mutant T7 promoters | | | | | |
|---|---|---|---|---|---|
| No. | Promoter Name | Mutation | Leaky strength | Induced strength | Strength in literature |
| 1 | T7 | N.A. | 6.4% | 100% | 100% |
| 2 | | −2 to A, −3 to T | 3.6% | 104% | 42% |
| 3 | TM1 | −1 to T, −2 to A | 2.3% | 92% | 75% |
| 4 | | 2 to T, −1 to T | 1.5% | 85% | 65% |
| 5 | | −1 to T, −2 to G | <1% | 74% | 58% |
| 6 | | −2 to A, −4 to G | <1% | 42% | 41% |
| 7 | TM2 | −2 to G, −3 to C | <1% | 37% | 56% |
| 8 | | −3 to G, −2 to C | <1% | 26% | 46% |
| 9 | TM3 | +2 to A, +1 to A | <1% | 16% | 13% |
| 10 | | +2 to C, +1 to C | <1% | 12% | 33% |
| 11 | | +2 to A, +1 to C | <1% | 10% | 19% |
| 12 | | +1 to T, −1 to G | <1% | 6.1% | 24% |

Figure 5:
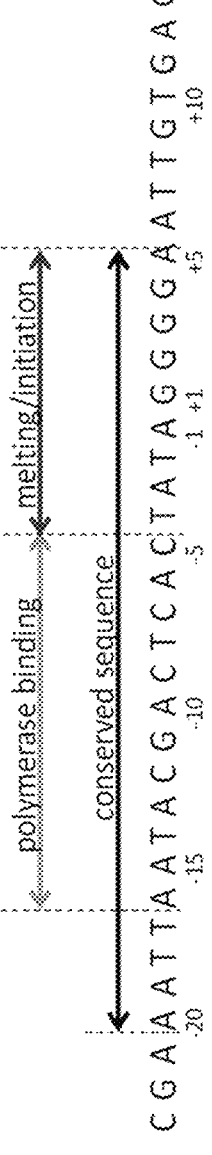
FIG. 5 illustrates sequences of T7 promoter SEQ ID NO.: 1. The numbers indicate the position relative to the transcription starting point (+1). The conserved sequence (bottom arrow), polymerase binding (top left arrow) and melting/initiation (top right arrow) regions are indicated.

All the mutation positions were labeled according to the sequence in FIG. 5. The leaky and induced (0.3 mM IPTG) expression levels were measured by expression of eGFP under control of various promoters in pET vector and normalized to the induced expression level of native T7 promoter.

Figures 6A, 6B, 6C:
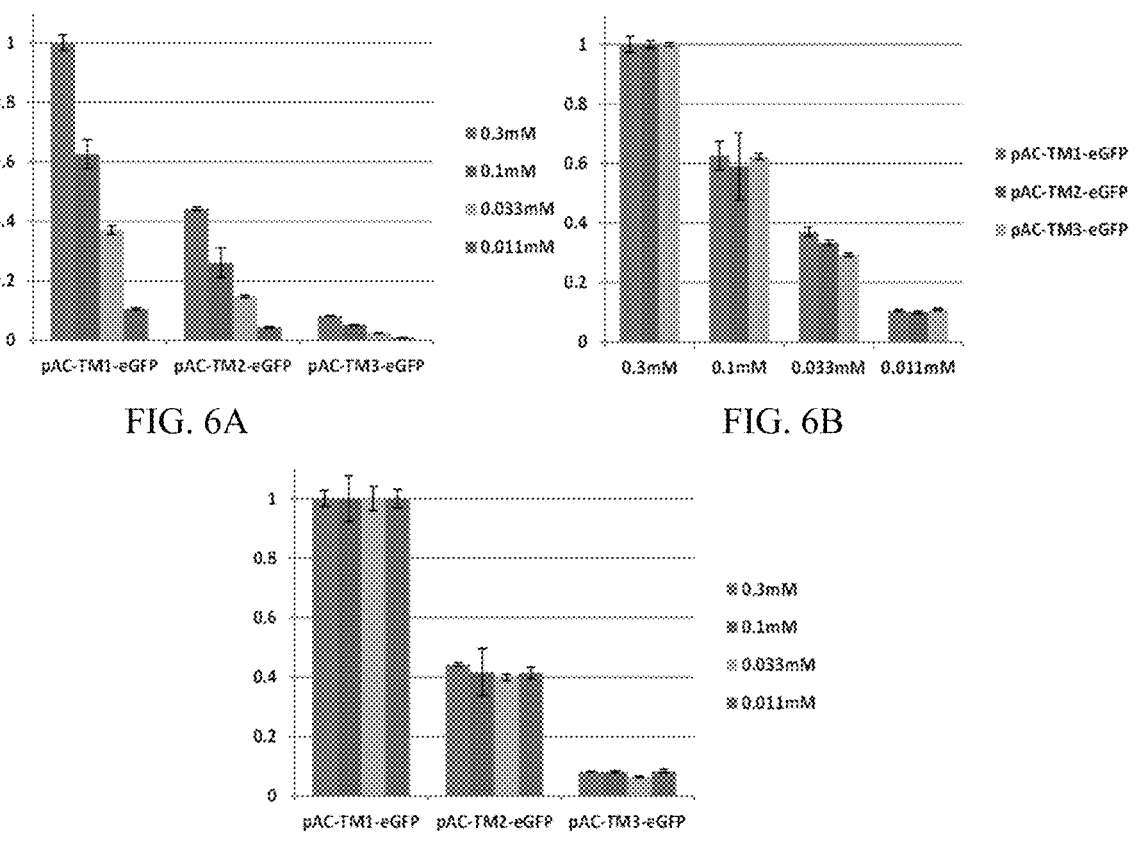
FIGS. 6A-6C illustrate the expression of eGFP controlled mutant promoters and IPTG. BL21-Gold (DE3) strains harboring eGFP expression plasmids: pAC-TM1-eGFP, PAC-TM2-eGFP or pAC-TM3-eGFP and pRepressor plasmid expressing lacI gene were grown in the presence of different IPTG concentrations. EGFP was extracted at 48 hrs after induction and measured with fluorescence reader (excitation wavelength: 588 nm, emission wavelength: 610 nm).
Figures 7A, 7B, 7C, 7D:
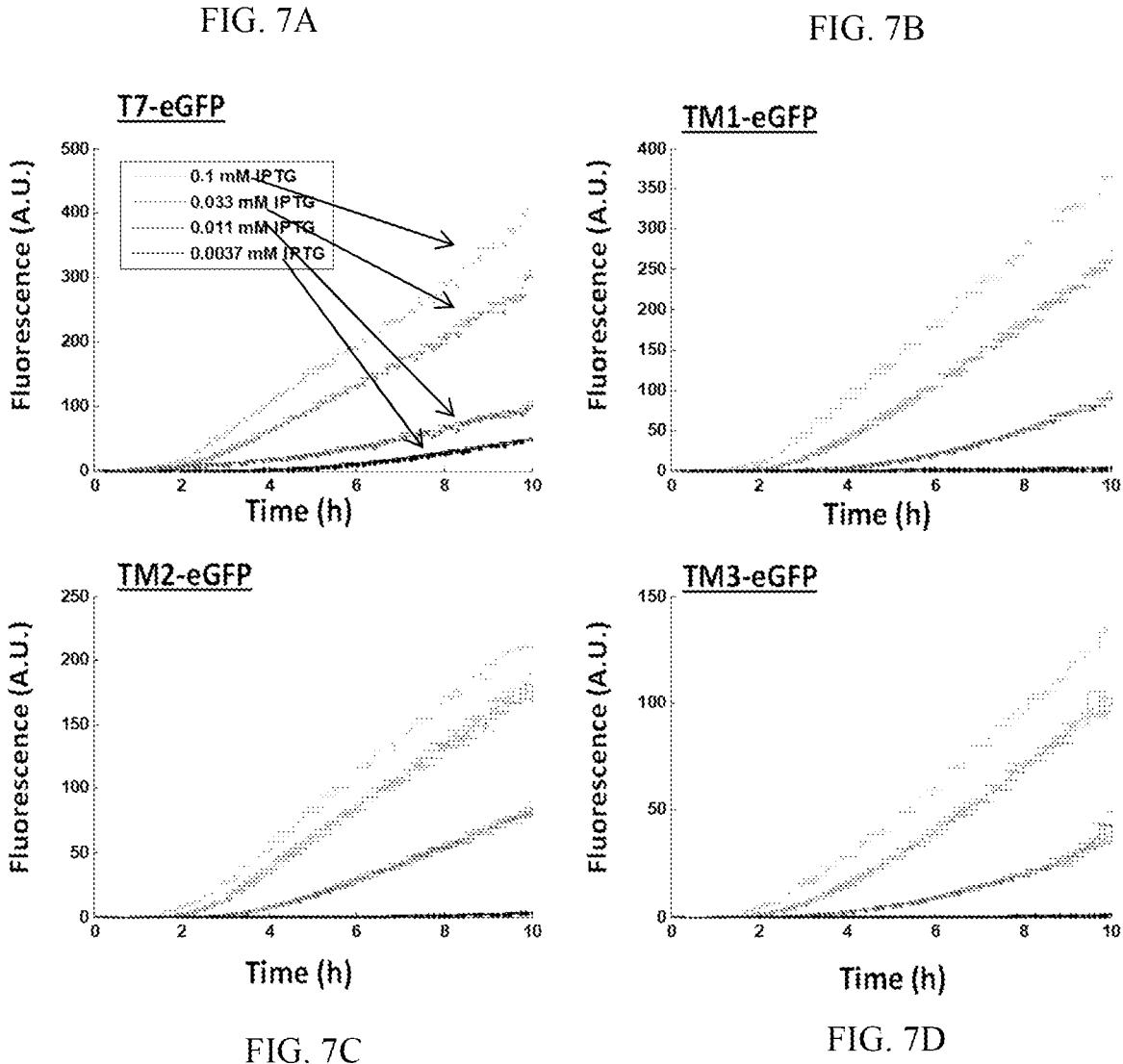
FIGS. 7A-7D illustrate the kinetic of eGFP expression driven by different promoters. BL21-Gold (DE3) strains harboring eGFP expression plasmids: pAC-T7-eGFP, pAC-TM1-eGFP, pAC-TM2-eGFP or pAC-TM3-eGFP and pRepressor plasmid expressing lacI gene were grown in the presence of different IPTG concentrations. Cells were incubated with 2xPY medium at 37° C. in Thermo Scientific Varioskan Flash Multimode Reader with shaking and eGFP was continuously monitored by measuring fluorescence (excitation wavelength: 580 nm, emission wavelength: 610 nm). The error bars represented the standard deviation of three biological replicates.

The differences between mutant promoters are solely defined by the rate of melting/initiation which is a first order reaction independent of other factors. As a result, all mutant promoters (TM1, TM2 and TM3) should have a similar response to IPTG induction. This was validated by expressing the eGFP as the reporter in pAC vector (FIG. 6A). According to the normalized expression levels, these mutant promoters responded to various doses of IPTG equally (FIG. 6B) and retain their relative strength upon various inductions (FIG. 6C).

Optimization of Lycopene Production with Mutant Promoters

Figure 8A:
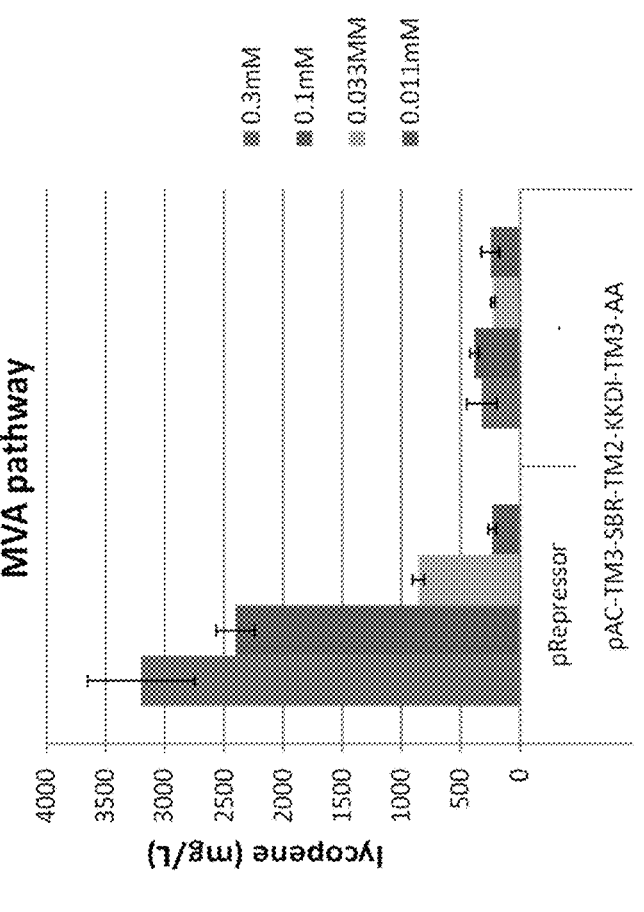
FIGS. 8A-8B illustrate unregulated promoters result decreased isoprenoid production. BL21-Gold (DE3) strains with or without pRepressor plasmid expressing the lac/repressor that inhibited the transcription from T7 based promoters before IPTG induction were introduced with amorphadiene synthetic pathways. The productions of amorphadiene were measured after various IPTG inductions.
Figure 8B:
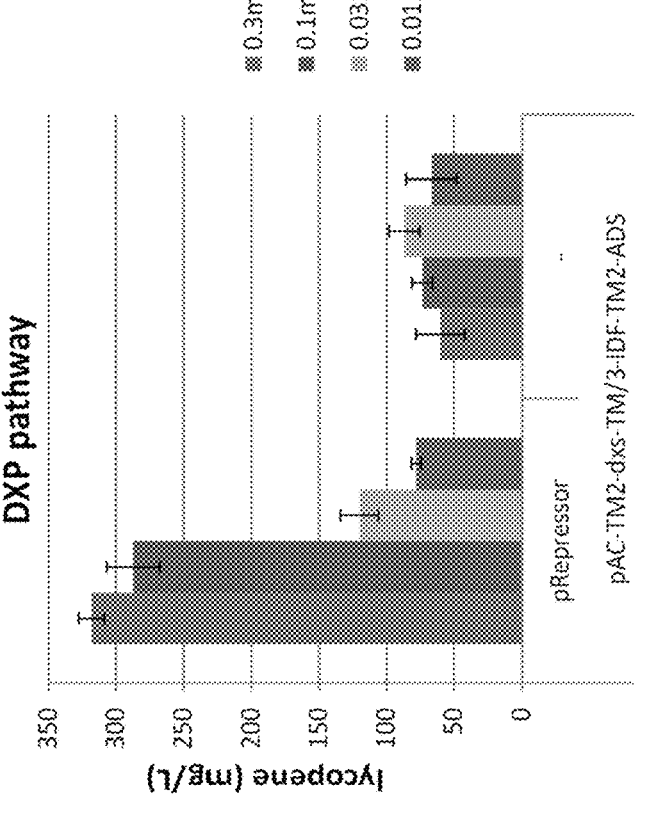

The T7 promoter for SIDF module was replaced with two significantly weaker promoters TM2 and TM3 to extend the search space. The transcriptional result (FIGS. 4E & 4F) showed that the mutant promoters have comparatively low expression in accordance to their strengths (FIG. 4G) and no interaction with pBAD promoter was observed. The lycopene response surface switched accordingly but kept with one optimum on the smooth surface (FIGS. 4B & 4C). The predicted optimum conditions identified with different promoters (T7, TM2, TM3) were closely located (FIG. 4G) which proved that reaching a balance between pathway modules was a major task for pathway optimization. Evidently, the mutant promoters extended the coverage of the expression range while the optimum yield for T7 promoter (56.4 mg/L) was not as high as that of TM2 (74.5 mg/L) or TM3 (80.0 mg/L) promoters. A possibility was that to achieve the same expression level, the native promoter expressed the transcripts faster than the mutant ones which may impose excessive cellular burdens. However, regardless of the strength of the promoters, the expression rates showed similar kinetics in response to induction (FIGS. 7A-7D). Another issue related to the use of native promoter is the high leaky expression that may burden the cells even before induction. Consistent with this suggestion was the significant reduction in isoprenoid production through either DXP or MVA pathway in strains with the Repressor plasmid (providing lacI protein that suppresses the expression before IPTG induction) removed so as to enable a constitutive activation of the native promoter (FIGS. 8A-8B).

The library provided promoters with variety of tunable ranges was then used in conjunction with other independent promoter to optimize metabolite production in a multivariate manner.

Development of a Univariant Controlling Approach

Because of the limited types and tunable range of independent promoters that are natural availability, a combinatorial multivariant-modular controlling approach is impractical with more than two modules where the experimental conditions will increase exponentially as well. In an attempt to develop a simplified, robust and rational engineering approach, the optimization challenge was dissected into two distinct parts: balance various pathway modules and reduce overexpression burdens. In order to maximize the flux efficiency and avoid toxic or inhibitory intermediates, a balanced pathway is always critically independent of the overall flux. On the other hand, the overall expression needs to be optimized to balance flux and burden—a general limitation caused by high expression regardless of the function of the module. To address these two distinct yet related challenges (flux and burden), selected promoters from the T7 promoter library was used to alter the relative ratios between various pathway modules by their strength. At the same time, the concentration of IPTG, serving as a global factor, was used to regulate the expressions of all the modules simultaneously while maintaining the ratios of promoter strengths (FIG. 2B). By tuning these two orthogonal dimensions, this univariant controlling approach was able to overcome the limitations of the combinatorial multivariant controlling with other approaches.

In order to test the hypothesis that the relative strengths or ratios of the strengths of these mutant promoters are indeed evenly distributed when they were competing for a limited pool of resource, an in vitro transcription system was established to mimic the circumstances encountered in vivo. The modules were standardized by expressing eGFP gene with short sequence tags which could be differentiated by specific qPCR primers (FIG. 9A). All combinations of two or three tagged modules were mixed with equal amounts in the reactions and the results showed that the modules with the same promoter but different tags behaved similarly, indicative that these sequences were expressed equally (P1-TM1/P2-TM1, P1-TM2/P2-TM2, P1-TM3/P2-TM3) (FIGS. 9B & 9D). Next, it was obvious that the expression levels of the gene from a weaker promoter (e.g., P2-TM2 in FIG. 9B), was expectedly lower in the presence of a strong promoter (P2-TM2/P1-TM1 in FIG. 9B) than when co-transcribed with a comparable promoter (P2-TM2/P1-TM2 in FIG. 9B) proving the occurrence of competition at the reaction conditions (high template concentration to T7 polymerase availability) (FIGS. 9B & 9D). Re-plotting the data (FIGS. 9C & 9E) it was clear that the relative strengths of the mutant promoters were fixed, even under competitive, resource limiting conditions. With such constant ratios, depending on mutant promoters, the modules will always have the same occupancies of the transcription resource regardless of the experimental conditions. While on the other independent orthogonal dimension, IPTG should still regulate the overall resource independent of other parameters.

Optimization of Lycopene Production with the Univariant Controlling Approach

Figure 10A:
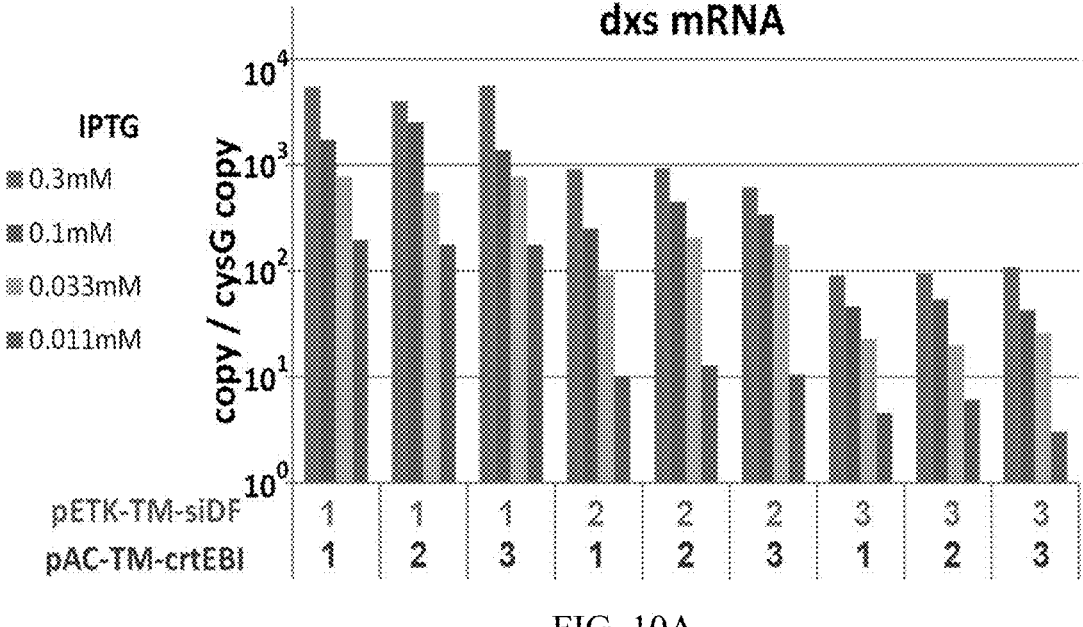
FIGS. 10A-10B illustrate transcription levels of two modules for lycopene production optimized with univariant controlling approach. BL21-Gold (DE3) strains harboring the combination of plasmids for two modules with different mutant promoters were grown in the presence of different IPTG concentrations for lycopene production. Two modules used in this study were the SIDF module (pETK-TM1-SIDF or pETK-TM2-SIDF or pETK-TM2-SIDF plasmid) and the crtEBI module (pAC-TM1-crtEBI or pAC-TM2-crtEBI or pAC-TM3-crtEBI plasmid). Note that both vectors were inducible by IPTG. The copy numbers of the vectors, pET and pAC are 100 and 30, respectively. The transcription level of SIDF module (dxs mRNA) (FIG. 10A) and crtEBI module (crtE) (FIG. 10B) were measured with the protocol described in experimental method and normalized to the level of cysG. For each data set on the X-axis, the IPTG concentrations are from highest (0.3 mm) to lowest (0.011 mm), from left to right.
Figure 10B:
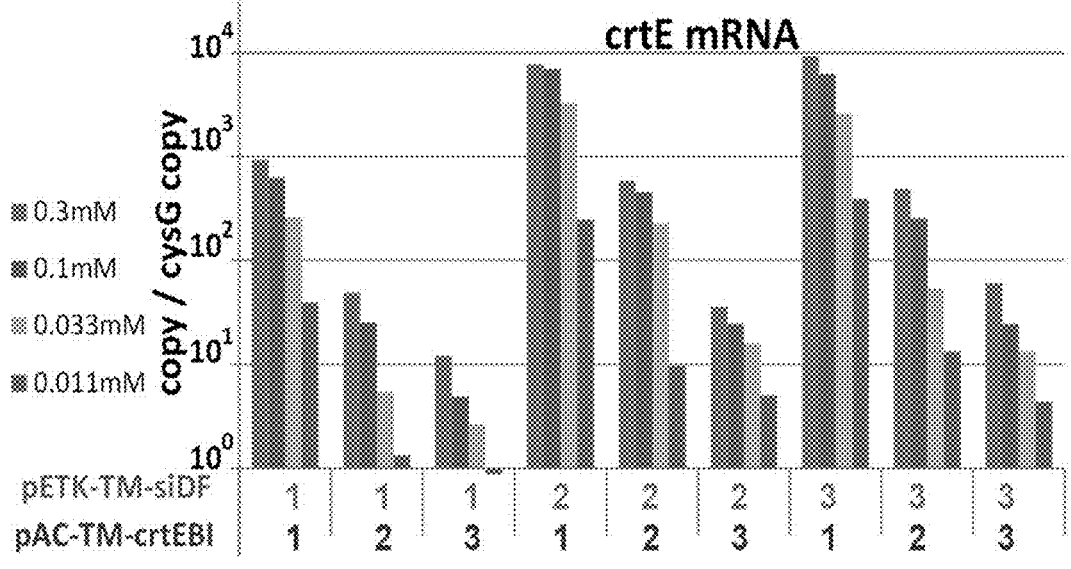

To further demonstrate, three promoters with varying strengths (TM1, TM2 and TM3, Table 2) were selected to control the expressions of the SIDF and crtEBI modules in a combinatorial way. Firstly, the transcription levels of the modules were measured so as to exam the behavior of the co-existing promoter in vivo. The inducer IPTG (0.3-0.011 mM) was added to the cells with various combinations of the mutant promoters (e.g, pETK-TM-SIDF TM1 with PAC-TM-crtEBI TM1) in pAC and pET vectors (FIG. 10A). All mutant promoters expressing SIDF (pET vector) responded to IPTG similarly regardless of their strengths and the type of co-expression promoters. When the strongest promoter (TM1) is expressed in a high copy number plasmid (pET, ~100 copies), the expressions of the genes (crtEBI in pAC, ~30 copies) were found to be lower than expected when compared to the other combinations (FIG. 10B) indicative of the limitation of transcription resource. Importantly, even in this situation, the relative strengths of mutant promoters remained constant (first 3 sets of TM combinations). A common (univariant) resource is distributed at fixed ratios over mutant promoters with pre-set transcriptional strengths. Hence, any change in the global supply of resource will influence the transcription from each mutant promoter in a pre-set manner.

Figures 11A, 11B, 11C:
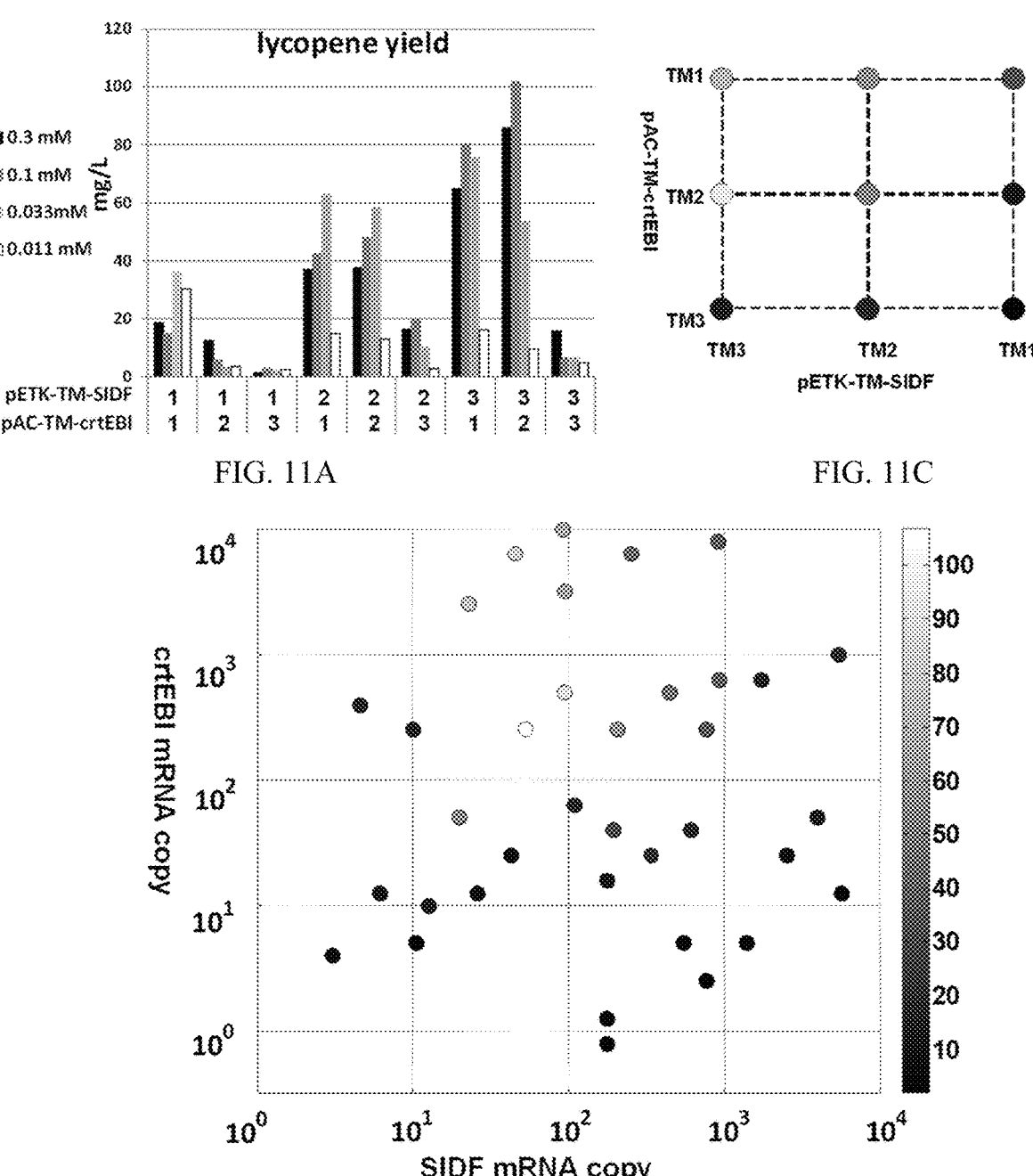
FIGS. 11A-11C illustrate optimization of two modules for amorphadiene production with univariant controlling approach. BL21-Gold (DE3) strains harboring the combination of plasmids for two modules with different mutant promoters were grown in the presence of different IPTG concentrations for lycopene production. Two modules used in this study were the SIDF module (pETK-TM1-SIDF or pETK-TM2-SIDF or pETK-TM2-SIDF plasmid) and the crtEBI module (pAC-TM1-crtEBI or pAC-TM2-crtEBI or pAC-TM3-crtEBI plasmid.
Figures 12A, 12B, 12C, 12D:
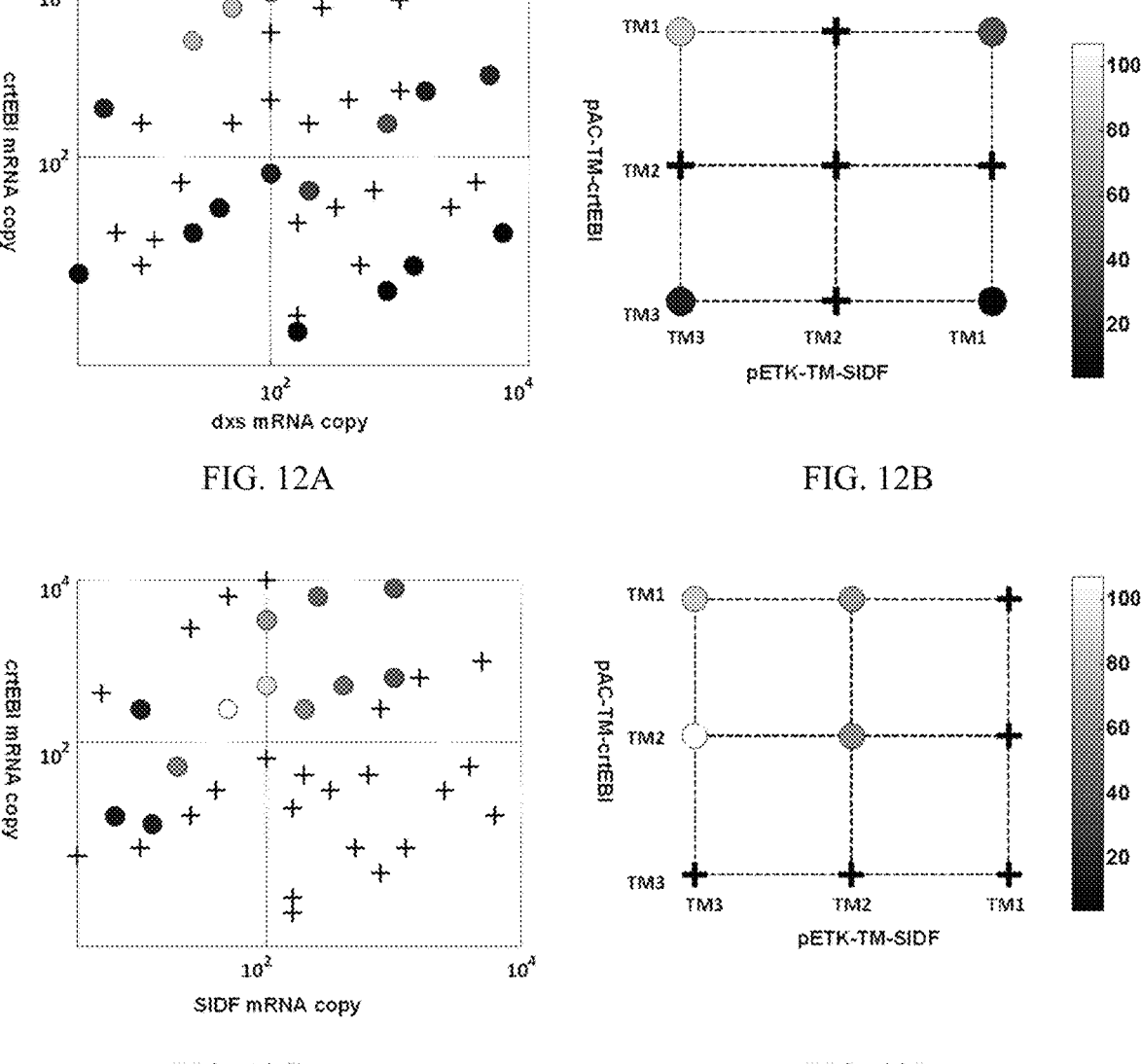
FIGS. 12A-12D illustrate rational optimization of lycopene production. A simple rational workflow can be used to guide strain development. Firstly, a screening experiment can be conducted using only high (TM1) and low (TM3) strength promoters with various IPTG inductions to discretely cover the searching range (FIG. 12A). The response of the system to mutant promoters will reveal that applying stronger promoters for the expression of crtEBI module than SIDF module gives better yields (FIG. 12B). A second round of focused experiment around the optimum conditions deduced from the screening experiment can be then carried out and the optimum condition (pETK-TM3-siDF, PAC-TM2-crtEBI, 0.1 mM IPTG) will be attained (FIGS. 12C & 12D). By such approach, an optimal condition can be easily identified without the need to search for more.

Next, the lycopene response using the univariant controlling approach was investigated. As expected, for any of the strains with various ratios between two modules, a compromising IPTG concentration for maximum lycopene by balancing of burden and flux could always be identified (FIG. 11A). On the other dimension, with optimal IPTG induction, lycopene production response to different promoter pairs differed (FIG. 11C). In general, crtEBI module required a stronger (TM1 or TM2) promoter than SIDF module (TM3) and the yield would be extremely low in contrary situations. These observations demonstrated the importance of both dimensions for optimal tuning. Putting the two dimensions together, the tested conditions dispersed well in the whole search space (FIG. 11B) the one that was wider than using pBAD promoter (FIGS. 4D-4F) for crtEBI module. Consequently, a slightly higher lycopene yield (102 mg/L) was achieved. Again, a global optimum was be identified and condition located adjacent it would have higher production than those distant ones. The existence of single global boundary allowed employing a rational optimization approach that stepwise zoomed into the optimum conditions which would then allow an accelerated optimization process by reducing the number of strains to be constructed (FIGS. 12A-12D).

Simultaneously Optimization of Three Pathway Modules with the Univariant Approach In previous studies, four bottle neck steps, scattered throughout the DXP pathway (FIG. 1), was grouped into a single module. It is highly possible that the optimal expression level for the committed step, dxs, is different from the rest of the intermediate steps (idi-ispl)-ispF, IDF). The fact that IDF are the three enzymes in DXP pathway found to be highly soluble upon overexpression as compared to the rest of the enzymes in the pathway suggests that less expressions may be required of them. To investigate this issue, the upstream pathway was divided into dxs and IDF modules and another important isoprenoid-amorphadiene, the precursor for antimalaria drug artemisinin, was synthesized with DXP pathway by changing the crtEBI module to ADS gene encoding amorphadiene synthase. To eliminate the possible biases caused by the variation of plasmid copy numbers, a library (27 recombinant plasmids) harboring the full combination of three promoters (TM1, TM2, TM3) with the three modules were constructed into a single pAC vector with the CLIVA method and each of these plasmids was transformed into BL21-Gold DE3 strain along with a pRepressor plasmid critical for the function of IPTG.

Tuning of IPTG, as expected, allowed the identification of optimal overall expression for each engineered strain (FIG.

Figure 13A:
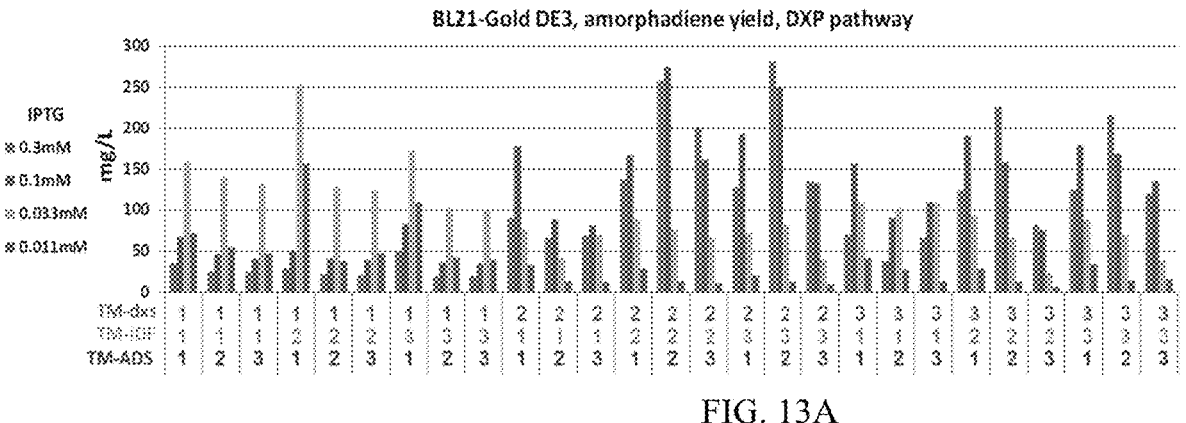
FIGS. 13A-13C illustrate optimization of three modules for amorphadiene production with univariant controlling approach. DXP or MVA pathway was applied for amorphadiene synthesis in either BL21-Gold DE3 or MG1655 DE3 strain. The combination of TM1, TM2, TM3 promoters were used to drive the expression of three modules for either DXP pathway approach (pAC-TM-dxs-TM-IDF-TM-ADS plasmid) or MVA pathway approach (pAC-TM-SBR-TM-KKID-TM-AA plasmid). Strains harboring the pathway and pRepressor plasmid expressing lacI gene were grown in the presence of different IPTG concentrations. Amorphadiene yields were presented in FIG. 13A: BL21-Gold DE3 strain, DXP pathway.
Figure 13B:
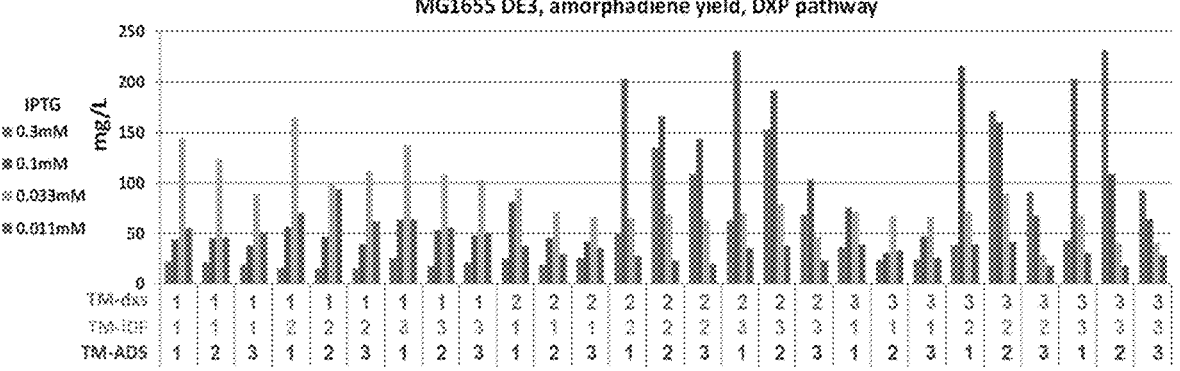

13A). To extend the findings, the system was transferred to another routinely used *E. coli* strain MG1655 DE3 (K12 strain family) differing from the former B strain derivative BL21-Gold DE3 (FIG. 13B). As expected, the IPTG performed well on balancing the burden and overall expression for each condition while notable difference could be observed comparing two strains. For MG655 DE3 strain, the maximum yield was attained at two conditions: pAC-TM2-dxs-TM3-iDF-TM1-ADS with 0.1 mM IPTG (232 mg/L) and pAC-TM3-dxs-TM3-IDF-TM2-ADS with 0.3 mM IPTG (232 mg/L) indicative that, for an optimum production, more ADS than dxs is required while the expression of IDF should be kept as low as possible, which validated our previous hypothesis. On the other hand, the best conditions for BL21-Gold DE3 strain: pAC-TM2-dxs-TM3-IDF-TM2-ADS with 0.3 mM IPTG (281 mg/L) and pAC-TM2-dxs-TM2-IDF-TM2-ADS with 0.1 mM IPTG (274 mg/L) showed an equal expression for the dxs and ADS modules.

Figures 14A, 14B, 14C:
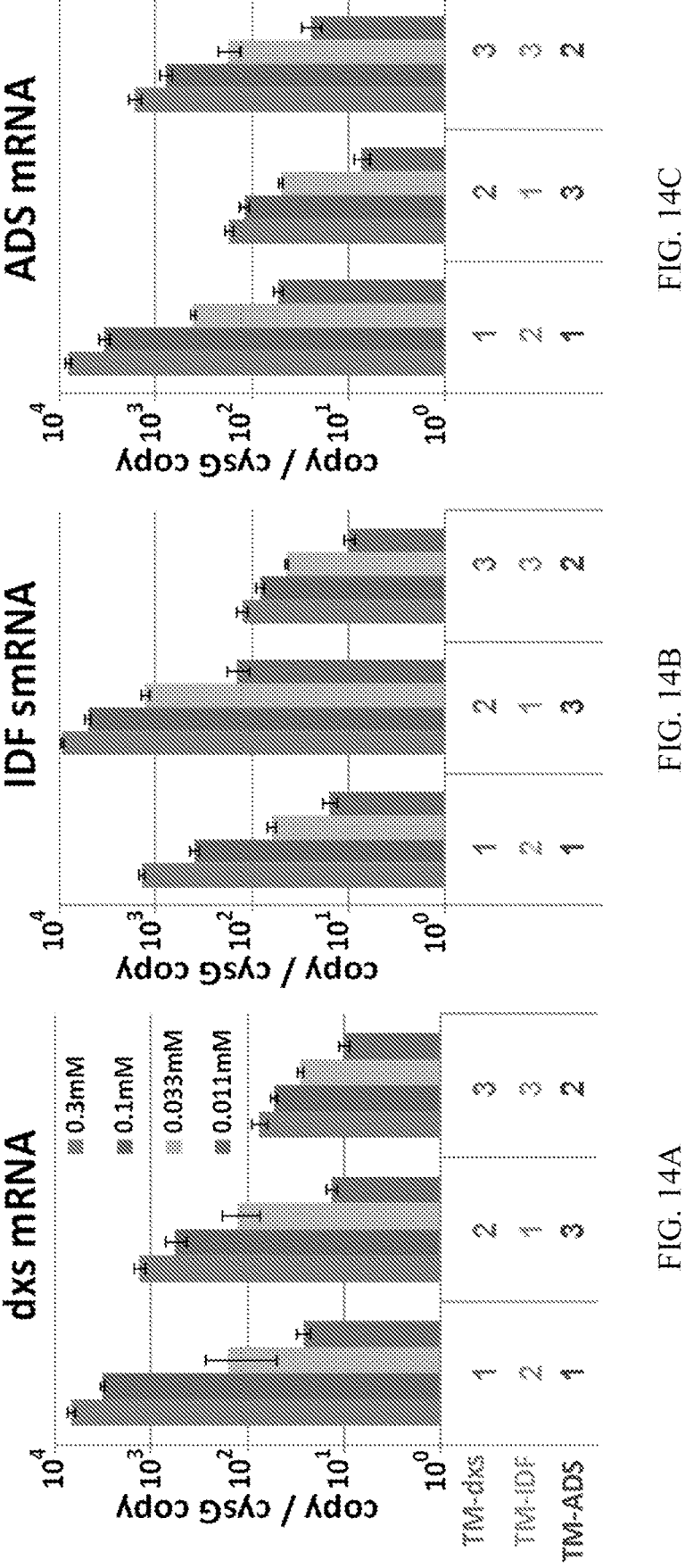
FIGS. 14A-14C illustrate transcription levels of selected strains with three modules on pAC vector. BL21-Gold (DE3) strains harboring selected plasmids: pAC-TM1-dxs-TM2-IDF-TM1-ADS plasmid, pAC-TM2-dxs-TM1-IDF-TM3-ADS plasmid or pAC-TM3-dxs-TM3-IDF-TM2-ADS plasmid and pRepressor plasmid (expressing lacI gene) were grown in the presence of different IPTG concentrations. The combination of pathway modules were presented at X axis and the IPTG concentrations were presented as different colored bars. The transcription level of each module (dxs, IDF, ADS) was measured with the protocol described in experimental method and normalized to the level of cysG. The error bars represented the standard deviation of three biological replicates. For each data set on the X-axis, the IPTG concentrations are from highest (0.3 mm) to lowest (0.011 mm), from left to right.
Figures 15A, 15B, 15C, 15D:
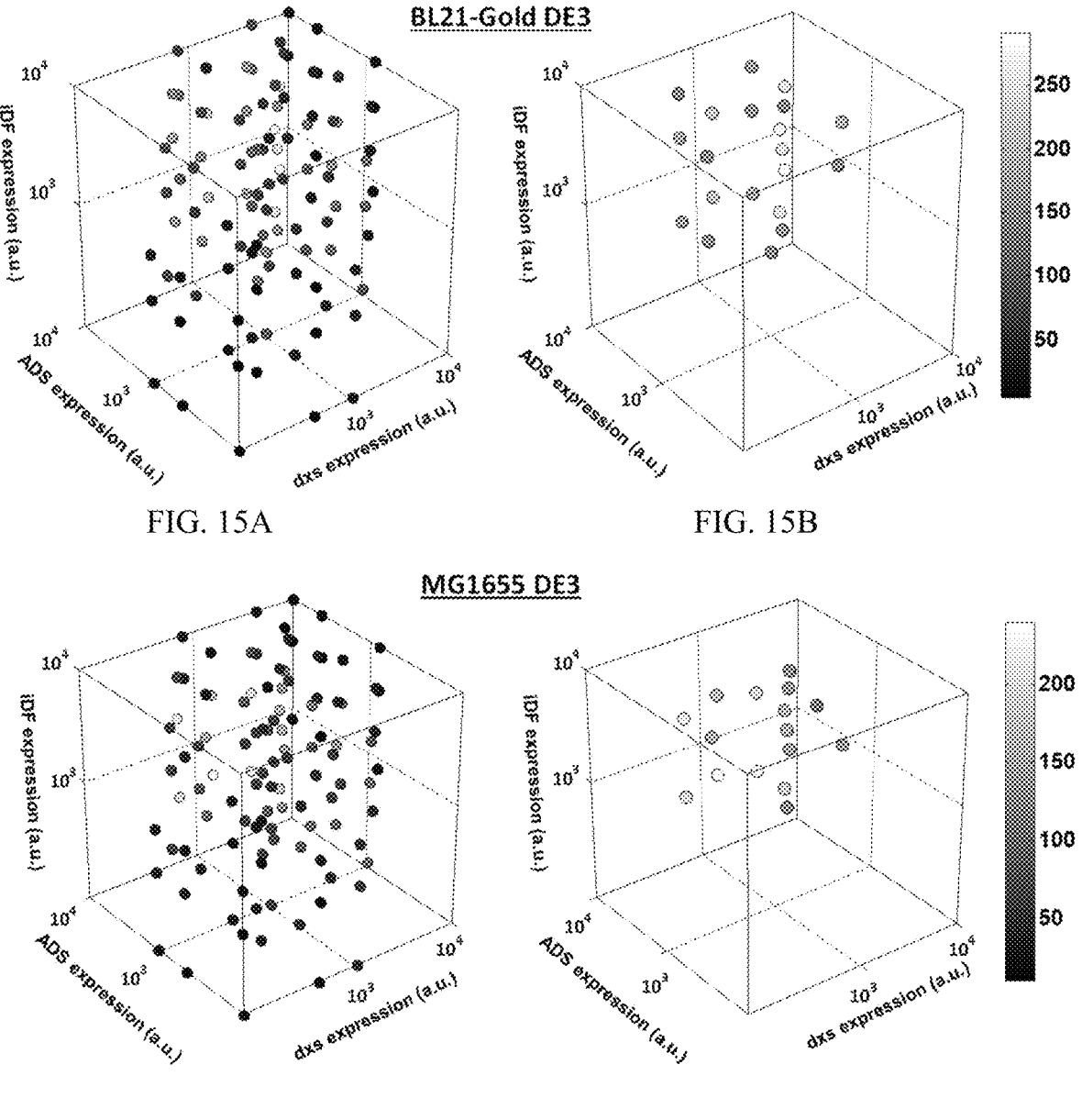
FIGS. 15A-15D illustrate amorphadiene production response to the relative expression levels. Strains harboring different pAC-TM-dxs-TM-IDF-TM-ADS plasmids with the combination of TM1, TM2, TM3 promoters on three modules and pRepressor plasmid expressing lacI gene were grown in the presence of different IPTG concentrations for amorphadiene production.

The measurement of expression levels of the selected strains revealed that with a low copy pAC vector, the competition for transcriptional resource did not appear to occur (FIGS. 14A-14C). On basis of that, the relative expression level (a.u.) of modules controlled by the univariant controlling method can be calculated by "Equation 1" where parameters were fitted by least squares method from the data of "FIGS. 6A-6C". The amorphadiene production corresponding to the relative expressions of the 3 modules were then represented in a 3-D graph (FIGS. 15A & 15C). According to the plot, the univariant controlling method systematically covered a large space within which neither too low nor too high expression was propitious to production. The deduced high production conditions (more than half of the maximum) for both strains (FIGS. 15B & 15D) were located at a fairly focused space raising the possibility of the existence of a single optimum.

$$\text{Equation 1}$$

Calculation of relative expression levels in arbitrary units ($a.u$)

$$\text{Relative expression } (a.u.) =$$
$$\text{IPTG induction strength} \times \text{Mutant promoter strength}$$

$$\text{IPTG induction strength} = \begin{cases} 100, & 0.3 \text{ mM } IPTG \\ 61.4, & 0.1 \text{ mM } IPTG \\ 33.6, & 0.033 \text{ mM } IPTG \\ 10.5, & 0.011 \text{ mM } IPTG \end{cases}$$

$$\text{Mutant promoter strength} = \begin{cases} 100, & TM1 \text{ promoter} \\ 41.9, & TM2 \text{ promoter} \\ 7.9, & TM3 \text{ promoter} \end{cases}$$

The pathway modules' expression levels were calculated as the product of the mutant promoter strengths and IPTG induction strengths. Based on the expression level of eGFP under control of mutant promoters and IPTG inductions (FIGS. 6A-6C), the value of both strengths was estimated with least square linear optimization. The maximum levels were arbitrarily assigned as one hundred. As IPTG induction has similar effects on different promoters, multiplication between the two values was used to obtain the relative expression levels.

Figures 16A, 16B, 16C:
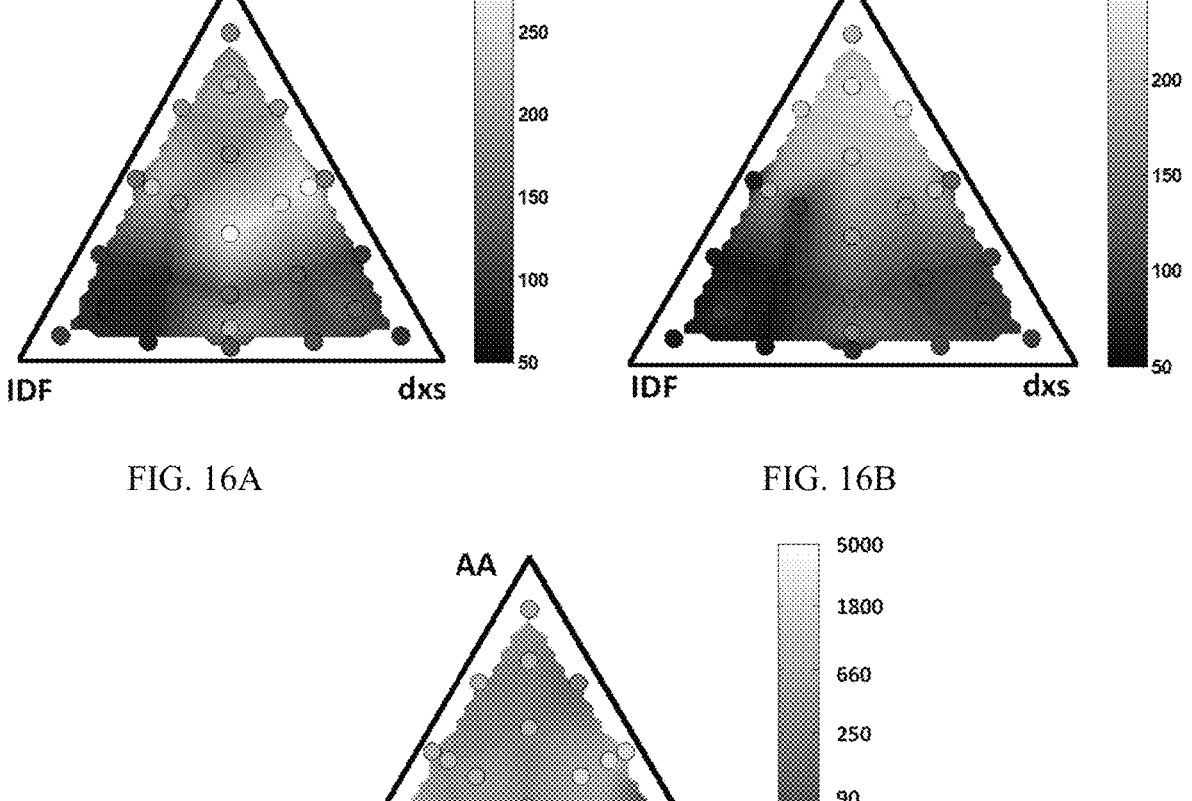
FIGS. 16A-16C illustrate ternary plot representation of the amorphadiene production.
Figure 17A:
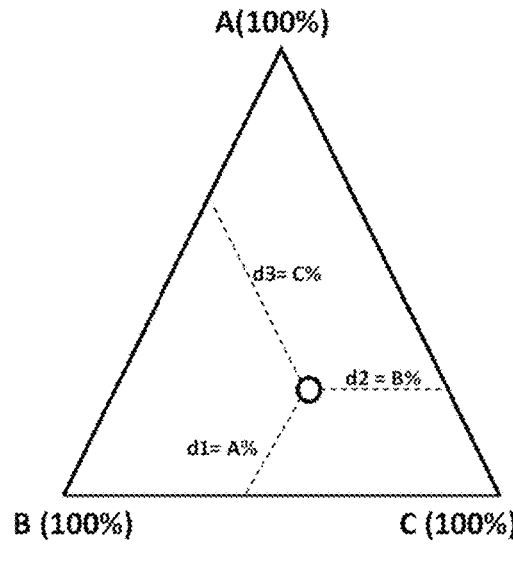
FIGS. 17A-17D illustrate ternary plot of amorphadiene response to ratios of three modules.
Figure 17B:
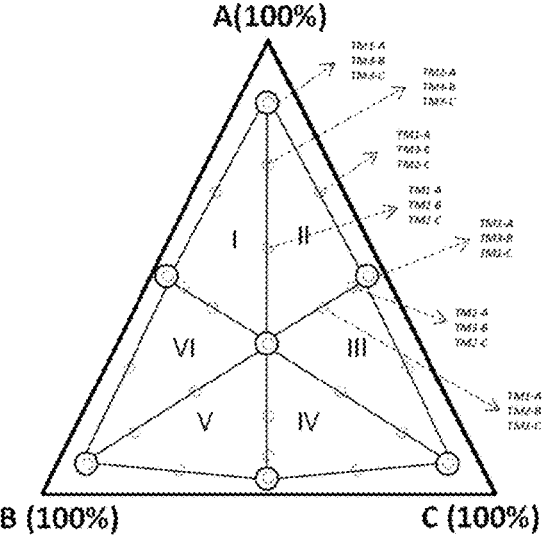
Figure 17C:
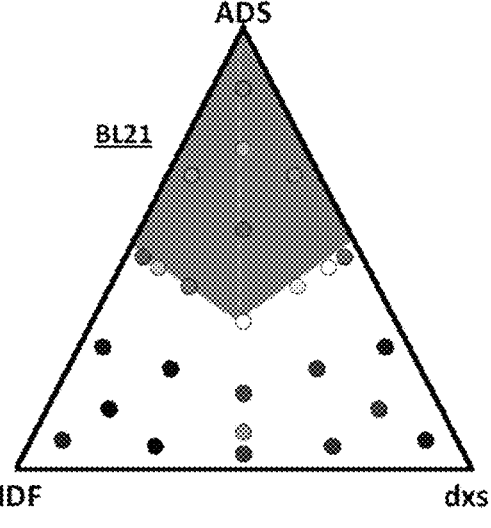
Figure 17D:
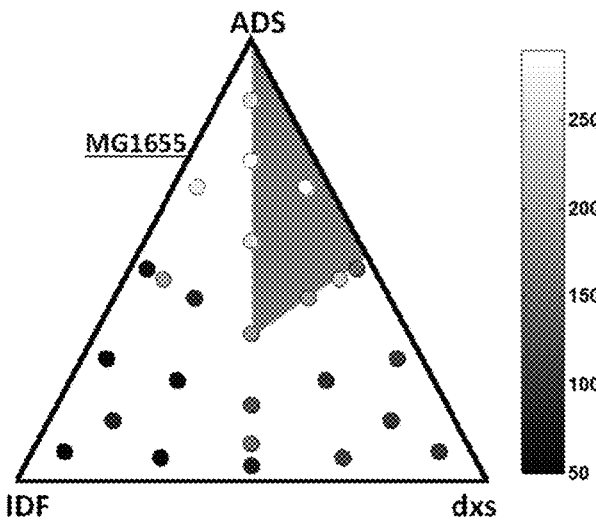

In an attempt to investigate the global trend at the dimension of ratios, the percentage modules in each construct were calculated according to the strength of mutant promoters and ternary plots were employed to illustrate the results. In the plot, each vertex of the equilateral triangle represents a pathway modules and the percentage of a specific module decreases linearly with increasing distance from its corner (FIG. 17A) where the color of the dots represented the optimized yield obtained at IPTG dimension (FIGS. 16A & 16B). The plots showed that a global optimum existed in both strains but slightly shifted towards more ADS in MG165 DE3 strain (FIG. 16B) when compared to BL21-Gold DE3 strain (FIG. 16A). On the whole, the conditions surrounding the global optimum have a higher yield than the far away ones. This kind of general reverse correlation indicated that the system has hit a global boundary, possibly due to the metabolic burden caused by high expression. On the other hand, the presence of several local optima, especially in BL21-Gold strain, suggested that there were local minor boundaries encountered. The global boundary leading to a continuous change in the yield throughout the search space allowed the rapid optimization of the pathway through a rational approach (FIGS. 17B-17D).

Applying the Univariant Controlling Approach for MVA Pathway Optimization

Figure 13C:
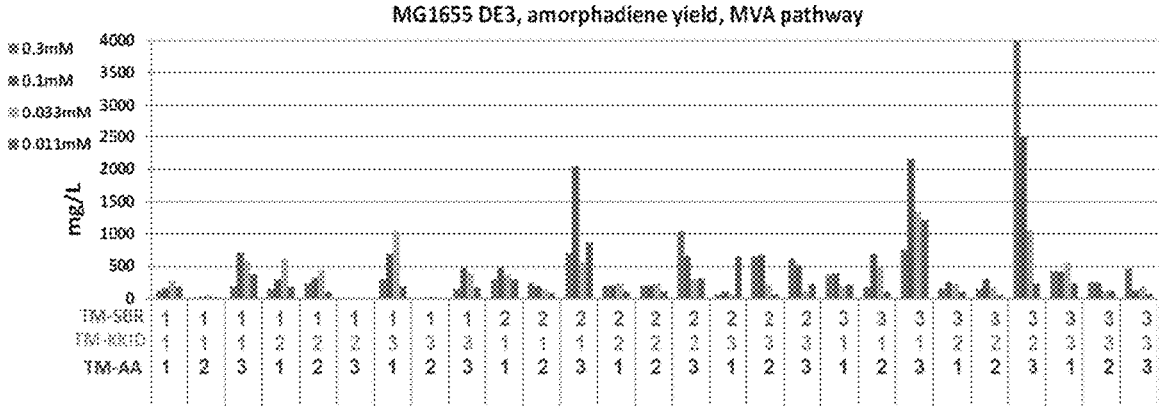

Next, the same approach was utilized to optimize the MVA pathway for amorphadiene production. The pathway was separated in to three modules SBR (hmgS-aroB-hmgR), KKDI (MVK-PMVK-MVD)-idi) and AA (ADS-ispA) according to the order of flux (FIG. 1). The overexpression of ispA was necessary when using MVA pathway but not DXP pathway which provides lesser upstream flux so that the endogenously expressed ispA is enough for fluxing (data not shown). By tuning the overall expression, an optimum could be identified for each strain as usual (FIG. 13C). Notably, the MVA pathway was more sensitive to the tuning of promoters (FIG. 13C) comparing to DXP pathway (FIGS. 16A & 16B). The clear optimal (pAC-TM3-SBR-TM2-KKDI-TM3-AA) and two suboptimal (pAC-TM2-SBR-TM1-KKDI-TM3-AA and pAC-TM3-SBR-TM1-KKDI-TM3-AA) revealed that a higher expression of KKDI module than the SBR module as well as a minimum expression of AA module was critical for the high production of amorphadiene. The same conclusion could be drawn from the ternary plot (FIG. 16C) where the global optimum located at a small corner area. The yields in this focused optimum region were distinctly higher than the rest of the conditions (the color representation for amorphadiene yield is in exponential scale).

Extracellular Accumulation of DXP Pathway Intermediates During Optimization

Figures 19A, 19B, 19C:
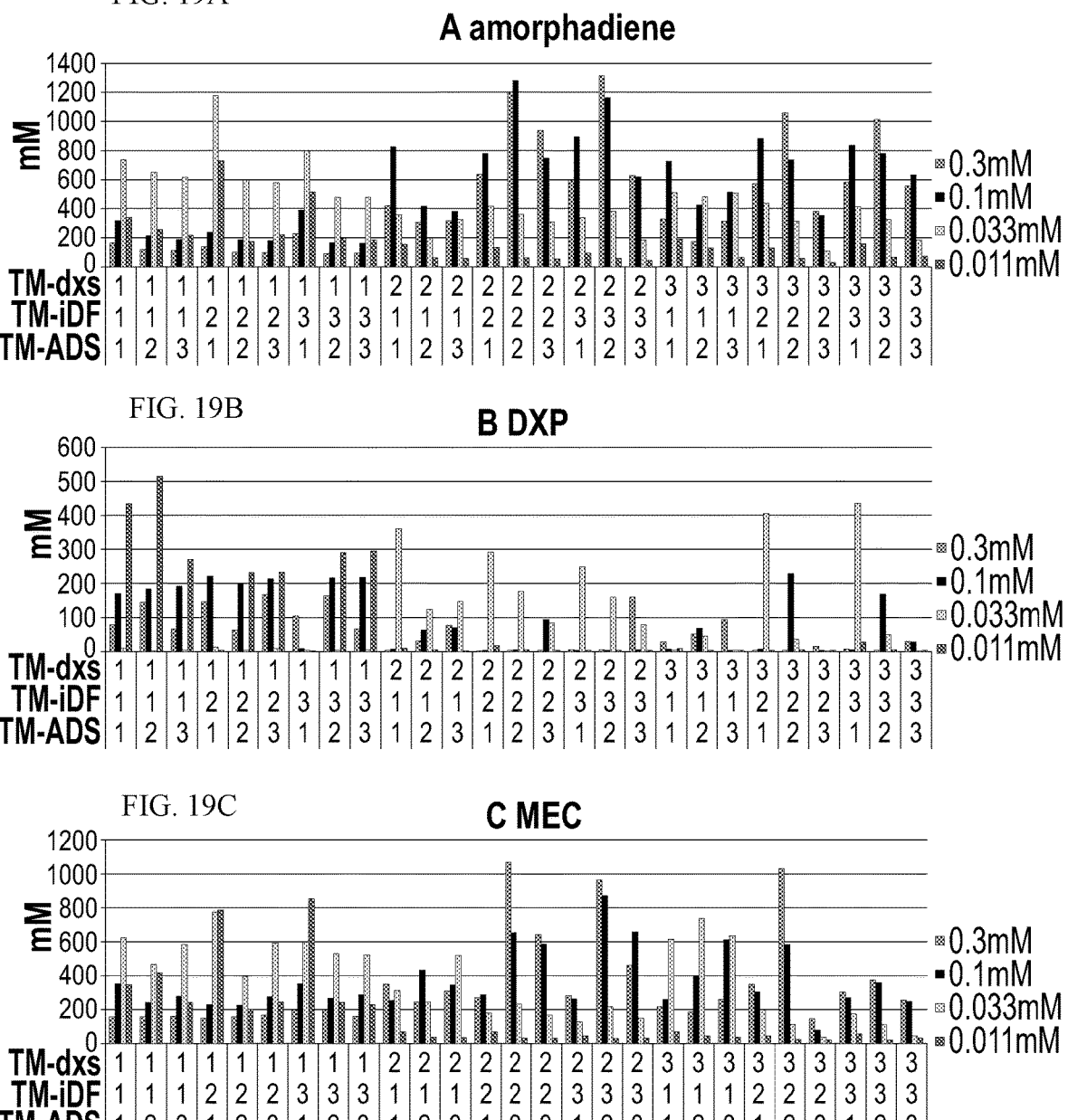
FIGS. 19A-19C illustrate accumulations of MEC and DXP in the medium. BL21-Gold (DE3) strains harboring pAC-TM-dxs-TM-IDF-TM-ADS plasmid with combinations of TM1, TM2, TM3 promoters and pRepressor plasmid (expressing lacI gene) were grown in the presence of different IPTG concentrations. The combination of pathway modules were presented at X axis and the IPTG concentrations were presented as different colored bars. The concentrations of amorphadiene (FIG. 19A), MEC (FIG. 19B) and DXP (FIG. 19C) in the medium were measured at the end point. To note that one molecule of amorphadiene is synthetized from three molecules of MEC or DXP. For each data set on the X-axis, the IPTG concentrations are from highest (0.3 mm) to lowest (0.011 mm), from left to right.

The efflux of DXP pathway intermediates when the pathway was overexpressed has been discussed. To further investigate the optimization process, extracellular accumulated metabolites of DXP pathway were measured for the Bl21-DE3 Gold strain in conditions for amorphadiene production optimization and DXP (1-Deoxy-D-xylulose 5-phosphate, product of dxs), MEC ((E)-4-Hydroxy-3-methyl-but-2-enyl pyrophosphate, product of ispF) were found to be significantly accumulated (FIG. 18A). Reasonably, more DXP were accumulated when a stronger promoter (TM1) was applied to the dxs module (FIG. 19B, TM-dxs=1). Examining the responses of various modules to IPTG induction carefully, at conditions optimum for amorphadiene production, significantly lesser amounts of DXP accumulated in the medium (FIGS. 19A & 19B compare amorphadiene and DXP). By tuning the overall expression level, an optimum could be identified with minimized leakage of pathway intermediates. With the rest of the conditions (FIG. 19B, TM-dxs=2, 3), DXP accumulated occasionally without a clear trend indicating the complexity of the process.

MEC accumulated to a higher level than DXP. Surprisingly, a similar response of MEC and amorphadiene could be found (FIGS. 19A & 19B, compare amorphadiene and DXP). As a secondary product of the pathway due to the limitation of downstream enzymes, the yield of MEC was well correlated with amorphadiene at all conditions (FIG. 18B) and the ternary plot only differed slightly (FIG. 18C). This meant that certain global parameter or the upstream part of the pathway (up to ispl) was the major limiting factor that was optimized for both products. However, the extra high local area (pAC-TM3-dxs-TM2-IDF-TM2-ADS) observed in ternary plot of MEC (FIG. 18C) did not exhibit low expression for ADS module which had no direct relationship with MEC accumulation indicating that the pathway optimization was a interrelated process.

Discussion

To engineer a biological process, the expressions of the related genes are the most commonly and useful method to increase productivity. For pathway optimization, combinations of different promoters (e.g, lac, T7, T5, BAD etc) and recombinant gene carriers (various plasmids or genome) are widely used in current practices, which is highly unsatisfactory due to lack of predictability. As a result, most of the studies only managed to vary and optimize one parameter at a time and those bottom-up approaches reflect no insight in the global status of the systems. To address this with a top-down approach, decomposed of the whole pathway into two modules where expressions were separately controlled by well characterized independent tunable promoters were initially carried out. The ease of control of individual inducers allowed the simultaneous and continuous alteration of the expressions of both modules and revealed a global optimum within the expression range. But this multivariate strategy is not ideal as most of the naturally tunable promoters in microbes used sugars as regulators. The sugar inducers may complicate the system as they are limited by the transportation system and may affect cellular metabolism while any perturbation of the global system will have distinct effects on each promoter, raising the difficulty in using multiple of them simultaneously. Together with the limitation of their dynamic range in tuning and the irrational nature of this multivariate approach, it can be impractical for manipulating multiple modules.

Rather than treating each module separately, another rational univariant controlling method was then developed by decomposing the regulatory process into two orthogonal dimensions: the overall expression level and the ratios between modules. The modulation of two dimensions was realized using a dependent tunable promoter library where promoter members share the same transcription resource-T7 RNA polymerase and a common mechanism of action so that the former dimension could be conveniently achieved by varying the availability of the inducer-IPTG. At the same time, mutations were specifically introduced to the melting/initiation region of the promoter making their relative strengths constant so that the ratio of modules was solely defined by the cognate promoters. The independence of two dimensions was validated at conditions when the promoters were used separately or together. With a wide dynamic range on both dimensions, the method comprehensively and continuously covers a board space allowing a systematic search for the optimum condition of three pathway modules. In addition, a rational approach can be applied to accelerate the optimization process, especially with complicated multiple module systems.

As kinetic events and confounded by multiple feedback controls and global factors, little is known about the mechanism of pathway optimization. The production of pathway enzymes has now been shown to act as burdens to the cell, possibly due to the synthesis of unnecessary proteins or the formation of inclusion bodies when they were profusely produced inside the cell. As a result, an optimum overall expression level could not be consistently predicted by tuning the IPTG concentration. Examining the other dimension of tuning in a ternary plot, a clear global optimum existed in all tested systems indicating the existence of major bottle necks which were presumably different for various systems as the MVA pathway was found to be much more sensitive to tuning than the DXP pathway. The information gained can serve to guide the identification of novel bottle necks. Further optimization to the system will no longer involve tuning the expression of the genes but other factors, e.g. strains, growth medium etc. This is important because by knowing the limits, other potential directions can be explored with confidence. For example, when studies were carried out initially with BL21-Gold (DE3) strain and later to MG1655 DE3 strain, different locations of the global optimum were identified in the ternary plot where the optimal values were comparable.

When optimizing DXP pathway for amorphadiene production, the amount of intermediates released extracellularly responded distinctly to pathway tuning-MEC had a similar profile as amorphadiene while DXP was inversely correlated when the dxs module was highly expressed. An obvious kinetic difference between these may possibly be due to DXP being re-consumed by the cell but not MEC, which further increase the complexity of the optimization task. Despite all these confounding mechanisms, the univariant control method described herein provides a systematic, rational and robust tool for the modulation of multiple genes for metabolic pathway optimization.

CONCLUSION

A univariant control method was established for the multivariate engineering of pathway modules by tuning two dimensions: the ratios between the modules and the overall expression defined with biological principles. The tuning of the ratios balanced the activity of pathway enzymes so as to minimize the accumulation of unwanted intermediates. While the overall expression level is related to metabolic flux and metabolic burden, the fine tuning balanced these two competing parameters. A well characterized and designed T7 promoter library was established which enabled the orthogonal regulation at these two dimensions.

Comparing to other less systematic methods which attempt to modulate different pathway modules separately, the method described in this paper allowed searching of a broad gene expression space with minimal effort. Moreover, the optimize systems were more tolerant to global and environmental changes.

Applying the tools, combinatorial engineering of DXP or MVA pathway for isoprenoids production were carried out. Global optima were identified and at these conditions, large enhancements on the yields (>40 fold for DXP pathway and >1000 fold for MVA pathway) were observed.

Methods

Bacteria Strains and Plasmids Construction

All the plasmids used in this study were summarized in "Table 2". The original vector pBAD-B was purchased from Invitrogen and pET-11a was purchased from Stratagene. RK2A vector (pJB864) (Blatny, J. M., et al., "Improved broad-host-range RK2 vectors useful for high and low regulated gene expression levels in gram-negative bacteria," Plasmid, 38 (1): 35-51 (1997)) was required from National BioResource Project (NBRP). All the *E. coli* genes were cloned from cDNA of *E coli*. MG1655 strain from ATCC and amorphadiene synthase was codon optimized and synthesized from Genscript. The CLIVA method was used to generate mutant promoters and to combine multiple modules for amorphadiene production in to one (pAC) vector. *E. coli* XL10-Gold strain (Invitrogen) or DH10B strain (NEB) was used for plasmid construction. *E. coli* K-12 MG1655 DE3 was from Ajikumar, P. K., et al., "Isoprenoid pathway optimization for Taxol precursor overproduction in *Escherichia coli*," Science, 330 (6000): 70-74 (2010) and *E. coli* BL21-Gold (DE3) strain was from Stratagene. Both strains carrying T7 RNA polymerase were used for isoprenoid production.

TABLE 2

Plasmids used in this study

Part I: Plasmid composition

| Name | Vector | Promoter | Genes |
|------|--------|----------|-------|
| pETK | pETK | T7 | non |
| pETK-T7-SIDF | pETK | T7 | dxs-idi-ispD-ispF |
| pAC-LYC | pAC | Constitutive | crtE-crtB-crtI |
| pBAD-crtEBI | pBAD | pBAD | crtE-crtB-crtI |
| pAC-BAD-crtEBI | pAC | pBAD | crtE-crtB-crtI |
| pAC-T7-crtEBI | pAC | T7 | crtE-crtB-crtI |
| pAC-T7-ADS | pAC | T7 | ADS |
| pAC-T7-AA | pAC | T7 | ADS-ispA |
| pETK-T7-eGFP | pETK | T7 | eGFP |
| pETK-T7-dxs | pETK | T7 | dxs |
| pETK-T7-idi | pETK | T7 | idi |
| pETK-T7-IDF | pETK | T7 | idi-ispD-ispF |
| pETK-T7-t-dxs | pETK | T7 | N.dxs |
| pETK-T7-t-idi | pETK | T7 | N.idi |
| pETK-TM1/2/3-SIDF | pETK | TM1/TM2/TM3 | dxs-idi-ispD-ispF |
| pAC-TM1/2/3-crtEBI | pAC | TM1/TM2/TM3 | crtE-crtB-crtI |
| pETK-TM1/2/3-dxs | pETK | TM1/TM2/TM3 | dxs |
| pAC-TM1/2/3-ADS | pAC | TM1/TM2/TM3 | ADS |
| pAC-TM1/2/3-AA | pAC | TM1/TM2/TM3 | ADS-ispA |
| pRepressor | pETK | Constitutive | lacI |
| RK2A-T7-IDF | Rk2A | T7 | idi-ispD-ispF |
| RK2A-TM1/2/3-IDF | RK2A | TM1/TM2/TM3 | idi-ispD-ispF |
| pAC-TM1/2/3-dxs- | pAC | TM1/TM2/TM3 | dxs |
| TM1/2/3-IDF- | | TM1/TM2/TM3 | idi-ispD-ispF |
| TM1/2/3-ADS | | TM1/TM2/TM3 | ADS |
| pETK-T7-SBR | pETK | T7 | hmgS-aroB-hmgR |
| pETK-TM1/2/3-SBR | pETK | TM1/TM2/TM3 | hmgS-aroB-hmgR |
| RK2A-T7-KKDI | Rk2A | T7 | MVK-PMVK-MVD-idi |
| RK2A-TM1/2/3-KKDI | Rk2A | TM1/TM2/TM3 | MVK-PMVK-MVD-idi |
| pAC-TM1/2/3-SBR- | pAC | TM1/TM2/TM3 | hmgS-aroB-hmgR |
| TM1/2/3-KKDI- | | TM1/TM2/TM3 | MVK-PMVK-MVD-idi |
| TM1/2/3-AA | | TM1/TM2/TM3 | ADS-ispA |
| pETK- T7-eGFP-tag1 | pETK | T7 | eGFP-tag1 |
| pETK- T7-eGFP-tag2 | pETK | T7 | eGFP-tag2 |
| pETK- T7-eGFP-tag3 | pETK | T7 | eGFP-tag3 |
| pETK- TM1/2/3-eGFP-tag1 | pETK | TM1/TM2/TM3 | eGFP-tag1 |
| | | | eGFP-tag2 |
| pETK- TM1/2/3-eGFP-tag2 | pETK | TM1/TM2/TM3 | eGFP-tag3 |
| pETK- TM1/2/3-eGFP-tag3 | pETK | TM1/TM2/TM3 | |

Part II: Plasmid construction

| Name | Construction |
|------|-------------|
| pETK | Replace the Ampicillin resistance gene of pET-11a with kanamycin resistance gene by ligation |
| pETK-T7-SIDF | Inserted into pETK one by one by ligation |
| pAC-LYC | From paper [13] |
| pBAD-crtEBI | Amplified from pAC-Lyc and inserted into pBAD-B one by one by ligation |
| pAC-BAD-crtEBI | Replace the vector of pBAD-crtEBI with pAC vector by CLIVA method |
| pAC-T7-crtEBI | Replace the promoter of pAC-BAD-crtEBI with T7 promoter by ligation |
| pAC-T7-ADS | Replace the gene of pAC-T7-crtEBI with ADS by ligation |
| pAC-T7-AA | Replace the gene of pAC-T7-crtEBI with ADS and ispA by ligation |
| pETK-T7-eGFP | Amplified from pIRES-eGFP and inserted into pETK by ligation |
| pETK-T7-dxs | Inserted into pETK by ligation |
| pETK-T7-idi | Inserted into pETK by ligation |
| pETK-T7-IDF | Inserted into pETK one by one by ligation |

TABLE 2-continued

Plasmids used in this study

| | |
|---|---|
| pETK-T7-t-dxs | Remove the RBS and start codon of pETK-T7-dxs |
| pETK-T7-t-idi | Remove the RBS and start codon of pETK-T7-idi |
| pETK-TM1/2/3-SIDF | Modify the promoter of pETK-T7-SIDF by CLIVA method |
| pAC-TM1/2/3-crtEBI | Modify the promoter of pAC-T7-crtEBI by CLIVA method |
| pETK-TM1/2/3-dxs | Modify the promoter of pETK-T7-dxs by CLIVA method |
| pAC-TM1/2/3-ADS | Modify the promoter of pAC-T7-ADS by CLIVA method |
| pAC-TM1/2/3-AA | Modify the promoter of pAC-T7-AA by CLIVA method |
| pRepressor | Remove the T7 promoter, RBS and T7 terminator of pETK |
| RK2A-T7-IDF | Replace the vector of pETK-T7-IDF with RK2A vector by CLIVA method |
| RK2A-TM1/2/3-IDF | Modify the promoter of RK2A-T7-IDF by CLIVA method |
| pAC-TM1/2/3-dxs-TM1/2/3-IDF-TM1/2/3-ADS | Combine the modules amplified from: pETK-TM1/2/3-dxs, pAC-TM1/2/3-ADS and RK2A-TM1/2/3-IDF into pAC vector by CLIVA method |
| pETK-T7-SBR | The Yeast genes (*Saccharomyces cerevisiae*) were inserted into pETK one by one by ligation |
| pETK-TM1/2/3-SBR | Modify the promoter of pETK-T7-SBR by CLIVA method |
| RK2A-T7-KKDI | The Yeast genes (*Saccharomyces cerevisiae*) were inserted into RK2A-T7 one by one by ligation |
| RK2A-TM1/2/3-KKDI | Modify the promoter of RK2A-T7-KKDI by CLIVA method |
| pAC-TM1/2/3-SBR-TM1/2/3-KKDI-TM1/2/3-AA | Combine the modules amplified from: pETK-TM1/2/3-SBR, pAC-TM1/2/3-AA and RK2A-TM1/2/3-KKDI into pAC vector by CLIVA method |
| pETK- T7-eGFP-tag1 | Inserted into pETK by ligation. Tag1 was amplified from crtE. |
| pETK- T7-eGFP-tag2 | Inserted into pETK by ligation. Tag2 was amplified from crtE. |
| pETK- T7-eGFP-tag3 | Inserted into pETK by ligation. Tag3 was amplified from crtE. |
| pETK- TM1/2/3-eGFP-tag1 | Modify the promoter of pETK- T7-eGFP-tag1 by CLIVA method |
| pETK- TM1/2/3-eGFP-tag2 | Modify the promoter of pETK- T7-eGFP-tag2 by CLIVA method |
| pETK- TM1/2/3-eGFP-tag3 | Modify the promoter of pETK- T7-eGFP-tag3 by CLIVA method |

Culture Medium and Growth Conditions

2xPY medium was prepared: peptone 20 g/L, yeast extract 10 g/L and NaCl 10 g/L, adjust pH=7.0, autoclaved at 121° C. for 20 mins. An additional 10 g/L glycerol (for DXP pathway) or glucose (for MVA pathway), 50 mM HEPES buffer (pH=7.4) and 0.5% Tween 80 was added to 2xPY medium for isoprenoid production. The antibiotics were added at various concentrations to maintain the selection: ampicillin (100 mg/L), chloramphenicol (34 mg/L) and kanamycin (50 mg/L). 1% (v/v) of overnight grown cell culture was inoculated and cells were grown at 28° C. with 300 RPM shaking for isoprenoids production. The inducers (L-arabinose or IPTG) were added when the cells' optical density at 600 nm reached the range of 0.6~0.8. For lycopene production, 1 ml of cells was grown for 48 hours in 14 mL BD Falcon™ tube. For amorphadiene, 0.8 ml of cells together with 0.2 ml of dodecane were grown for 72 hours in 14 mL BD Falcon™ tube (Newman, J. D., et al., "High-level production of amorpha-4,11-diene in a two-phase partitioning bioreactor of metabolically engineered *Escherichia coli*," *Biotechnol. Bioeng.*, 95 (4): 684-91 (2006)).

Lycopene and Amorphadiene Assay

Intracellular lycopene content was extracted from 20-100 μL (depending on the content of lycopene in cells) of bacterial culture. The cell pellet was washed for about 30~40 min and completely resuspended in 100 μL D.D. H₂O. 20 μL of suspension was then extracted in 180 μL of acetone at room temperature for about 15 min with continuous vortexing and centrifuged at 2,800 g for 3 mins. The lycopene content in the supernatant was quantified through absorbance at 472 nm by microplate reader (Spectra Max 190, Molecular Devices) and concentrations were calculated through a standard curve. Amorphadiene was quantified by gas chromatography/mass spectrometry (GC/MS) by scanning of 189 and 204 m/z ion, using trans-caryophyllene as internal control and in vitro synthesized amorphadiene as standard curve.

RNA Purification and cDNA Synthesis

Total RNA from *E. coli* was prepared using TRIzol® reagent (Invitrogen) according to the manufacturer's instructions. Total RNA was collected from samples in quadruplicate at each treatment time point. RNA concentration was quantified using a NanoDrop ND-1000 spectrophotometer (Thermo Scientific), and the 260/280 and 260/230 ratios were examined for protein and solvent contamination. The integrities of all RNA samples were confirmed by formaldehyde agarose gel. 200 ng of total RNA were treated with RQ1 RNAse-free DNAse (Promega) and reverse transcribed in a total volume of 10 μL containing ImpromII (Promega) for 60 min at 42° C. according to the manufacturer's instructions. The reaction was terminated by heating at 70° C. for 10 min.

Reverse Transcription and Quantitative PCR (RT-qPCR)

The cDNA levels were then analyzed using a BioRad iCycler 4 Real-Time PCR Detection System (Bio-Rad) with SYBR Green I detection. Each sample was measured in duplicate in a 96-well plate (Bio-Rad) in a reaction mixture (25 μL final volume) containing 1x Xtensa Buffer (bioworks), 200 nM primer mix, 2.5 mM MgCl2, 0.75 U of iTaq DNA polymerase (iDNA). qPCR was performed with an initial denaturation of 3 min at 95° C., followed by 40 cycles of 20 s at 95° C., 20 s at 60° C., and 20 s at 72° C. The primers used for real time PCR were given in "Table 3". And the reference genes used for real time PCR were cysG. The copies of the genes in cDNA were calculated with a standard curve prepared from plasmid DNA and presented as copy per copy of cysG.

TABLE 3

| qPCR primers used in this study (SEQ ID NOs: 13-28) | | |
| --- | --- | --- |
| Gene | Forward primer | Reverse primer |
| dxs | CGGCTATCACTATAACGATG G | CACGACGCTTCACAATGC |
| crtE | GTAAAGCGGGCGTTTCG | GCCAGCAGCATCAGC |
| idi | TGTATTACACGGTATTGATG CCACG | AGCTGGGTAAATGCAGATAATC GTT |
| cysG | TTGTCGGCGGTGGTGATGTC | ATGCGGTGAACTGTGGAATAAA CG |
| eGFP | GACCACTACCAGCAGAACAC C | GACCATGTGATCGCGCTT |
| tag1 | CACGCATCGCAAGGCTGA | TGGCTGGCCTGTTACCTGA |
| tag2 | GGTCAGCCCACTACCCACAA | CCCAACGGAGGCAAGGAT |
| tag3 | CGTCCTTATTGCGATCTTTAC CG | CAGGCGTTTCAACTGCTGG CG |

In Vitro Transcription

Different modules (TM1/TM2/TM3-eGFP-tag1/2/3) were amplified from plasmid. Their concentrations were quantified using a NanoDrop ND-1000 spectrophotometer (Thermo Scientific) and in the reactions, the modules were added in equal molar. In total, 50 ng of DNA were added into a Sul in vitro transcription reaction using T7 RNA polymerase (12.5u) and rNTP (0.5 mM each) from NEB according to the manufacturer's instructions. The reactions were carried out at 37° C. for 2 hours and terminated by adding 50 ul of DEPC treated water with 0.5 mM EDTA. 4 µL of the RNAs were then used for RT-qPCR according the described protocols.

Example II: Combinatorial Engineering of 1-Deoxy-D-Xylulose 5-Phosphate Pathway Using Cross-Lapping In Vitro Assembly (CLIVA) Method The ability to assemble multiple fragments of DNA into a plasmid in a single step is invaluable to studies in metabolic engineering and synthetic biology. Using phosphorothioate chemistry for high efficiency and site specific cleavage of sequences, a novel ligase independent cloning method (cross-lapping in vitro assembly, CLIVA) was systematically and rationally optimized in *E. coli*. A series of 16 constructs combinatorially expressing genes encoding enzymes in the 1-deoxy-D-xylulose 5-phosphate (DXP) pathway were assembled using multiple DNA modules. A plasmid (21.6 kb) containing 16 pathway genes, was successfully assembled from 7 modules with high efficiency (2.0×103 cfu/µg input DNA) within 2 days. Overexpressions of these constructs revealed the unanticipated inhibitory effects of certain combinations of genes on the production of amorphadiene. Interestingly, the inhibitory effects were correlated to the increase in the accumulation of intracellular methylerythritol cyclodiphosphate (MEC), an intermediate metabolite in the DXP pathway. The overexpression of the iron sulfur cluster operon was found to modestly increase the production of amorphadiene. This study demonstrated the utility of CLIVA in the assembly of multiple fragments of DNA into a plasmid which enabled the rapid exploration of biological pathways.

Synthetic biology has provided tools for the design and construction of biological systems which enabled the metabolic engineering of cellular pathways for the production of desirable compounds. For an example, bacteria can now be engineered to efficiently produce a class of natural products commonly found in plants—the isoprenoids. Some of these natural compounds include high value pharmaceutical products like the antimalarial drug, Artemisinin, and the anticancer drug, Taxol. To construct such bacteria, certain combinations of genes encoding a metabolic pathway are required to be overexpressed. The construction of such genetically engineered collection of strains is challenging. Here, we systematically and rationally developed a new method that allows the rapid construction of large recombinant DNAs from multiple fragments in a single step. With the method, the pathway synthesizing precursors for isoprenoids was combinatorially engineered to produce amorphadiene—the precursor of Artemisinin. This study revealed the unanticipated effects of certain combinations of genes. The inhibitory effects were further found to be correlated with the intracellular accumulation of an intermediate metabolite and the co-expression of genes supplying cofactors for the downstream enzymes increased productivity. The method described herein is invaluable to studies in metabolic engineering and synthetic biology.

Synthetic biology and metabolic engineering require convenient, robust and universal tools to manipulate genetic materials. As such, a demand is to assemble multiple genetic components including sequences encoding enzymes, functional fusion tags and control elements (promoters, terminators and ribosome binding sites). The commonly used restriction enzymes and in vitro ligation based sequential cloning methods are often limited by the availability of unique restriction sites and are time consuming. Furthermore, single stranded DNA (ssDNA) overhangs generated by restriction enzymes are typically 2-8 nucleotides which exhibit poor annealing efficiencies and have limited use in assembling multiple large DNA fragments in a single step.

To address these challenges, several sequence independent methods, generating long ssDNA overhangs or using double stranded PCR products with long homologous sequences, have been developed for the assembly of large DNA inserts into vectors. Only a few of these approaches have reported the assembly of multiple (>3) DNA fragments in a single step. Methods such as the T4 DNA polymerase based sequence and ligation-independent cloning (SLIC), phosphorothioate-based ligase-independent gene cloning (PLICing) and others have only demonstrated the construction of plasmids of less than 8 kb. Various attempts have been made to meet the increasing demand to assemble several large fragments of DNA inserts into plasmids of >10 kb. A isothermal in vitro assembling method with synthetic oligonucleotides was used to assemble a 16.3 kb construct from seventy-five fragments of DNAs and the assembly of a 24 kb plasmids from four separate fragments. In addition, using yeast in vivo recombination system, a 582 kb *Mycoplasma genitalium* genome was constructed from synthetic DNA oligonucleotides in several steps. The yeast system has also been successfully used for the one step assembly of a 19 kb fragments into a plasmid or yeast chromosome. With these examples, homologous overhang sequences with lengths of 100-500 base pairs were required to increase the assembly efficiency. This can be a significant challenge where suitable pre-existing sequences in the parental or chemically synthesized templates are required which can restrict the applicability and incur high-cost of synthesis.

Furthermore, these approaches are also time consuming and labor intensive, hence, are not suited for routine cloning projects.

This example describes the development of a reliable, scalable and robust cloning method (cross-lapping in vitro assembly, CLIVA) for the rapid construction of large recombinant DNA from multiple fragments in a single step. This approach exploits the unique properties of phosphorothioate modified nucleotides where highly efficient and site specific cleavage is achieved using iodine in an ethanolic solution (Nakamaye, K. L., et al., "Direct sequencing of polymerase chain reaction amplified DNA fragments through the incorporation of deoxynucleoside alpha-thiotriphosphates," *Nucleic Acids Res.,* 16:9947-9959 (1988); Gish, G., and Eckstein, F., "DNA and RNA sequence determination based on phosphorothioate chemistry," *Science,* 240:1520-1522 (1988)). Recently, the use of such phosphorothioate chemistry was demonstrated for the assembly of multiple small protein domains (Blanusa, M., et al., "Phosphorothioate-based ligase-independent gene cloning (PLICing): An enzyme-free and sequence-independent cloning method," Anal. Biochem., 406:141-146 (2010); Marienhagen, J., et al., P"hosphorothioate-based DNA recombination: an enzyme-free method for the combinatorial assembly of multiple DNA fragments," *Biotechniques,* 0:1-6 (2012)). Unique to the CLIVA method is a novel cross-lapping design which allows the generation of long homologous overhang sequences (36-38 bases) by cleavage of optimally positioned phosphorothioate modified nucleotides and the use of selective cations resulting in a highly efficient assembling process. To demonstrate the utility of this method, we constructed 16 plasmids of 7.8 kb to 21.6 kb in size, encoding various combinations of genes in the 1-Deoxy-D-xylulose 5-phosphate (DXP) pathway in *E. coli.* To our knowledge, this is the first report of the successful assembly of large constructs containing multiple genes using an enzyme independent in vitro method to engineer multi-enzyme pathways in a short duration.

Isoprenoids are a large and diverse class of natural products (more than 55,000) derived from five-carbon isoprene units. Some are fragrances, insecticides, nutraceuticals and pharmaceuticals, while the functions of the vast majority of the isoprenoids remain to be determined. Due to the structural complexities of many of these compounds, e.g., Artemisinin and Taxol, de novo total chemical synthesis is impractical. Metabolic engineering of microbes is a promising alternative and has been intensively explored by manipulating the 1-deoxy-D-xylulose-5-phosphate (DXP) or the mevalonate (MVA) pathway. The DXP pathway displays a more balanced redox utility as compared to the MVA pathway in vivo. In *E. coli,* a few empirically selected enzymes (dxs, idi, ispD, ispF) are thought to be the limiting steps in the DXP pathway and increasing the expression levels of these enzymes have been shown to improve isoprenoid production.

Figures 22A, 22B:
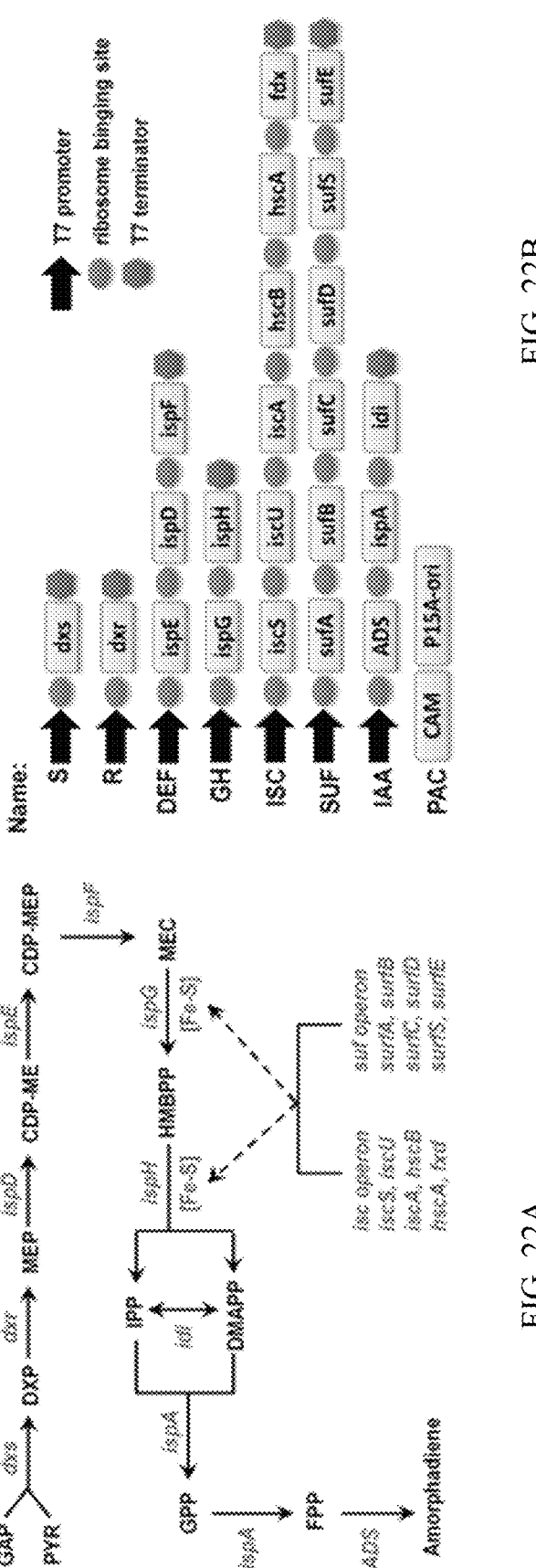
FIGS. 22A-22B illustrate assembly of DXP pathway.

In this study, the effects of various combinations of the enzymes in the DXP pathway in providing precursors to downstream production of amorphadiene, the precursor for antimalarial drug artemisinin (Liu, C., et al., "Artemisinin: current state and perspectives for biotechnological production of an antimalarial drug," *Appl. Microbiol. Biotechnol.,* 72:11-20 (2006)), was systematically investigated for the first time (FIG. 22A). The CLIVA method enabled the assembly of multiple plasmids containing various combinations of genes rapidly. Metabolic profiling using ultra-performance liquid chromatography mass spectrometry (UPLC-MS) (Zhou, K., et al., "Metabolite profiling identified methylerythritol cyclodiphosphate efflux as a limiting step in microbial isoprenoid production," *PLOS One,* 7: e47513 (2012)) identified the accumulation of intracellular MEC (one of the DXP pathway intermediate) as a limiting factor for isoprenoid production. The overexpression of iron sulfur cluster (Isc) operon, which supplied the cofactors for the function of two succeeding enzymes downstream of MEC (ispG and ispH) (FIG. 22A), was found to modestly enhance the production of amorphadiene.

Results

Design of CLIVA

PCR has been used to produce overlapping homologous sequences by adding extraneous tag sequences to the gene specific primers. With such a design, the homologous sequences are limited to the length of the tags. In order to increase the assembly efficiency, we designed the tags to be homologous to the gene specific sequences (FIG. 20A). This cross-lapping design allowed us to increase the length of the homologous sequences at each junction as compared to conventional strategies. Besides, other than modifying all the bases in the homologous sequences which increased the cost of primer synthesis, we explored the possibility of decreasing the modification frequency (number of phosphothioate modification per oligonucleotide) while maintaining a high efficiency of assembly (FIG. 20A). By the use of certain cations, the efficiency of the assembly process was substantially increased and this has enabled the construction of large plasmids from multiple fragments in one step.

In order to demonstrate the utility of this method, we constructed a series of plasmids carrying multiple genes of a metabolic pathway. As shown in FIG. 20B, all the pathway modules as well as a vector module containing the origin of replication and antibiotic resistant gene were first amplified from the parental plasmids using a pair of cross-lapping primers and subsequently treated with a solution of ethanolic iodine as described in "MATERIAL AND METHODS". The assembly was then carried out in the optimal condition with equal molar of each DNA module fragment (see below).

Optimization of CLIVA

The construction of a 7.1 kb PAC-SIDF plasmid was initially used as a model for identifying suitable designs and optimal conditions for CLIVA. The PAC-SIDF plasmid was generated by combining two modules amplified from different sources: the PAC vector (2.8 kb) consisting of P15A origin of replication and chloramphenicol resistant gene (FIG. 22B) from a pre-existing pAC-lyc plasmid and SIDF module (4.3 kb) containing four 1-Deoxy-D-xylulose 5-phosphate (DXP) pathway enzymes (dxs, idi, ispD, ispF, FIG. 22A) from a pre-existing pET-dxs-idi-ispDF plasmid (Tyo, K. E., et al., "Stabilized gene duplication enables long-term selection-free heterologous pathway expression," *Nat. Biotechnol.,* 27:760-765 (2009)). All the primers used in the optimization process were listed in Table 5 where the PAC-F/PAC-R and SIDF-F/SIDF-R were the gene specific sequences targeting at pAC-lyc plasmid and pET-dxs-idi-ispDF plasmid.

Figures 21A, 21B, 21C, 21D:
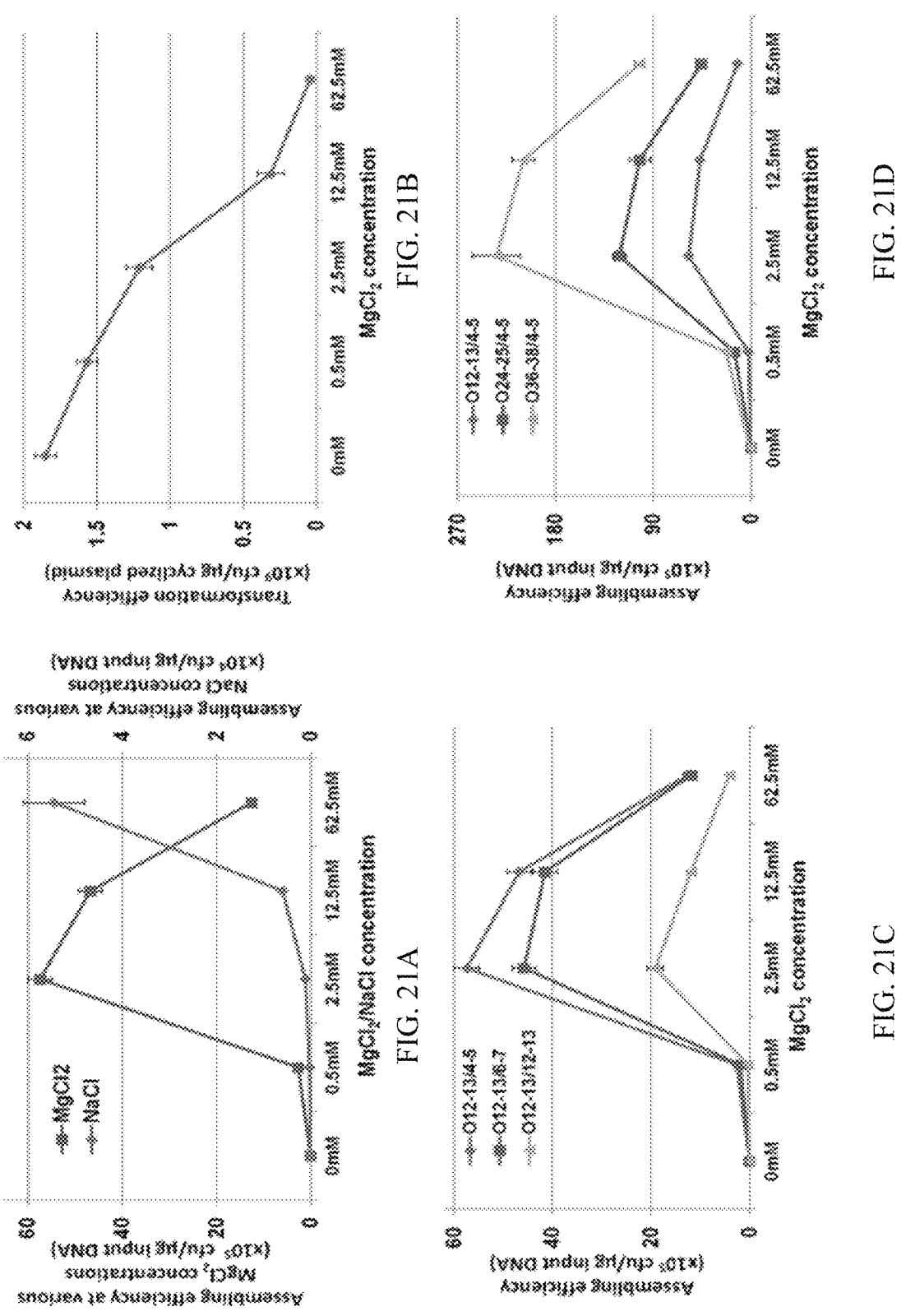
FIGS. 21A-21D illustrate optimization of CLIVA method.
Figure 26:
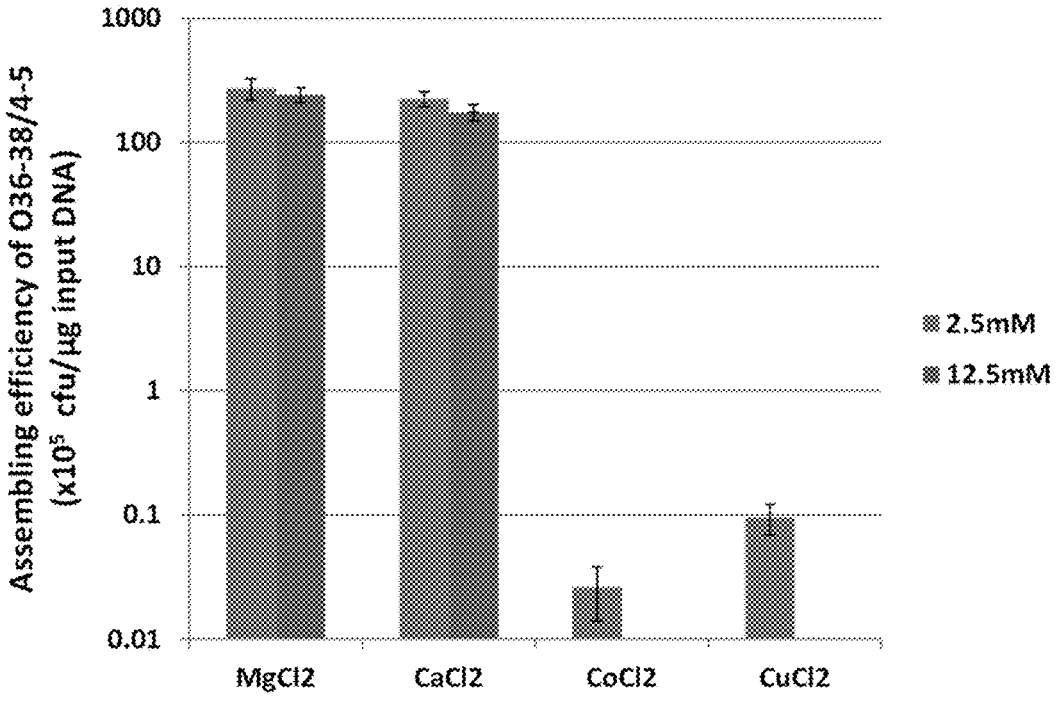
FIG. 26 illustrates different cations' effects on the assembly efficiency. The assembling efficiencies of PAC-SIDF plasmid with 036-38/4-5 design (36-38 bases overlap with phosphorothioate modification at each 4-5 bases) at 2.5 mM (left) or 12.5 mM (right) of $MgCl2$, $CaCl_2$), $CoCl_2$ or $CuCl_2$ were presented. All the experiments were done at triplicates and the standard error were presented in the figure.

Ionic strength affects DNA hybridization (Lang, B. E., and Schwarz, F. P., "Thermodynamic dependence of DNA/DNA and DNA/RNA hybridization reactions on temperature and ionic strength," Biophys. Chem., 131:96-104 (2007)). As cations can reduce charge repulsion between the negatively charged phosphodiester backbones of double stranded DNA, we sought to investigate the assembly efficiency in relation to the concentrations of $MgCl_2$ or NaCl. The assembly efficiency increased dramatically with the addition of salts and the divalent cation ($Mg^{2+}$) resulted in much higher enhancement (FIG. 21A). With respect to $Na^+$, there was a positive correlation between the ionic concentration and the assembly efficiency. With Mg2+, a decrease in the assembly efficiency was observed at high concentrations. A limitation in using high concentrations of salts (NaCl or MgCl$_2$) was that these reaction mixtures were incompatible with the use of electroporation for transformation. This proposal was consistent with the observation of the severe suppression of transformation efficiency at high MgCl2 concentration (62.5 mM) (FIG. 21B). Thus, the optimum MgCl2 concentration was identified as 2.5 mM. We also tested other divalent ions (CuCl$_2$, CaCl$_2$, and CoCl$_2$) and found that Ca2+ acted similarly to Mg2+, while Co2+ and Cu2+ were found to be significantly poorer (FIG. 26). This was possibly due to the toxicity of Co2+ and Cu2+ ions at high concentrations.

Existing methods that generate ssDNA with phosphorothioate chemistry have every base of the overlap sequence chemically modified, which is cost prohibitive for long overlapping sequences (Blanusa, M., et al., "Phosphorothioate-based ligase-independent gene cloning (PLICing): An enzyme-free and sequence-independent cloning method," *Anal. Biochem.,* 406:141-146 (2010); Marienhagen, J., et al., "Phosphorothioate-based DNA recombination: an enzyme-free method for the combinatorial assembly of multiple DNA fragments," *Biotechniques,* 0:1-6 (2012)). We hypothesized that it was unnecessary to cleave the overlapping sequence into single bases; instead, by cleaving the nucleotide at several discrete sites into smaller fragments, the assembly should work equally well. We then tested this hypothesis using four types of 12-13 bases overlap designs: O12-13/1, O12-13/4-5, O12-13/6-7 and O12-13/12-13 with different positions of the sequences modified with phosphorothioate where the modifications at positions were 1 base apart, 4-5 bases apart, 6-7 bases apart or 12-13 bases apart, respectively (Table 5). Unexpectedly, amplification using O12-13/1 primer pairs (modification inserted at every base) yielded extremely low amount of amplicon and was not used for further studies. The exact reason for this poor amplification is currently unknown. Nonetheless, the O12-13/4-5 design was successfully amplified showed a high assembly efficiency. A slightly lower assembly efficiency was observed when using the O12-13/6-7 design and even lesser still with the O12-13/12-13 design (FIG. 21C). It is worthy to note that with the O12-13/12-13 design where a single modification was incorporated, the cleavage resulted in a fragment of the DNA which was identical to the overlap sequence and hence, may have competed for annealing. So this arrangement would result in a lower efficiency in assembly, consistent with the observation in FIG. 21C. Increasing the modification frequency greater than one in 4-5 bases apart did not substantially improve the efficiency of assembly as compared to one in 6-7 bases.

Another critical parameter for the assembly of multiple DNA fragments is the length of the overlaps that determines the specificity as well as the efficiency of the annealing. As predicted, when compared to short overlaps (12-13 bases), the assembly efficiency increased with longer overlapping segments (36-38 bases) by as much as 3 fold (FIG. 21D). With the increasing number of pathway modules to assemble, it is critical to have high assembly efficiency at each junction.

Figure 27:
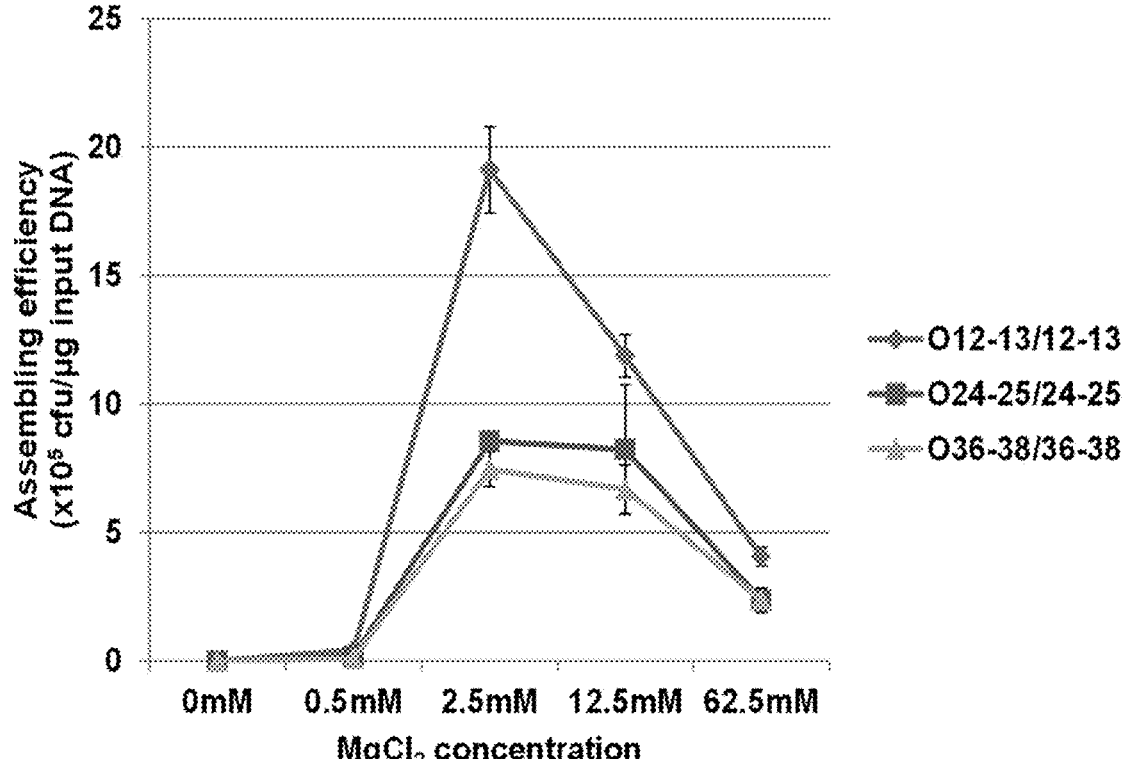
FIG. 27 illustrates the assembly efficiency of overlap designs with single phosphorothioate modification. O12-13/ 12-13, O24-25/24-25, O36-38/36-38:12-13 bases, 24-25 bases, 36-38 bases homologous sequences with one phosphorothioate modification. All the experiments were done at triplicates and the standard error were presented in the figure.

Extending the study, the assembling efficiencies of designs with only a single phosphorothioate modification (O12-13/12-13, O24-25/24-25 and O36-38/36-38) were examined (FIG. 27). With this arrangement, the design with longer overlap sequences after cleavage (O24-25/24-25 where the overlap was 24-25 bases) showed lower efficiency of assembly than a shorter one (O12-13/12-13 where the overlap was 12-13 bases). In addition, an even longer overlap (the O36-38/36-38 design where the overlap was 36-38 bases) was even poorer. Thus, with single phosphorothioate modification, the efficiency of assembly was related to the length of the cleaved product whereby the fragmented pieces of DNA should be short so as not to interact with the overlap sequences. Thus, the O36-38/4-5 design was suitable for the assembly of multi-components with high efficiency, while the O12-13/12-13 design was sufficiently efficient and cost effective, replacing the use of restriction enzyme and ligation based method for routine tasks.

Constructions of Plasmids Using CLIVA Method

Next, we used the CLIVA method to assemble a series of plasmids consisting of various combinations of modules containing the genes of the 1-Deoxy-D-xylulose 5-phosphate (DXP) pathway (Rohmer, M., "The discovery of a mevalonate-independent pathway for isoprenoid biosynthesis in bacteria, algae and higher plants," *Nat. Prod. Rep.,* 16:565-574 (1999)) and for amorphadiene production (FIG. 22A). In addition, two operons, ISC (iron-sulfur cluster (Isc) operon) and SUF (sulfur mobilization (Suf) operon), containing the proteins necessary for Fe—S cluster (Py, B., and Barras, F., "Building Fe—S proteins: bacterial strategies," Nat. Rev. Microbiol., 8:436-446 (2010)) assembly in *E. coli* were also constructed (FIG. 22A). Details of the modules and their abbreviations were presented in FIG. 22B. Fragments of treated DNAs were mixed and transformed into *E. coli* for the one step assembly of these genes (FIG. 20B) and the correct clones were identified by quantitative colony PCR as described in "MATERIAL AND METHODS". With each construct, two randomly selected positive clones were further confirmed by restriction mapping and at least one of these was verified by sequencing. The sequencing results covered all the sequences encoding the junctions (the overlap sequence between the modules) as well as more than 50% of the sequences in the plasmid. No change in the sequences was observed, indicative of the high fidelity of amplification and high specificity of cleavage. As expected, the efficiency decreased with increasing number of fragments (Table 4). However, even with the largest plasmid (21.6 kb, S-R-DEF-GH-ISC-IAA-PAC plasmid from 6 modules) assembled, the efficiency was reliably high (~2.0×10$^3$ cfu/μg input DNA). The false positive colonies resulting in lower accuracy of assembly were largely due to the existence of plasmids with incomplete pathway modules (demonstrated by quantitative colony PCR and restriction mapping, data not shown).

Overexpression of GH and R-DEF Inhibited Amorphadiene Production

Figures 23A, 23B:
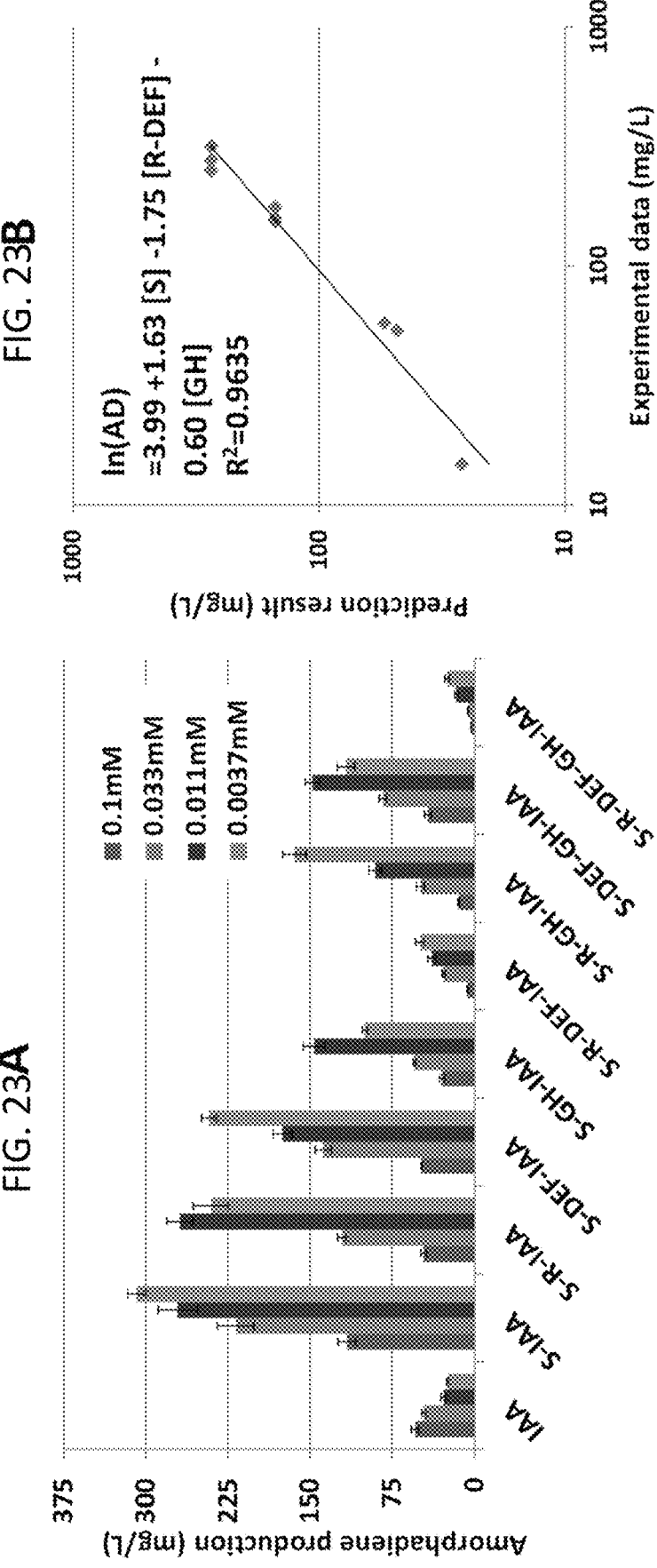

Next, the various combinations of pathway genes with the essential module (IAA) containing the heterologous amorphadiene synthase were tested for amorphadiene production. High induction resulted in lower production of isoprenoids (FIG. 23A, different IPTG inductions). Comparing constructs at their optimal induction levels, as expected, the expression of the first committed step (dxs-module S) enhanced the amorphadiene production. However, the overexpression of the rest of the pathway genes in conjunction with the S and IAA modules had variable negative effects on productivity. Notably, the expression of GH module (ispG and ispH) as well as R (dxr)-DEF (ispD, ispE and ispF) modules led to a significant inhibition on the production (FIG. 23A). Consistent with the observations, a simple linear model correlating the pathway modules and amorphadiene yields at their optimal inductions revealed that the expression of GH module or the co-expression of R-DEF modules had negative impacts (FIG. 23B).

In order to investigate the changes in the levels of intracellular metabolic intermediates with the overexpression of the various modules, cells were harvested after 3 h of induction and the metabolites were quantified by UPLC-MS (FIGS. 23C-23J). The induction of the expression of the genes in any of the modules resulted in significant accumulation of intracellular MEC, indicative of a limitation in metabolite conversion with genes downstream, an observation in congruence with our previous observations. Interestingly, the overexpression of GH module did not fully convert MEC to the downstream metabolite IPP/DMAPP. Instead the metabolite HMBPP accumulated in all strains where the GH module was overexpressed (FIGS. 23G-23J). Other than that, the genes in the pathway upstream of MEC were functionally expressed as the accumulations of the metabolites were positively correlated with the expressed genes. Hence, the overexpression of dxs, the first and committed step in the DXP pathway, resulted in the accumulation of DXP (FIG. 23C, S-IAA). Similarly, the overexpression of dxs and dxr resulted in the accumulation of MEP (FIG. 23D, S-R-IAA) and the co-expression of S-R-DEF resulted in the high accumulation of MEC (FIG. 23E, S-R-DEF-IAA). Besides, higher expressions of these genes resulted in the parallel increases in activities (higher concentrations of accumulated intermediates).

Figures 24V, 24W, 24X:
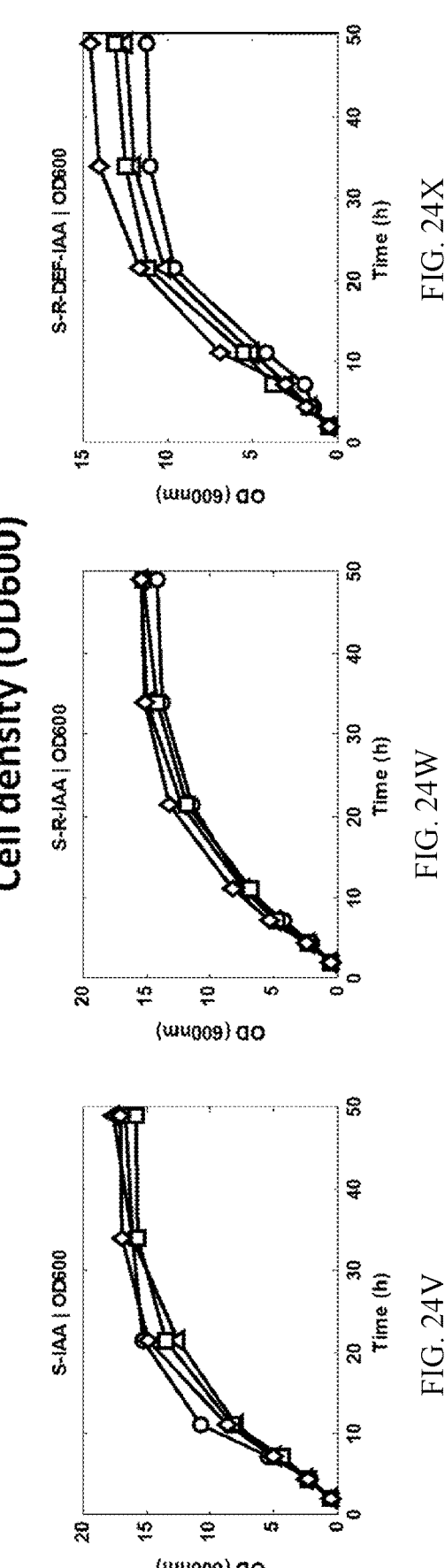
Figure 25:
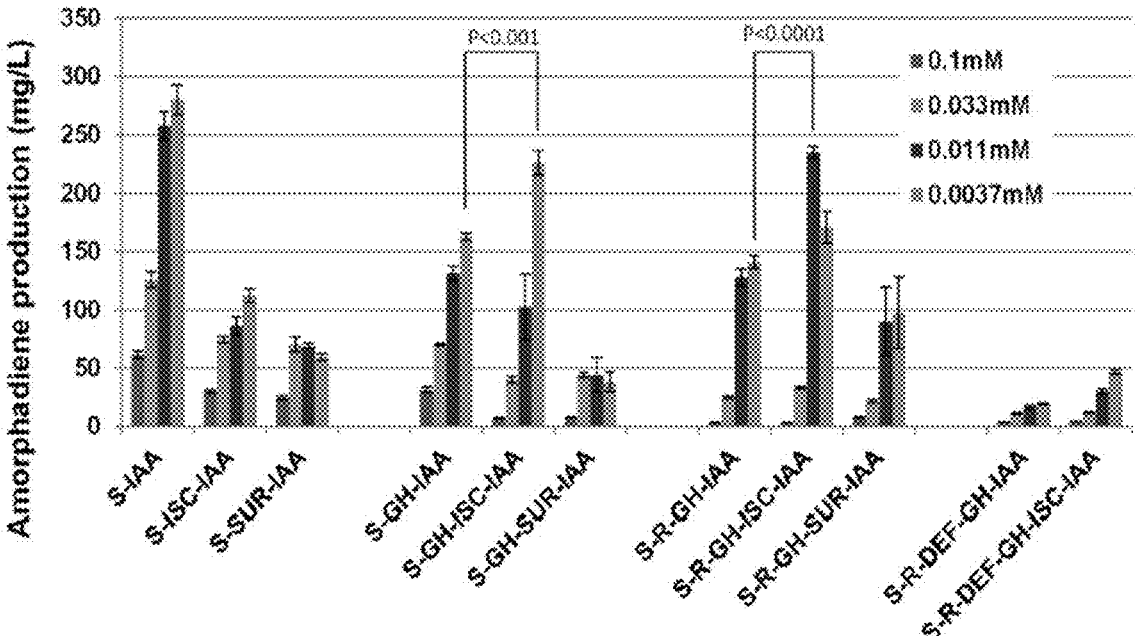
FIG. 25 illustrates the effects of Fe—S operons on the amorphadiene production. Different concentrations of IPTG were represented by bars with different colors. The experiment was repeated four times and the standard errors of four replicates were presented as error bars. The two tailed p-values of student's t-test were carried out to compare certain conditions and presented as P in the figure. For each data set on the X-axis, the IPTG concentrations are from highest (0.3 mm) to lowest (0.011 mm), from left to right.

Accumulation of Intracellular MEC was Inversely Correlated to Amorphadiene Productivity In order to further investigate the pathway, a kinetic study measuring the concentrations of intracellular, extracellular DXP metabolites and amorphadiene was carried out with strains harboring different modules. As expected, the induction of dxs resulted in a significant increase in the level of intracellular DXP in the strain with S-IAA modules (FIG. 24A, S-IAA|DXP). Curiously, extracellular level of DXP was also increased substantially albeit with different kinetics (FIG. 24J, S-IAA|DXP). Similarly, the expression of the S-R-IAA modules resulted in the accumulation of both intracellular and extracellular MEP (FIGS. 24E & 24O, S-R-IAA|MEP). With all three modules, MEC accumulated intracellularly and significantly more with the S-R-DEF-IAA modules. Intriguingly, the extracellular levels of MEC accumulated to similar levels and were inversely correlated to the inducer concentrations in strains carrying any of the three modules (FIGS. 24L, 24P, 24T, MEC). The inverse correlation of metabolite levels with the inducer concentration used was also observed with the production of amorphodiene. The S-R-DEF-IAA-PAC strain accumulated large quantities of intracellular MEC and yielded much less amorphodiene as compared to strains harboring the S-IAA or S-R-DEF-IAA modules (FIGS. 24L, 24T, MEC). Although high IPTG inductions yielded higher concentrations of intracellular intermediates initially (FIGS. 24A-24I, first 10 h), the relationship was reversed at later time points, especially with the highest induction (0.1 mM IPTG) (FIGS. 24A-24I, highly accumulated intermediates). Other metabolites (CDP-ME, IPP/DMAPP, GPP, FPP) were found to be accumulated at insignificant levels.

Overexpression of Fe—S Operons Modestly Increased Amorphodiene Productivity

An attempt was made to increase the activities of ispG and ispH (GH module) in converting MEC to the downstream metabolite IPP/DMAPP so as to increase amorphodiene production. As the essential cofactor for these two enzymes, the genes in the iron-sulfur (Fe—S) cluster pathways (iron-sulfur cluster (Isc) operon—iscS, isCU, iscA, hscB, hscA, fdx) and/or sulphur mobilization (Suf) operon (SUF module (surA, surB, surC, surD, surS, surE) (Py, B., and Barras, F., "Building Fe—S proteins: bacterial strategies," Nat. Rev. Microbiol., 8:436-446 (2010); Py, B., et al., "Fe—S clusters, fragile sentinels of the cell," Curr. Opin. Microbiol., 14:218-223 (2011)) were assembled using CLIVA and transformed into E. coli. Disappointingly, the overexpression of either operon together with S-IAA modules not only did not enhance but instead inhibited the production of amorphodiene (FIG. 25, 1-3 columns). The overexpression of Isc operon in other constructs together with GH module showed modest enhancements (FIG. 25, 4-8 columns).

Discussion

This study demonstrated the rapid assembly of large plasmids with an array of metabolic genes (21.6 kb plasmid with 16 genes) using a ligation independent cloning (CLIVA) method. These recombinant plasmids were then used to systematically investigate the effects of the various combinations of the enzymes in the DXP pathway in producing amorphadiene, the precursor for antimalarial drug artemisinin (FIG. 22A). Metabolic profiling using ultra-performance liquid chromatography mass spectrometry (UPLC-MS) (Zhou, K., et al., "Metabolite profiling identified methylerythritol cyclodiphosphate efflux as a limiting step in microbial isoprenoid production," PLOS One, 7: e47513 (2012)) identified the accumulation of intracellular MEC (one of the DXP pathway intermediate) as a potential negative contributor to isoprenoid production. The overexpression of the Isc operon, which supplied the cofactor for the function of two succeeding enzymes downstream of MEC (ispG and ispH) (FIG. 22A), was found to modestly increased the production of amorphadiene.

The manipulation of genetic material is a fundamental and routine requirement for engineering of biological systems where multiple genes are assembled and used to produce downstream products. The traditional in vitro ligation based cloning methods are sequence-dependent and are often not efficient in assembling multiple fragments of DNAs. Consequently, these limitations have been addressed with methods that assemble multiple DNA fragments with overlapping homologous sequences in a single step. Such in vitro assembling method or the yeast in vivo homolog recombination based DNA assembler method uses enzymes with exonuclease activities to generate ssDNA and other enzymes to repair the over-treated non-homologous ssDNA gaps. The use of multiple enzymes does not only incur cost but is also inefficient and time consuming. Based on the phosphorothioate chemistry that allows cleavage of DNA at specific sites, the enzyme-free CLIVA method provides robust performance for the one-step assembly of multiple DNA modules. Typically, the construction can be completed within 1-2 days, as compared to the more involved method of yeast recombination (1-2 weeks).

The novel design of the cross-lapping PCR primer pair (~40 bases) enabled high efficiency of amplification by PCR and efficient assembly of multiple DNA fragments. Unlike other studies, we found that phosphothioate modifications of every 4-5 bases intervals in the homologous sequences was sufficient to enable efficient cleavage and assembly of the sequences. The use of cations at optimal concentration was found to significantly enhance the assembly efficiency while maintaining high transformation efficiency. Even with a single phosphothioate modification, the assembly of two pieces of DNA fragments (~3-4 kb each) was highly efficient (~2.0×10$^6$ cfu/μg input DNA). This was far superior to the use of restriction enzymes and ligase (<10$^4$ cfu/μg input DNA for the same construct) in parallel studies. Hence, the CLIVA method can replace all routine recombinant DNA constructions with the use of just a single phosphothioate modification in each primer. The assembly of the 21.6 kb plasmid (S-R-DEF-GH-ISC-IAA-PAC) from 6 fragments of DNAs was sufficiently efficient ($\sim$2.0$\times$10$^3$ cfu/µg input DNA) and was completed in less than 2 days.

With constructs encoding multiple genes under the control of the same regulatory elements (T7 promoters and terminators), there were large amount of repeated sequences (200-300 bps) in regions between modules. As those perfect repeats may randomly anneal with each other during assembly, it was not surprising that the assembly of such multiple identical sequences resulted in numerous false positive clones which contained partially assembled sequences, an observation confirmed by quantitative colony PCR and restriction analysis. The use of the same regulatory elements to control multiple modules is predicted to be even more challenging for recombination based methods which are known to selectively rearrange repeated sequences in vivo (Shao, Z., et al., "DNA assembler, an in vivo genetic method for rapid construction of biochemical pathways," *Nucleic Acids Res.*, 37: e16 (2009)).

The S-R-DEF-IAA-PAC strain resulted in lesser yield of amorphadiene as compared to the other strains (S-IAA-PAC or S-R-IAA-PAC) which encode fewer numbers of genes in the pathway. The overexpressions of this poor performing construct resulted in transient accumulations of high levels of intracellular MEC but yet showed similar extracellular levels with the other modules. The inverse relationship of the levels of intracellular MEC and the downstream metabolite productivity suggests an inhibitory role of MEC in regulating isoprenoid production, possibly due to the increase in oxidative stress in the cell. Recently, MEC was also identified as a signaling molecule that induces stress-responsive genes in plant (Xiao, Y., et al., "Retrograde signaling by the plastidial metabolite MEcPP regulates expression of nuclear stress-response genes," *Cell*, 149: 1525-1535 (2012)), consistent with an involvement in stress response. Whether such stress response mechanism occurs in these strains remains to be determined.

The overexpression of module (GH) containing ispG and ispH resulted in the accumulation of HMBPP and yet did not increase amorphodiene production as would have been anticipated. A possibility is the limitation in the co-factor system (Py, B., and Barras, F., "Building Fe—S proteins: bacterial strategies," *Nat. Rev. Microbiol.*, 8:436-446 (2010); Py, B., et al., "Fe—S clusters, fragile sentinels of the cell," *Curr. Opin. Microbiol.*, 14:218-223 (2011)) which involved the iron-sulfur cluster an observation consistent with a recent report in *S. cerevisiae* (Carlsen, S., et al., "Heterologous expression and characterization of bacterial 2-C-methyl-D-erythritol-4-phosphate pathway in *Saccharomyces cerevisiae*," *Appl. Microbiol. Biotechnol.* (2013)). The co-expression of Isc operon did enhance the production of amorphadiene production but the yield was significantly lower than in strain overexpressing the S-IAA modules. Modest enhancement was observed when the GH module was co-expressed with ISC module. Fine tuning of those genes (ispG, ispH, iscS, isCU, iscA, hscB, hscA, fdx) including controlling the expression levels and additional combinations can be used to increase the flux of intracellular MEC.

Given the need to construct multiple vectors, the CLIVA method described herein provides a rapid, effective and efficient approach to identify combinations of genes useful for the production of metabolites. In this study, we found that the overexpression of related pathway genes may not simply enhance but may unpredictably inhibit downstream metabolite production. Given the complexity of cellular regulatory pathways and experimental conditions, a systematic approach to identify optimal combinations of genes for high yield production will necessitate the construction of arrays of recombinant plasmids using the CLIVA method described herein.

Materials and Methods

Reagents, Growth Medium and Bacteria Strain

Restriction enzymes were purchased from NEB. The high fidelity DNA polymerase (IPROOF™) from Bio-Rad was used to amplify the DNA fragments for assembly and the ITAQ™ DNA polymerase from iDNA was used for quantitative colony PCR. Unless stated otherwise, all chemicals were purchased from either Sigma or Merck. Peptone and yeast extract were purchased from BD. Oligonucleotides were purchased from AITbiotech. Unmodified oligonucleotides were purified by desalting and the phosphorothioate modified oligonucleotides were purified with cartridge. All the cells for plasmid construction were grown in 2xPY media or 2xPY agar plates containing: peptone (20 g/L), yeast extract (10 g/L) and NaCl (10 g/L) with or without agar (7.5 g/L). The *E. coli* XL10-Gold strain (Invitrogen) was used for plasmid construction. The electroporation competent cells were prepared: 1 L of XL10-Gold cells at OD600~=0.4, washed for three time with equal volume of 10% cold glycerol, suspended in 10 ml of cold 10% glycerol and stored at −80° C. For amorphadiene production, the *E. coli* Bl21-Gold DE3 strain (Stratagene) harboring different kinds of DXP pathway plasmid together with the pRepressor plasmid carrying the lac repressor gene was cultured in production medium: peptone 20 g/L, yeast extract 10 g/L, NaCl 10 g/L, glycerol 20 g/L, HEPES 50 mM and Tween 80 5 g/L. The pRepressor plasmid was constructed by removing the T7 promoter, RBS and T7 terminator of pET-11a (Stratagene) plasmid and replacing the antibiotic resistant (ampicillin) with kanamycin. All the culture contained 34 mg/L chloramphenicol and 100 mg/L kanamycin to maintain the DXP pathway plasmid and pRepressor plasmid respectively. The cell density was defined by absorbance at 600 nm (OD600) and measured by SpectraMax 190 microplate reader. For amorphadiene production, 1% (v/v) cell culture of overnight grown cell culture was inoculated into 0.8 ml production medium together with another 0.2 ml organic dodecane phase to extract amorphadiene in 14 mL BD FALCON™ tube. The dodecane phase contained 1 g/L trans-caryophyllene as internal standard for amorphadiene. Cells were grown at 37° C. with 300 rpm shaking for 2 h when OD600 reached the range of 0.5-0.8 and induced by different concentrations of isopropyl B-D-1-thiogalactopyranoside (IPTG). After induction, the cell was incubated at 28° C. with 300 rpm shaking for the rest of the experiment. The induction time was considered as the zero time point in the study.

Quantitative Colony PCR

The quantitative colony PCR was carried out to test the presence of successful ligations at all the junctions of constructed plasmids using the primers listed in Table 8. For example, to confirm the S-GH-IAA-PAC plasmid, the junctions of PAC-S, S-GH and GH-IAA were verified by quantitative colony PCR respectively. For each junction, the sense primer in the upstream module and antisense primer in the downstream module were used as a pair to perform the real-time quantitative PCR, which were dxs-1609F/ispG-329R, ispH-693F/ADS-941R and PAC-seqF/dxs-122R pairs respectively. For quantitative colony PCR, the overnight cultured colonies were suspended in 100 μl of water. The real-time quantitative PCR reactions were carried out in 25 μl final volume containing 5 μl of cell suspension, 1x Xtensa Buffer (Bioworks), 200 nM of each primer, 2.5 mM MgCl2 and 0.75 U of iTaq DNA polymerase (iDNA). The reactions were analyzed using a BioRad ICYCLER 4™ Real-Time PCR Detection System (Bio-Rad) with SYBR Green I detection and the following protocol: an initial denaturation of 10 min at 95° C. to lyse the cells, followed by 40 cycles of 30 s at 95° C., 30 s at 60° C., and 1 min at 72° C. A melt curve was then carried out to check the melting temperature of the amplicon. Various primer pairs were selected from Table 8 to measure different module linkages in all the selected colonies. The results with a Ct number earlier than 18 and correct melting temperature were recognized as positive.

Plasmid Assembling by CLIVA Method

The primers for CLIVA optimization studies are listed in Table 5 and for DXP pathway assembling are listed in Table 6. The design details for all the 16 constructed plasmids are listed in Table 7. The modules containing various DXP pathway genes (dxs, dxr, ispD, ispE, ispF, ispG, ispG, idi, ispA or iron-sulfur (Fe—S) biosynthesis pathway (Isc operon, Suf operon), FIG. 22B) were amplified from the source plasmids constructed by placing those genes between T7 promoter and T7 terminator in pET-11a plasmid from Stratagene. The genomic DNA purified from MG1655 DE3 (ATCC) strain was used as original source for E. coli genes. The ADS from Artemisia annua was codon optimized for bacteria expression (FIG. 28, SEQ ID NO: 29). All the genes inside each module have their own ribosome binging sites (RBS). The PAC vector was amplified from pAC-Lyc plasmid from previous study (Cunningham, F. X., Jr., et al., "Molecular structure and enzymatic function of lycopene cyclase from the cyanobacterium Synechococcus sp strain PCC7942," Plant Cell, 6:1107-1121 (1994)). The amplified DNA fragments were purified and treated with 20 U DpnI at 37° C. for one hour. After that, 100 mM Tris-HCL at pH 9, 0.3% (v/v) iodine and 10% (v/v) ethanol were supplied to the reactions and the mixtures were heated at 70° C. for 5 min. If the mixture turned out to be colorless, additional 0.3% (v/v) iodine and 10% (v/v) ethanol would be supplied and the mixture would be heated at 70° C. for another 5 min. The DNA fragments treated with iodine and ethanol were then purified by ethanol precipitation. For CLIVA optimization experiments, 0.15 pmol of every pieces together with different kinds and concentrations of salts were heated at 80° C. for 1 min, cooled down to the temperature which was 3 degree lower than the melting temperature of the overlapped sequences, kept for 10 min and then cooled down to 20° C. at 0.1° C./s. 0.5 μl of the assembling mixture was mixed with 50 μl of XL10-Gold competent cell for electroporation. For DXP pathway assembling experiments, all the DNA fragments were prepared at 0.25 μM and equal amount of every pieces were mixed with MgCl2 at 2.5 mM. The mixture were heated at 80° C. for 1 min, cooled down to 68° C., kept for 10 min and then cooled down to 20° C. at 0.1° C./s. 0.5 μl of the assembling mixture was mixed with 50 μl of XL10-Gold competent cell for electroporation.

Metabolite Measurement

Amorphadiene was trapped in the dodecane phase and quantified as previously described (Tsuruta, H., et al., "High-level production of amorpha-4,11-diene, a precursor of the antimalarial agent artemisinin, in Escherichia coli," PLOS One, 4: e4489 (2009)). The dodecane phase was diluted 100 times in ethyl acetate and the amorphadiene was quantified by Agilent 7890 gas chromatography/mass spectrometry (GC/MS) by scanning 189 and 204 m/z ions, using trans-caryophyllene as standard. The amorphadiene concentrations were adjusted to the volume of cell suspension (0.8 ml) for report.

The DXP pathway intermediates (DXP, MEP, CPD-ME, CDP-MEP, MEC, HMBPP, IPP, DMAPP, GPP, FPP, FIG. 22A) were quantified by UPLC-MS as described (Zhou, K., et al., "Metabolite profiling identified methylerythritol cyclodiphosphate efflux as a limiting step in microbial isoprenoid production," PLOS One, 7: e47513 (2012)). For extracellular metabolites, the growth medium was diluted 30 times in methanol, shaken at room temperature for 2 min and centrifuged at 20,000 g for 5 min to yield the supernatant as the sample for injection. For intracellular metabolites, 1 ml×OD600 cell was collected and the medium was removed with centrifugation. The cell pellet was then suspended in 30 μl of water, 120 μl of methanol was added afterwards and the mixture was shaken at room temperature for 10 min to lyse the cells and release the intermediates (Rabinowitz, J. D., and Kimball, E., "Acidic acetonitrile for cellular metabolome extraction from Escherichia coli," Anal. Chem., 79:6167-6173 (2007)). The cell debris was removed by centrifugation at 20,000 g for 5 min. 5 μl of either extra-cellular or intracellular sample was injected. Aqueous solution containing 15 mM acetic acid and 10 mM tributylamine and methanol were used as mobile phase with a UPLC C18 column (Waters CSH C18 1.7 μm 2.1×50 mm). The elution was done at 0.15 mL/min with gradient. A standard curve following the same treatment was used to quantify the extracellular or intracellular metabolites. The detection limit was at least 5 μM in the final sample for FPP, CDP-MEP and at least 1 μM in the final sample for the rest of the metabolites.

TABLE 4

| | | | Transfor- | |
| | | | mation | |
| | | Number | efficiency | |
| | | of | (×10³ | |
| | | pieces | cfu/μg | |
| | Size | to | input | Accuracy |
| Plasmids | (kb) | assemble | DNA) | (%)* |
|---|---|---|---|---|
| IAA-PAC | 6.2 | 2 | 3612.8 | 100.0 |
| S-IAA-PAC | 8.7 | 2 | 1052.8 | 100.0 |
| S-R-IAA-PAC | 10.5 | 3 | 78.8 | 93.5 |
| S-DEF-IAA-PAC | 11.3 | 3 | 61.3 | 96.8 |
| S-GH-IAA-PAC | 11.3 | 3 | 46.6 | 83.9 |
| S-R-DEF-IAA-PAC | 13.1 | 4 | 13.2 | 42.6 |
| S-R-GH-IAA-PAC | 13.1 | 4 | 15.6 | 38.3 |
| S-DEF-GH-IAA-PAC | 13.9 | 4 | 9.0 | 27.7 |
| S-R-DEF-GH-IAA-PAC | 15.6 | 5 | 5.1 | 12.7 |
| S-ISC-IAA-PAC | 14.2 | 3 | 15.4 | 25.5 |
| S-SUR-IAA-PAC | 14.7 | 3 | 17.4 | 21.3 |
| S-GH-ISC-IAA-PAC | 16.8 | 4 | 4.9 | 14.1 |
| S-GH-SUR-IAA-PAC | 17.2 | 4 | 4.5 | 11.3 |
| S-R-GH-ISC-IAA-PAC | 18.5 | 5 | 3.1 | 9.9 |
| S-R-GH-SUR-IAA-PAC | 19.0 | 5 | 2.6 | 7.0 |
| S-R-DEF-GH-ISC-IAA-PAC | 21.6 | 6 | 2.0 | 8.5 |

*More than 30 colonies for each construct were analyzed by quantitative colony PCR for the accuracy calculation.

TABLE 5

Primers used for CLIVA optimization

| Design | Primer Name | Cross lapping primer | Sequence |
|---|---|---|---|
| | PAC-F | | GGACAGAGAGTGGAACCAACCG |
| | PAC-R | | GCCAAGTAGCGAAGCGAGCAG |
| | siDF-F | | TGCGACTCCTGCATTAGGAAGC |
| | siDF-R | | TCCCCGAAAAGTGCCACCTG |
| O12-13/1 | O13/1-PAC-F | O12/1-siDF-R | T*C*T*G*T*C*C*T*C*C*C*GAAAAGTGCCACCTG |
| | O12/1-PAC-R | O12/1-siDF-F | A*G*T*C*G*C*A*G*C*C*A*A*G*TAGCGAAGCGAGCAG |
| | O13/1-siDF-F | O13/1-PAC-R | C*T*T*G*G*C*T*G*C*G*A*C*T*CCTGCATTAGGAAGC |
| | O12/1-siDF-R | O13/1-PAC-F | G*G*G*G*A*G*G*A*C*A*G*A*GAGTGGAACCAACCG |
| O12-13/4-5 | O13/4-5-PAC-F | O12/4-5-siDF-R | TCTGT*CCTC*CCC*GAAAAGTGCCACCTG |
| | O12/4-5-PAC-R | O13/4-5-siDF-F | AGTCG*CAGC*CAAG*TAGCGAAGCGAGCAG |
| | O13/4-5-siDF-F | O12/4-5-PAC-R | CTTGG*CTGC*GACT*CCTGCATTAGGAAGC |
| | O12/4-5-siDF-R | O13/4-5-PAC-F | GGGG*AGGA*CAGA*GAGTGGAACCAACCG |
| O12-13/6-7 | O13/6-7-PAC-F | O12/6-7-siDF-R | TCTGTCC*TCCCC*GAAAAGTGCCACCTG |
| | O12/6-7-PAC-R | O13/6-7-siDF-F | AGTCGCA*GCCAAG*TAGCGAAGCGAGCAG |
| | O13/6-7-siDF-F | O12/6-7-PAC-R | CTTGGCT*GCGACT*CCTGCATTAGGAAGC |
| | O12/6-7-siDF-R | O13/6-7-PAC-F | GGGGAG*GACAGA*GAGTGGAACCAACCG |
| O12-13/12-13 | O13/13-PAC-F | O12/12-siDF-R | TCTGTCCTCCCC*GAAAAGTGCCACCTG |
| | O12/12-PAC-R | O13/13-siDF-F | AGTCGCAGCCAAG*TAGCGAAGCGAGCAG |
| | O13/13-siDF-F | O12/12-PAC-R | CTTGGCTGCGACT*CCTGCATTAGGAAGC |
| | O12/12-siDF-R | O13/13-PAC-F | GGGGAGGACAGA*GAGTGGAACCAACCG |
| O24-25/4-5 | O24/4-5-PAC-F | O24/4-5-siDF-R | CCAC*TCTC*TGTC*CTCC*CCGA*AAAG*TGCCACCTG |
| | O25/4-5-PAC-R | O25/4-5-siDF-F | TGCAG*GAGT*CGCA*GCCA*AGTA*GCGA*AGCGAGCAG |
| | O25/4-5-siDF-F | O25/4-5-PAC-R | TCGC*TACTT*GGCT*GCGA*CTCC*TGCA*TTAGGAAGC |
| | O24/4-5-siDF-R | O24/4-5-PAC-F | CTTT*TCGG*GGAG*GACA*GAGA*GTGG*AACCAACCG |
| O24-25/24-25 | O24/24-PAC-F | O24/24-siDF-R | CCACTCTCTGTCCTCCCCGAAAAG*TGCCACCTG |
| | O25/25-PAC-R | O25/25-siDF-F | TGCAGGAGTCGCAGCCAAGTAGCGA*AGCGAGCAG |
| | O25/25-siDF-F | O25/25-PAC-R | TCGCTACTTGGCTGCGACTCCTGCA*TTAGGAAGC |
| | O24/24-siDF-R | O24/24-PAC-F | CTTTTCGGGGAGGACAGAGAGTGG*AACCAACCG |

TABLE 5-continued

| | | Cross | |
| | Primer | lapping | |
| Design | Name | primer | Sequence |
|---|---|---|---|
| O36-<br>38/4-5 | O38/4-<br>5-PAC-<br>F | O38/4-<br>5-siDF-<br>R | GTGG*CACTTT*TCGG*GGAG*GACAG*AGAGT*GGAA*CCAA*CCG |
| | O36/4-<br>5-PAC-<br>R | O36/4-<br>5-siDF-<br>F | TCCTAA*TGCAG*GAGTC*GCAG*CCAA*GTAGC*GAAG*CGAG*CAG |
| | O36/4-<br>5-siDF-<br>F | O36/4-<br>5-PAC-<br>R | CTCG*CTTCG*CTACT*TGGCT*GCGA*CTCCT*GCATT*AGGA*AGC |
| | O38/4-<br>5-siDF-<br>R | O38/4-<br>5-PAC-<br>F | TTGGTT*CCAC*TCTCT*GTCC*TCCC*CGAAA*AGTG*CCAC*CTG |
| O38/36-38 | O38/38-<br>PAC-F | O38/38-<br>siDF-R | GTGGCACTTTTCGGGGAGGACAGAGAGTGGAACCAA*CCG |
| | O36/36-<br>PAC-R | O36/36-<br>siDF-F | TCCTAATGCAGGAGTCGCAGCCAAGTAGCGAAGCGAG*CAG |
| | O36/36-<br>siDF-F | O36/36-<br>PAC-R | CTCGCTTCGCTACTTGGCTGCGACTCCTGCATTAGGA*AGC |
| | O38/38-<br>siDF-R | O38/38-<br>PAC-F | TTGGTTCCACTCTCTGTCCTCCCCGAAAAGTGCCAC*CTG |

The phosphorothioate modifications were presented as *. The PAC-F, PAC-R, siDF-F and siDF-R were the gene specific sequences. An "Ox/y" designation was used to define the primers, where O denoted overlap; x was the length of overlap which had one modification at each y base pairs of the sequence. For example, O13/1 was a primer with 13 bases of overlap and phosphorothioate modifications at every base-pair. Similarly, O13/4 denoted a primer with 13 overlaps and phosphorothioate modifications at every $4^{th}$ base-pair. Sequences are SEQ ID NOs: 30 to 65.

TABLE 6

Primers used for DXP pathway construction

| Name | Cross<br>lapping<br>primer | Sequence |
|---|---|---|
| CL-pET-1F | CL-pAC-R | CTCG*CTTCG*CTACT*TGGCT*GCGA*CTCCT*GCATT*AGGA*AGC |
| CL-pET-2F | CL-pET-aR | CCGC*AAGAG*GCCC*GCAGT*AGTAG*GTTGA*GGCC*GTTGA |
| CL-pET-3F | CL-pET-bR | GTACC*GGCA*TAACC*AAGCC*ACCG*CCGC*CGC*AAGG*AAT |
| CL-pET-4F | CL-pET-cR | CTACA*GCATC*CAGG*GTGA*CCCT*GCCA*CCATA*CCCA*CGC |
| CL-pET-5F | CL-pET-dR | CGAG*GATGA*CGATG*AGCG*TGAGC*CCGA*AGTG*GCG*AGC |
| CL-pET-6F | CL-pET-eR | CT GAC*TGCG*TTAGC*AATTTA*ACAGC*AACC*GCAC*CTGT*GGC |
| CL-pET-7F | CL-pET-fR | AGAC*GAAAG*GGCC*TCGG*ATGC*GTCC*GGCG*TAGA*GGA |
| CL-pAC-F | CL-pET-gR | GTGG*CACTTT*TCGG*GGAG*GACAG*AGAGT*GGAA*CCAA*CCG |
| CL-pAC-R | CL-pET-1F | TCCTAA*TGCAG*GAGTC*GCAG*CCAA*GTAGC*GAAG*CGAG*CAG |
| CL-pET-aR | CL-pET-2F | GGCC*TCAAC*CTACT*ACTGC*GGGC*CTCTT*GCGG*GATA |
| CL-pET-bR | CL-pET-3F | CCTTG*CGGC*GGCG*GTGG*CTTG*GTTAT*GCCG*GTAC*TGC |
| CL-pET-cR | CL-pET-4F | TGGG*TATGG*TGGC*AGGG*TCACC*CTGGA*TGCT*GTAG*GCA |
| CL-pET-dR | CL-pET-5F | CGCC*ACTTC*GGGC*TCACG*CTCA*TCGT*CATC*CTCG*GCA |
| CL-pET-eR | CL-pET-6F | ACAGG*TGCG*GTTGC*TGTTA*AATTG*CTAAC*GCAG*TCAG*GCA |
| CL-pET-fR | CL-pET-7F | TCTACG*CCGG*ACGCA*TCCG*AGGC*CCTTT*CGTCT*TCA |
| CL-pET-gR | CL-pAC-F | TTGGTT *CCAC*TCTCT*GTCC*TCCC*CGAAA*AGTG*CCAC*CTG |

The phosphorothioate modifications were presented as *. And the underlined sequences were the gene specific sequences of the primers. Sequences are SEQ IDS NOs: 66 to 81.

Plasmids — Primers for used to amplify the modules

| Template | S<br>T7-dxs<br>pET-dxs | R<br>T7-dxr<br>pET-dxr | DEF<br>T7-ispE-ispD-ispF<br>pET-DEF | GH<br>T7-ispG-ispH<br>pET-GH | IAA<br>T7-ADS-ispA-idi<br>pET-IAA | ISC<br>T7-iscS-iscU-iscA-hscB-hscA-fdx<br>pET-SC | SUF<br>T7-sufA-sufB-sufC-sufD-sufS-sufE<br>pET-SUF | PAC<br>PAC<br>pAC-lyc | IAA-PAC<br>T7-ADS-ispA-idi-PAC<br>IAA-PAC |
|---|---|---|---|---|---|---|---|---|---|
| IAA-PAC | — | — | — | — | CL-pET-1F<br>CL-pET-gR | — | — | CL-PAC-F<br>CL-PAC-R | — |
| S-IAA-PAC | CL-pET-1F<br>CL-pET-fR | — | — | — | — | — | — | — | CL-pET-7F<br>CL-PAC-R |
| S-R-IAA-PAC | CL-pET-1F<br>CL-pET-aR | CL-pET-2F<br>CL-pET-fR | — | — | — | — | — | — | CL-pET-7F<br>CL-PAC-R |
| S-DEF-IAA-PAC | CL-pET-1F<br>CL-pET-bR | — | CL-pET-3F<br>CL-pET-fR | — | — | — | — | — | CL-pET-7F<br>CL-PAC-R |
| 5-GH-IAA-PAC | CL-pET-1F<br>CL-pET-cR | — | — | CL-pET-4F<br>CL-pET-fR | — | — | — | — | CL-pET-7F<br>CL-PAC-R |
| S-R-DEF-IAA-PAC | CL-pET-1F<br>CL-pET-aR | CL-pET-2F<br>CL-pET-bR | CL-pET-3F<br>CL-pET-fR | — | — | — | — | — | CL-pET-7F<br>CL-PAC-R |
| S-R-GH-IAA-PAC | CL-pET-1F<br>CL-pET-bR | — | CL-PET-3F<br>CL-pET-cR | CL-pET-4F<br>CL-pET-fR | — | — | — | — | CL-pET-7F<br>CL-PAC-R |
| S-DEF-GH-IAA-PAC | CL-pET-1F<br>CL-pET-aR | CL-pET-2F<br>CL-pET-cR | — | CL-pET-4F<br>CL-pET-fR | — | — | — | — | CL-pET-7F<br>CL-PAC-R |
| S-R-DEF-GH-IAA-PAC | CL-pET-1F<br>CL-pET-aR | CL-pET-2F<br>CL-pET-bR | CL-pET-3F<br>CL-pET-cR | CL-pET-4F<br>CL-pET-fR | — | — | — | — | CL-pET-7F<br>CL-PAC-R |
| S-ISC-IAA-PAC | CL-pET-1F<br>CL-pET-dR | — | — | — | — | CL-pET-5F<br>CL-pET-fR | — | — | CL-pET-7F<br>CL-PAC-R |
| S-SUR-IAA-PAC | CL-pET-1F<br>CL-pET-eR | — | — | — | — | — | CL-pET-6F<br>CL-pET-fR | — | CL-pET-7F<br>CL-PAC-R |
| S-GH-ISC-IAA-PAC | CL-pET-1F<br>CL-pET-cR | — | — | CL-pET-4F<br>CL-pET-dR | — | CL-pET-5F<br>CL-pET-fR | — | — | CL-pET-7F<br>CL-PAC-R |
| S-GH-SUR-IAA-PAC | CL-pET-1F<br>CL-pET-cR | — | — | CL-pET-4F<br>CL-pET-eR | — | — | CL-PET-6F<br>CL-pET-fR | — | CL-pET-7F<br>CL-PAC-R |
| S-R-GH-ISC-IAA-PAC | CL-pET-1F<br>CL-pET-bR | — | CL-pET-3F<br>CL-pET-cR | CL-pET-4F<br>CL-pET-dR | — | CL-pET-5F<br>CL-pET-fR | — | — | CL-pET-7F<br>CL-PAC-R |
| S-R-GH-SUR-IAA-PAC | CL-pET-1F<br>CL-pET-bR | — | CL-pET-3F<br>CL-pET-cR | CL-pET-4F<br>CL-pET-eR | — | — | CL-pET-6F<br>CL-pET-fR | — | CL-pET-7F<br>CL-PAC-R |
| S-R-DEF-GH-ISC-IAA-PAC | CL-pET-1F<br>CL-pET-aR | CL-pET-2F<br>CL-pET-bR | CL-PET-3F<br>CL-pET-cR | CL-pET-4F<br>CL-pET-dR | — | CL-pET-5F<br>CL-pET-fR | — | — | CL-pET-7F<br>CL-PAC-R |

TABLE 8

Primers used to check the constructions with quantitative colony PCR, SEQ ID NOs: 82 to 97

| Name | Position | Sequence |
|---|---|---|
| dxs-1609F | S, sense | CCGCTTGATGAAGCGTTAATTCTGG |
| dxs-122R | S, antisense | GGAACGGCTCACGCTGT |
| dxr-704F | R, sense | AAGGTCTGGAATACATTGAAGC |
| dxr-782R | R, antisense | CACTGCCGTCCTGATAGC |
| ispF-220F | DEF, sense | TTAAAGGTGCCGATAGCC |
| ispE-349R | DEF, antisense | ATTGCCAGAGATGATTTAATGC |
| ispH-693F | GH, sense | CTCCAACTCCAACCGTCTG |
| ispG-329R | GH, antisense | ACGCTCTTCATTACCGATATTGC |
| idi-462F | IAA, sense | TGTATTACACGGTATTGATGCCACG |
| ADS-941R | IAA, antisense | GCTTTGGTGAAGAATACGCGAGCA |

TABLE 8-continued

Primers used to check the constructions with quantitative colony PCR, SEQ ID NOs: 82 to 97

| Name | Position | Sequence |
|---|---|---|
| PAC-seqF | PAC, sense | CCTGCTCGCTTCGCTACT |
| PAC-seqR | PAC, antisense | GCGGTGCGGACTGTTG |
| FDX-89F | ISC, sense | CTCTGCGTAACGGTATCG |
| iscS-601R | ISC, antisense | ACATCAGGTCAACTTTCAACT |
| surfA-334R | SUF, sense | TCTGGGCTTTAGGGTTGT |
| surfE-273F | SUF, antisense | GATGACGCCGCAGGATAT |

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that it is incorporated by reference in its entirety for all purposes as well as for the proposition that is recited. Where any conflict exits between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures) as well as chemical references (e.g. Pub Chem compound, Pub Chem substance, or Pub Chem Bioassay entries, including the annotations therein, such as structures and assays et cetera) are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g. elements, including numerical ranges and exemplary embodiments) of particular embodiments and aspects of the invention including the working examples. For example, particular experimental parameters exemplified in the working examples can be adapted for use in the claimed invention piecemeal without departing from the invention. For example, for materials that are disclosed, while specific reference of each various individual and collective combinations and permutation of these compounds may not be explicitly disclosed, each is specifically contemplated and described herein. Thus, if a class of elements A, B, and C are disclosed as well as a class of elements D, E, and F and an example of a combination of elements, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art-thus to the extent an element is described in one or more references known to the person having ordinary skill in the art, they may be excluded from the claimed invention by, inter alia, a negative proviso or disclaimer of the feature or combination of features.

While this invention has been particularly shown and described with references to example embodiments thereof, it will be understood by those skilled in the art that various changes in form and details may be made therein without departing from the scope of the invention encompassed by the appended claims.

What is claimed is:

1. A host cell comprising an univariant expression vector, wherein the univariant expression vector comprises:

a) a first coding region encoding at least a first gene product, the first coding region being operably linked to a first inducible promoter comprising a first melting/initiation region and a polymerase binding region, the first inducible promoter being of a first strength and being responsive to an inducer; and b) a second coding region encoding at least a second gene product, the second coding region being operably linked to a second inducible promoter comprising a second melting/initiation region and the polymerase binding region, the second inducible promoter being of a second strength, different from the first strength, and being responsive to the inducer, wherein the first melting/initiation region differs from the second melting/initiation region.

2. The host cell of claim 1, wherein the first and the second inducible promoters originate from a single RNA polymerase promoter.

3. The host cell of claim 2, wherein the first inducible promoter comprises a mutation in the first melting/initiation region.

4. The host cell of claim 3, wherein the RNA polymerase promoter is a T7 RNA polymerase promoter, a T5 RNA polymerase promoter, a T3 RNA polymerase promoter, or an SP6 RNA polymerase promoter.

5. The host cell of claim 1, wherein:

the first coding region encodes at least a first enzyme, the first enzyme catalyzing a first reaction in a multi-step enzymatic pathway; and the second coding region encodes at least a second enzyme, the second enzyme catalyzing a second reaction in the multi-step enzymatic pathway.

6. The host cell of claim 5, wherein the first reaction and the second reaction are rate-limiting steps of the multi-step enzymatic pathway in the host cell.

7. The host cell of claim 6, wherein the univariant expression vector further comprises a third coding region encoding at least a third gene product, the third coding region being operably linked to a third inducible promoter comprising a third melting/initiation region and the polymerase binding region, the third inducible promoter being of a third strength, different from the first strength and the second strength, and being responsive to the inducer.

8. The host cell of claim 7, wherein the third coding region encodes at least a third enzyme catalyzing a rate-limiting step of the multi-step enzymatic pathway in a host cell.

9. The host cell of claim 5, wherein the multi-step enzymatic pathway is a lycopene synthetic pathway or an amorphadiene synthetic pathway.

10. The host cell of claim 1, wherein the host cell is an E. coli.

11. A host cell, comprising a first expression vector and a second expression vector, wherein:

a) the first expression vector comprises a first coding region encoding at least a first gene product, the first coding region being operably linked to a first inducible promoter comprising a first melting/initiation region and a polymerase binding region, the first inducible promoter being of a first strength and being responsive to an inducer;

b) the second expression vector comprises a second coding region encoding at least a second gene product, the second coding region being operably linked to a second inducible promoter comprising a second melting/initiation region and the polymerase binding region, the second inducible promoter being of a second strength, different from the first strength, and being responsive to the inducer, wherein the first melting/initiation region differs from the second melting/initiation region.

12. The host cell of claim 11, wherein the first and the second inducible promoters originate from a single RNA polymerase promoter.

13. The host cell of claim 12, wherein the first inducible promoter comprises a mutation in the first melting/initiation region.

14. The host cell of claim 13, wherein the RNA polymerase promoter is a T7 RNA polymerase promoter, a T5 RNA polymerase promoter, a T3 RNA polymerase promoter, or an SP6 RNA polymerase promoter.

15. The host cell of claim 11, wherein:

the first coding region encodes at least a first enzyme, the first enzyme catalyzing a first reaction in a multi-step enzymatic pathway; and the second coding region encodes at least a second enzyme, the second enzyme catalyzing a second reaction in the multi-step enzymatic pathway.

16. The host cell of claim 15, wherein the first reaction and the second reaction are rate-limiting steps of the multi-step enzymatic pathway in the host cell.

17. The host cell of claim 16, wherein the univariant expression vector further comprises a third coding region encoding at least a third gene product, the third coding region being operably linked to a third inducible promoter comprising a third melting/initiation region and the polymerase binding region, the third inducible promoter being of a third strength, different from the first strength and the second strength, and being responsive to the inducer.

18. The host cell of claim 17, wherein the third coding region encodes at least a third enzyme catalyzing a rate-limiting step of the multi-step enzymatic pathway in a host cell.

19. The host cell of claim 15, wherein the multi-step enzymatic pathway is a lycopene synthetic pathway or an amorphadiene synthetic pathway.

20. The host cell of claim 11, wherein the host cell is an *E. coli*.

* * * * *

SEQUENCE LISTING

```
<160> NUMBER OF SEQ ID NOS: 97

<210> SEQ ID NO 1
<211> LENGTH: 36
<212> TYPE: DNA
<213> ORGANISM: Artificial Sequence
<220> FEATURE:
<223> OTHER INFORMATION: promoter, T7 promoter

<400> SEQUENCE: 1
cgaaattaat acgactcact ataggggaat tgtgag                              36

<210> SEQ ID NO 2
<211> LENGTH: 36
<212> TYPE: DNA
<213> ORGANISM: Artificial Sequence
<220> FEATURE:
<223> OTHER INFORMATION: promoter

<400> SEQUENCE: 2
cgaaattaat acgactcact taaggggaat tgtgag                              36

<210> SEQ ID NO 3
<211> LENGTH: 36
<212> TYPE: DNA
<213> ORGANISM: Artificial Sequence
<220> FEATURE:
<223> OTHER INFORMATION: promoter, TM1 promoter
```

-continued

```
<400> SEQUENCE: 3
cgaaattaat acgactcact aatggggaat tgtgag                          36

<210> SEQ ID NO 4
<211> LENGTH: 36
<212> TYPE: DNA
<213> ORGANISM: Artificial Sequence
<220> FEATURE:
<223> OTHER INFORMATION: promoter

<400> SEQUENCE: 4
cgaaattaat acgactcact attgtggaat tgtgag                          36

<210> SEQ ID NO 5
<211> LENGTH: 36
<212> TYPE: DNA
<213> ORGANISM: Artificial Sequence
<220> FEATURE:
<223> OTHER INFORMATION: promoter

<400> SEQUENCE: 5
cgaaattaat acgactcact agtggggaat tgtgag                          36

<210> SEQ ID NO 6
<211> LENGTH: 36
<212> TYPE: DNA
<213> ORGANISM: Artificial Sequence
<220> FEATURE:
<223> OTHER INFORMATION: promoter

<400> SEQUENCE: 6
cgaaattaat acgactcacg aaaggggaat tgtgag                          36

<210> SEQ ID NO 7
<211> LENGTH: 36
<212> TYPE: DNA
<213> ORGANISM: Artificial Sequence
<220> FEATURE:
<223> OTHER INFORMATION: promoter, TM2 promoter

<400> SEQUENCE: 7
cgaaattaat acgactcact cgaggggaat tgtgag                          36

<210> SEQ ID NO 8
<211> LENGTH: 36
<212> TYPE: DNA
<213> ORGANISM: Artificial Sequence
<220> FEATURE:
<223> OTHER INFORMATION: promoter

<400> SEQUENCE: 8
cgaaattaat acgactcact gcaggggaat tgtgag                          36

<210> SEQ ID NO 9
<211> LENGTH: 36
<212> TYPE: DNA
<213> ORGANISM: Artificial Sequence
<220> FEATURE:
<223> OTHER INFORMATION: promoter, TM3 promoter

<400> SEQUENCE: 9
cgaaattaat acgactcact ataaaggaat tgtgag                          36

<210> SEQ ID NO 10
<211> LENGTH: 36
```

```
<212> TYPE: DNA
<213> ORGANISM: Artificial Sequence
<220> FEATURE:
<223> OTHER INFORMATION: promoter

<400> SEQUENCE: 10
cgaaattaat acgactcact ataccggaat tgtgag                                36

<210> SEQ ID NO 11
<211> LENGTH: 36
<212> TYPE: DNA
<213> ORGANISM: Artificial Sequence
<220> FEATURE:
<223> OTHER INFORMATION: promoter

<400> SEQUENCE: 11
cgaaattaat acgactcact atacaggaat tgtgag                                36

<210> SEQ ID NO 12
<211> LENGTH: 36
<212> TYPE: DNA
<213> ORGANISM: Artificial Sequence
<220> FEATURE:
<223> OTHER INFORMATION: promoter

<400> SEQUENCE: 12
cgaaattaat acgactcact atgtgggaat tgtgag                                36

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide, dxs forward primer

<400> SEQUENCE: 13
cggctatcac tataacgatg g                                                21

<210> SEQ ID NO 14
<211> LENGTH: 18
<212> TYPE: DNA
<213> ORGANISM: Artificial Sequence
<220> FEATURE:
<223> OTHER INFORMATION: synthetic oligonucleotide, dxs reverse primer

<400> SEQUENCE: 14
cacgacgctt cacaatgc                                                    18

<210> SEQ ID NO 15
<211> LENGTH: 17
<212> TYPE: DNA
<213> ORGANISM: Artificial Sequence
<220> FEATURE:
<223> OTHER INFORMATION: synthetic oligonucleotide, crtE forward primer

<400> SEQUENCE: 15
gtaaagcggg cgtttcg                                                     17

<210> SEQ ID NO 16
<211> LENGTH: 15
<212> TYPE: DNA
<213> ORGANISM: Artificial Sequence
<220> FEATURE:
<223> OTHER INFORMATION: synthetic oligonucleotide, crtE reverse primer

<400> SEQUENCE: 16
```

```
gccagcagca tcagc                                                    15

<210> SEQ ID NO 17
<211> LENGTH: 25
<212> TYPE: DNA
<213> ORGANISM: Artificial Sequence
<220> FEATURE:
<223> OTHER INFORMATION: synthetic oligonucleotide, idi forward primer

<400> SEQUENCE: 17
tgtattacac ggtattgatg ccacg                                         25

<210> SEQ ID NO 18
<211> LENGTH: 25
<212> TYPE: DNA
<213> ORGANISM: Artificial Sequence
<220> FEATURE:
<223> OTHER INFORMATION: synthetic oligonucleotide, idi reverse primer

<400> SEQUENCE: 18
agctgggtaa atgcagataa tcgtt                                         25

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide, cysG forward primer

<400> SEQUENCE: 19
ttgtcggcgg tggtgatgtc                                               20

<210> SEQ ID NO 20
<211> LENGTH: 24
<212> TYPE: DNA
<213> ORGANISM: Artificial Sequence
<220> FEATURE:
<223> OTHER INFORMATION: synthetic oligonucleotide, cysG reverse primer

<400> SEQUENCE: 20
atgcggtgaa ctgtggaata aacg                                          24

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide, eGFP forward primer

<400> SEQUENCE: 21
gaccactacc agcagaacac c                                             21

<210> SEQ ID NO 22
<211> LENGTH: 18
<212> TYPE: DNA
<213> ORGANISM: Artificial Sequence
<220> FEATURE:
<223> OTHER INFORMATION: synthetic oligonucleotide, eGFP reverse primer

<400> SEQUENCE: 22
gaccatgtga tcgcgctt                                                 18

<210> SEQ ID NO 23
<211> LENGTH: 18
<212> TYPE: DNA
<213> ORGANISM: Artificial Sequence
```

-continued

```
<220> FEATURE:
<223> OTHER INFORMATION: synthetic oligonucleotide, tag1 forward primer

<400> SEQUENCE: 23
cacgcatcgc aaggctga                                                    18

<210> SEQ ID NO 24
<211> LENGTH: 19
<212> TYPE: DNA
<213> ORGANISM: Artificial Sequence
<220> FEATURE:
<223> OTHER INFORMATION: synthetic oligonucleotide, tag1 reverse primer

<400> SEQUENCE: 24
tggctggcct gttacctga                                                   19

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide, tag2 forward primer

<400> SEQUENCE: 25
ggtcagccca ctacccacaa                                                  20

<210> SEQ ID NO 26
<211> LENGTH: 18
<212> TYPE: DNA
<213> ORGANISM: Artificial Sequence
<220> FEATURE:
<223> OTHER INFORMATION: synthetic oligonucleotide, tag2 reverse primer

<400> SEQUENCE: 26
cccaacggag gcaaggat                                                    18

<210> SEQ ID NO 27
<211> LENGTH: 23
<212> TYPE: DNA
<213> ORGANISM: Artificial Sequence
<220> FEATURE:
<223> OTHER INFORMATION: synthetic oligonucleotide, tag3 forward primer

<400> SEQUENCE: 27
cgtccttatt gcgatcttta ccg                                              23

<210> SEQ ID NO 28
<211> LENGTH: 19
<212> TYPE: DNA
<213> ORGANISM: Artificial Sequence
<220> FEATURE:
<223> OTHER INFORMATION: synthetic oligonucleotide, tag3 reverse primer

<400> SEQUENCE: 28
caggcgtttc aactgctgg                                                   19

<210> SEQ ID NO 29
<211> LENGTH: 1638
<212> TYPE: DNA
<213> ORGANISM: Artificial Sequence
<220> FEATURE:
<223> OTHER INFORMATION: codon optimized ADS gene

<400> SEQUENCE: 29
atgtctctga ctgaggaaaa accaatccgt ccgatcgcaa actttccgcc gagcatctgg       60
```

-continued

```
ggtgatcagt tcctgatcta ccagaagcag gtcgagcaag gcgtagaaca gatcgtgaac    120
gacctgaaaa aggaggtacg tcagctgctg aaagaggctc tggacatccc gatgaaacat    180
gcgaacctgc tgaagctgat tgatgagatt cagcgcctgg gtatcccata ccacttcgaa    240
cgtgaaattg atcacgcgct gcagtgtatt tatgaaacgt atggtgataa ctggaacggt    300
gaccgtagct ccctgtggtt ccgtctgatg cgtaagcagg gttattacgt gacctgcgac    360
gtcttcaaca actacaaaga caagaacggc gcgtttaaac agagcctggc gaatgacgtt    420
gaaggcctgc tggagctgta tgaagcaacc tctatgcgtg ttccgggcga aatcatcctg    480
gaagatgctc tgggtttcac ccgttctcgc ctgtctatca tgaccaagga cgcattttcc    540
actaacccgg ccctgttcac cgaaatccag cgtgcgctga acagcctct gtggaagcgt    600 ctgccgcgta tcgaggcggc acagtacatc ccgttctatc agcaacagga ttcccacaac    660
aaaaccctgc tgaaactggc gaaactggaa tttaacctgc tgcaatccct gcacaaagaa    720
gaactgtctc atgtttgcaa atggtggaaa gccttcgaca tcaagaaaaa cgcgccgtgc    780
ctgcgcgacc gtatcgtaga atgctatttc tggggcctgg gctccggtta tgagcctcaa    840
tactctcgtg ctcgcgtatt cttcaccaaa gcggtagctg tgatcaccct gatcgacgat    900
acctacgatg cttacggtac gtacgaagaa ctgaagattt ttaccgaggc tgttgaacgc    960
tggtctatca cttgcctgga taccctgccg gaatacatga aaccgatcta taaactgttc    1020
atggatactt ataccgaaat ggaagagttc ctggcaaaag aaggtcgcac tgatctgttc    1080
aactgtggca aggagtttgt gaaagaattc gtccgcaacc tgatggtgga ggcgaagtgg    1140
gcaaacgagg gtcacatccc gaccaccgaa gaacacgacc cggtagttat catcaccggt    1200
ggcgcaaacc tgctgactac cacttgctac ctgggtatgt ccgacatttt tacgaaagaa    1260
agcgttgaat gggcagtgtc tgcgcctccg ctgttccgtt actctggtat cctgggccgt    1320
cgcctgaacg atctgatgac ccataaagcc gagcaggaac gtaaacactc cagcagctct    1380
ctggaatctt acatgaaaga atacaacgtt aacgaagagt atgcgcagac cctgatctac    1440
aaagaggttg aggatgtatg gaaagacatc aaccgtgagt acctgactac taaaaacatc    1500
ccacgcccgc tgctgatggc agtgatttat ctgtgccagt ttctggaagt gcagtatgcg    1560
ggcaaagata acttcacccg tatgggtgac gaatacaaac acctgatcaa gtccctgctg    1620
gtttacccaa tgtccatc    1638
```

```
<210> SEQ ID NO 30
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 30
ggacagagag tggaaccaac cg    22
```

```
<210> SEQ ID NO 31
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 31
gccaagtagc gaagcgagca g    21
```

<210> SEQ ID NO 32
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 32
tgcgactcct gcattaggaa gc                                                      22

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
tccccgaaaa gtgccacctg                                                         20

<210> SEQ ID NO 34
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)...(12)
<223> OTHER INFORMATION: phosphorothioate modification

<400> SEQUENCE: 34
tctgtcctcc cgaaaagtg ccacctg                                                  27

<210> SEQ ID NO 35
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)...(13)
<223> OTHER INFORMATION: phosphorothioate modification

<400> SEQUENCE: 35
agtcgcagcc aagtagcgaa gcgagcag                                                28

<210> SEQ ID NO 36
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)...(13)
<223> OTHER INFORMATION: phosphorothioate modification

<400> SEQUENCE: 36
cttggctgcg actcctgcat taggaagc                                                28

<210> SEQ ID NO 37
<211> LENGTH: 27
<212> TYPE: DNA
<213> ORGANISM: Artificial Sequence
<220> FEATURE:
<223> OTHER INFORMATION: synthetic oligonucleotide
<220> FEATURE:

-continued

```
<221> NAME/KEY: modified_base
<222> LOCATION: (1)...(12)
<223> OTHER INFORMATION: phosphorothioate modification

<400> SEQUENCE: 37
ggggaggaca gagagtggaa ccaaccg                                               27

<210> SEQ ID NO 38
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 12
<223> OTHER INFORMATION: phosphorothioate modification

<400> SEQUENCE: 38
tctgtcctcc ccgaaaagtg ccacctg                                              27

<210> SEQ ID NO 39
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 13
<223> OTHER INFORMATION: phosphorothioate modification

<400> SEQUENCE: 39
agtcgcagcc aagtagcgaa gcgagcag                                             28

<210> SEQ ID NO 40
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 13
<223> OTHER INFORMATION: phosphorothioate modification

<400> SEQUENCE: 40
cttggctgcg actcctgcat taggaagc                                             28

<210> SEQ ID NO 41
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 8, 12
<223> OTHER INFORMATION: phosphorothioate modification

<400> SEQUENCE: 41
ggggaggaca gagagtggaa ccaaccg                                              27

<210> SEQ ID NO 42
<211> LENGTH: 27
<212> TYPE: DNA
<213> ORGANISM: Artificial Sequence
<220> FEATURE:
<223> OTHER INFORMATION: synthetic oligonucleotide
```

```
<220> FEATURE:
<221> NAME/KEY: modified_base
<222> LOCATION: 7, 12
<223> OTHER INFORMATION: phosphorothioate modification

<400> SEQUENCE: 42
tctgtcctcc ccgaaaagtg ccacctg                                           27

<210> SEQ ID NO 43
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 7, 13
<223> OTHER INFORMATION: phosphorothioate modification

<400> SEQUENCE: 43
agtcgcagcc aagtagcgaa gcgagcag                                          28

<210> SEQ ID NO 44
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 7, 13
<223> OTHER INFORMATION: phosphorothioate modification

<400> SEQUENCE: 44
cttggctgcg actcctgcat taggaagc                                          28

<210> SEQ ID NO 45
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 6, 12
<223> OTHER INFORMATION: phosphorothioate modification

<400> SEQUENCE: 45
ggggaggaca gagagtggaa ccaaccg                                           27

<210> SEQ ID NO 46
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 12
<223> OTHER INFORMATION: phosphorothioate modification

<400> SEQUENCE: 46
tctgtcctcc ccgaaaagtg ccacctg                                           27

<210> SEQ ID NO 47
<211> LENGTH: 28
<212> TYPE: DNA
<213> ORGANISM: Artificial Sequence
<220> FEATURE:
```

<223> OTHER INFORMATION: synthetic oligonucleotide
<220> FEATURE:
<221> NAME/KEY: modified_base
<222> LOCATION: 13
<223> OTHER INFORMATION: phosphorothioate modification

<400> SEQUENCE: 47
agtcgcagcc aagtagcgaa gcgagcag                                                        28

<210> SEQ ID NO 48
<211> LENGTH: 28
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 13
<223> OTHER INFORMATION: phosphorothioate modification

<400> SEQUENCE: 48
cttggctgcg actcctgcat taggaagc                                                        28

<210> SEQ ID NO 49
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 12
<223> OTHER INFORMATION: phosphorothioate modification

<400> SEQUENCE: 49
ggggaggaca gagagtggaa ccaaccg                                                         27

<210> SEQ ID NO 50
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 8, 12, 16, 20, 24
<223> OTHER INFORMATION: phosphorothioate modification

<400> SEQUENCE: 50
ccactctctg tcctccccga aaagtgccac ctg                                                  33

<210> SEQ ID NO 51
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 13, 17, 21, 25
<223> OTHER INFORMATION: phosphorothioate modification

<400> SEQUENCE: 51
tgcaggagtc gcagccaagt agcgaagcga gcag                                                 34

<210> SEQ ID NO 52
<211> LENGTH: 34
<212> TYPE: DNA
<213> ORGANISM: Artificial Sequence

```
<220> FEATURE:
<223> OTHER INFORMATION: synthetic oligonucleotide
<220> FEATURE:
<221> NAME/KEY: modified_base
<222> LOCATION: 4, 9, 13, 17, 21, 25
<223> OTHER INFORMATION: phosphorothioate modification

<400> SEQUENCE: 52
tcgctacttg gctgcgactc ctgcattagg aagc                                    34

<210> SEQ ID NO 53
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 8, 12, 16, 20, 24
<223> OTHER INFORMATION: phosphorothioate modification

<400> SEQUENCE: 53
cttttcgggg aggacagaga gtggaaccaa ccg                                     33

<210> SEQ ID NO 54
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 24
<223> OTHER INFORMATION: phosphorothioate modification

<400> SEQUENCE: 54
ccactctctg tcctccccga aaagtgccac ctg                                     33

<210> SEQ ID NO 55
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 25
<223> OTHER INFORMATION: phosphorothioate modification

<400> SEQUENCE: 55
tgcaggagtc gcagccaagt agcgaagcga gcag                                    34

<210> SEQ ID NO 56
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 25
<223> OTHER INFORMATION: phosphorothioate modification

<400> SEQUENCE: 56
tcgctacttg gctgcgactc ctgcattagg aagc                                    34

<210> SEQ ID NO 57
<211> LENGTH: 33
<212> TYPE: DNA
```

-continued

```
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 24
<223> OTHER INFORMATION: phosphorothioate modification

<400> SEQUENCE: 57
cttttcgggg aggacagaga gtggaaccaa ccg                                33

<210> SEQ ID NO 58
<211> LENGTH: 39
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 10, 14, 18, 23, 28, 32, 36
<223> OTHER INFORMATION: phosphorothioate modification

<400> SEQUENCE: 58
gtggcacttt tcggggagga cagagagtgg aaccaaccg                          39

<210> SEQ ID NO 59
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 6, 11, 16, 20, 24, 29, 33, 37
<223> OTHER INFORMATION: phosphorothioate modification

<400> SEQUENCE: 59
tcctaatgca ggagtcgcag ccaagtagcg aagcgagcag                         40

<210> SEQ ID NO 60
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 14, 19, 23, 28, 33, 37
<223> OTHER INFORMATION: phosphorothioate modification

<400> SEQUENCE: 60
ctcgcttcgc tacttggctg cgactcctgc attaggaagc                         40

<210> SEQ ID NO 61
<211> LENGTH: 39
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 6, 10, 15, 19, 23, 28, 32, 36
<223> OTHER INFORMATION: phosphorothioate modification

<400> SEQUENCE: 61
ttggttccac tctctgtcct ccccgaaaag tgccacctg                          39

<210> SEQ ID NO 62
<211> LENGTH: 39
```

-continued

```
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 36
<223> OTHER INFORMATION: phosphorothioate modification

<400> SEQUENCE: 62
gtggcacttt tcggggagga cagagagtgg aaccaaccg                      39

<210> SEQ ID NO 63
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 37
<223> OTHER INFORMATION: phosphorothioate modification

<400> SEQUENCE: 63
tcctaatgca ggagtcgcag ccaagtagcg aagcgagcag                     40

<210> SEQ ID NO 64
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 37
<223> OTHER INFORMATION: phosphorothioate modification

<400> SEQUENCE: 64
ctcgcttcgc tacttggctg cgactcctgc attaggaagc                     40

<210> SEQ ID NO 65
<211> LENGTH: 39
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 36
<223> OTHER INFORMATION: phosphorothioate modification

<400> SEQUENCE: 65
ttggttccac tctctgtcct ccccgaaaag tgccacctg                      39

<210> SEQ ID NO 66
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 14, 19, 23, 28, 33, 37
<223> OTHER INFORMATION: phosphorothioate modification

<400> SEQUENCE: 66
ctcgcttcgc tacttggctg cgactcctgc attaggaagc                     40

<210> SEQ ID NO 67
```

<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 13, 18, 23, 28, 32
<223> OTHER INFORMATION: phosphorothioate modification

<400> SEQUENCE: 67
ccgcaagagg cccgcagtag taggttgagg ccgttga                              37

<210> SEQ ID NO 68
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 14, 19, 23, 27, 30, 34
<223> OTHER INFORMATION: phosphorothioate modification

<400> SEQUENCE: 68
gtaccggcat aaccaagcca ccgccgccgc aaggaat                              37

<210> SEQ ID NO 69
<211> LENGTH: 38
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 10, 14, 18, 22, 26, 31, 35
<223> OTHER INFORMATION: phosphorothioate modification

<400> SEQUENCE: 69
ctacagcatc cagggtgacc ctgccaccat acccacgc                             38

<210> SEQ ID NO 70
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 14, 18, 23, 27, 31, 34
<223> OTHER INFORMATION: phosphorothioate modification

<400> SEQUENCE: 70
cgaggatgac gatgagcgtg agcccgaagt ggcgagc                              37

<210> SEQ ID NO 71
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 14, 20, 25, 29, 33, 37
<223> OTHER INFORMATION: phosphorothioate modification

<400> SEQUENCE: 71
ctgactgcgt tagcaattta acagcaaccg cacctgtggc                           40

<210> SEQ ID NO 72
<211> LENGTH: 36
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 13, 17, 21, 25, 29, 33
<223> OTHER INFORMATION: phosphorothioate modification

<400> SEQUENCE: 72
agacgaaagg gcctcggatg cgtccggcgt agagga                                    36

<210> SEQ ID NO 73
<211> LENGTH: 39
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 10, 14, 18, 23, 28, 32, 36
<223> OTHER INFORMATION: phosphorothioate modification

<400> SEQUENCE: 73
gtggcacttt tcggggagga cagagagtgg aaccaaccg                                 39

<210> SEQ ID NO 74
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 6, 11, 16, 20, 24, 29, 33, 37
<223> OTHER INFORMATION: phosphorothioate modification

<400> SEQUENCE: 74
tcctaatgca ggagtcgcag ccaagtagcg aagcgagcag                                40

<210> SEQ ID NO 75
<211> LENGTH: 36
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 14, 19, 23, 28, 32
<223> OTHER INFORMATION: phosphorothioate modification

<400> SEQUENCE: 75
ggcctcaacc tactactgcg ggcctcttgc gggata                                    36

<210> SEQ ID NO 76
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 13, 17, 21, 26, 30, 34
<223> OTHER INFORMATION: phosphorothioate modification

<400> SEQUENCE: 76
ccttgcggcg gcggtggctt ggttatgccg gtactgc                                   37

<210> SEQ ID NO 77
<211> LENGTH: 38
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 13, 17, 22, 27, 31, 35
<223> OTHER INFORMATION: phosphorothioate modification

<400> SEQUENCE: 77
tgggtatggt ggcagggtca ccctggatgc tgtaggca                                 38

<210> SEQ ID NO 78
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 4, 9, 13, 18, 22, 26, 30, 34
<223> OTHER INFORMATION: phosphorothioate modification

<400> SEQUENCE: 78
cgccacttcg ggctcacgct catcgtcatc ctcggca                                  37

<210> SEQ ID NO 79
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 5, 9, 14, 19, 24, 29, 33, 37
<223> OTHER INFORMATION: phosphorothioate modification

<400> SEQUENCE: 79
acaggtgcgg ttgctgttaa attgctaacg cagtcaggca                               40

<210> SEQ ID NO 80
<211> LENGTH: 36
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 6, 10, 15, 19, 23, 28, 33
<223> OTHER INFORMATION: phosphorothioate modification

<400> SEQUENCE: 80
tctacgccgg acgcatccga ggccctttcg tcttca                                   36

<210> SEQ ID NO 81
<211> LENGTH: 39
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: 6, 10, 15, 19, 23, 28, 32, 36
<223> OTHER INFORMATION: phosphorothioate modification

<400> SEQUENCE: 81
ttggttccac tctctgtcct ccccgaaaag tgccacctg                                39

-continued

```
<210> SEQ ID NO 82
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 82
ccgcttgatg aagcgttaat tctgg                                      25

<210> SEQ ID NO 83
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 83
ggaacggctc acgctgt                                               17

<210> SEQ ID NO 84
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 84
aaggtctgga atacattgaa gc                                         22

<210> SEQ ID NO 85
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 85
cactgccgtc ctgatagc                                              18

<210> SEQ ID NO 86
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 86
ttaaaggtgc cgatagcc                                              18

<210> SEQ ID NO 87
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 87
attgccagag atgatttaat gc                                         22

<210> SEQ ID NO 88
<211> LENGTH: 19
<212> TYPE: DNA
<213> ORGANISM: Artificial Sequence
<220> FEATURE:
```

-continued

<223> OTHER INFORMATION: synthetic oligonucleotide

<400> SEQUENCE: 88
ctccaactcc aaccgtctg                                                          19

<210> SEQ ID NO 89
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 89
acgctcttca ttaccgatat tgc                                                     23

<210> SEQ ID NO 90
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 90
tgtattacac ggtattgatg ccacg                                                   25

<210> SEQ ID NO 91
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 91
gctttggtga agaatacgcg agca                                                    24

<210> SEQ ID NO 92
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 92
cctgctcgct tcgctact                                                           18

<210> SEQ ID NO 93
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 93
gcggtgcgga ctgttg                                                             16

<210> SEQ ID NO 94
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 94
ctctgcgtaa cggtatcg                                                           18

-continued

```
<210> SEQ ID NO 95
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 95
acatcaggtc aactttcaac t                                               21

<210> SEQ ID NO 96
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 96
tctgggcttt agggttgt                                                   18

<210> SEQ ID NO 97
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 97
gatgacgccg caggatat                                                   18
```